US012338491B2

(12) United States Patent
Majlessi et al.

(10) Patent No.: US 12,338,491 B2
(45) Date of Patent: Jun. 24, 2025

(54) METHODS TO DETECT RHINOVIRUS NUCLEIC ACIDS

(71) Applicant: GEN-PROBE INCORPORATED, San Diego, CA (US)

(72) Inventors: Mehrdad R. Majlessi, Escondido, CA (US); Ankur Shah, San Diego, CA (US); Amber Hillius, San Diego, CA (US); Pamela Douglass, Kansas City, MO (US); Daniel Kolk, Ramona, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 17/820,256

(22) Filed: Aug. 17, 2022

(65) Prior Publication Data

US 2023/0087588 A1 Mar. 23, 2023

Related U.S. Application Data

(63) Continuation of application No. 17/834,578, filed on Jun. 7, 2022, which is a continuation of application No. 16/497,229, filed as application No. PCT/US2018/024141 on Mar. 23, 2018, now Pat. No. 11,384,387.

(60) Provisional application No. 62/476,753, filed on Mar. 25, 2017.

(51) Int. Cl.
*C12Q 1/6844* (2018.01)
*C12Q 1/70* (2006.01)

(52) U.S. Cl.
CPC .......... *C12Q 1/6844* (2013.01); *C12Q 1/701* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 8,318,423 B2 | 11/2012 | Lee et al. | |
| 9,518,303 B2 | 12/2016 | Pyles et al. | |
| 9,650,685 B2 | 5/2017 | Lu et al. | |
| 2006/0003352 A1 | 1/2006 | Lipkin et al. | |
| 2006/0286580 A1* | 12/2006 | Lin | C12Q 1/689 435/6.16 |
| 2007/0092871 A1* | 4/2007 | Lodes | C12Q 1/705 435/6.12 |
| 2008/0102444 A1 | 5/2008 | Lee et al. | |
| 2010/0086908 A1 | 4/2010 | Prudent et al. | |
| 2010/0143881 A1 | 6/2010 | Lu et al. | |
| 2011/0097704 A1 | 4/2011 | Sampath et al. | |
| 2011/0111391 A1 | 5/2011 | Gonzalez et al. | |
| 2012/0089859 A1 | 4/2012 | Wang | |
| 2013/0209992 A1* | 8/2013 | Becker | C07H 21/04 435/5 |
| 2014/0057263 A1 | 2/2014 | Engel et al. | |
| 2014/0127671 A1 | 5/2014 | Yoo et al. | |
| 2014/0309138 A1 | 10/2014 | Poetter et al. | |
| 2015/0099261 A1 | 4/2015 | Curran et al. | |
| 2015/0211055 A1 | 7/2015 | Apte et al. | |
| 2015/0284782 A1 | 10/2015 | Reijans et al. | |
| 2016/0010152 A1 | 1/2016 | Shafer et al. | |
| 2017/0051364 A1 | 2/2017 | Lee et al. | |

FOREIGN PATENT DOCUMENTS

| | | |
|---|---|---|
| CN | 105018488 | * 11/2015 |
| CN | 106222304 A | 12/2016 |
| WO | 2009009900 A1 | 1/2009 |
| WO | 2012/046219 A2 | 4/2012 |

OTHER PUBLICATIONS

Bochkov et al., Journal of Clinical Microbiology, 2014, 52(7): 2461-2471. (Year: 2014).*
Zlateva et al., (Eur Respir J, 2014, 44:169-177. (Year: 2014).*
Osterback et al., Journal of Clinical Microbiology, 2013, 51(12):3960-3967. (Year: 2013).*
European Search Report dated Sep. 8, 2023 for corresponding European Application 231566456.8 (7 pages).
European Search Report mailed Jul. 23, 2024, issued in corresponding European Application No. 24168848.0, filed Mar. 23, 2018, 6 pages.

* cited by examiner

*Primary Examiner* — Nicole Kinsey White
(74) *Attorney, Agent, or Firm* — Sherbina Intellectual Property Law, PLLC; Nicholas V. Sherbina; Jeffrey E. Landes

(57) ABSTRACT

The disclosed disclosure is related to methods, compositions, and kits for targeting Rhinovirus nucleic acid. Compositions include amplification oligomers and/or detection probe oligomers. Kits and methods comprise at least one of these oligomers. Methods include uniplex and multiplex amplification and detection reactions.

**17 Claims, No Drawings
Specification includes a Sequence Listing.**

METHODS TO DETECT RHINOVIRUS NUCLEIC ACIDS

CROSS-REFERENCE TO RELATED APPLICATIONS

This application is a continuation of U.S. patent application Ser. No. 17/834,578, filed Jun. 7, 2022, which is a continuation of U.S. patent application Ser. No. 16/497,229, filed Sep. 24, 2019, now U.S. Pat. No. 11,384,387, which is a US national stage entry of PCT/US2018/024141 filed Mar. 23, 2018, which claims the benefit of priority of U.S. provisional application No. 62/476,753, which was filed on Mar. 25, 2017, each of which is incorporated herein by reference.

REFERENCE TO SEQUENCE LISTING

This application includes an electronic sequence listing in a file named "583359_SeqListing_St26", created Aug. 16, 2022, and containing 248 kilobytes, which is hereby incorporated by reference.

FIELD

The present disclosure relates to the detection of infectious agents, more specifically to the detection of Adenovirus, Metapneumovirus, and/or Rhinovirus. Compositions, methods and kits are described for the amplification and/or detection of Adenovirus, Metapneumovirus, and/or Rhinovirus by using in vitro nucleic acid amplification techniques.

INTRODUCTION

Infectious diseases, whether or bacterial, viral, or other origin, present acute and chronic challenges to human health. Many common infections affect the respiratory tract. Respiratory tract diseases are prevalent in patients of all ages, although often are more serious in the very young and the very old. Viruses include DNA viruses and RNA viruses.

Adenovirus (Adeno or Adv) may cause infections in a number of different organs including the gastrointestinal tract, the upper respiratory tract and the eyes. In individuals with a properly functioning immune system, Adenovirus infections are not typically associated with life-threatening disease. However, Adenovirus can cause serious infection in immunocompromised patients—such as HIV-positive individuals and in patients receiving bone marrow transplants. More than 50 different human Adenovirus serotypes have been identified. On the basis of various properties of Adenovirus, they have been divided into six major subgroups (subgenera or species A-F), with recent literature pointing towards the presence of a seventh serotype.

Early approaches for detecting Adeno detection relied mainly on serological tests and cell culture. In immunosuppressed patients, however, the use of serological tests is limited due to the impaired immune response, and evaluation of positive cultures is a relatively slow method. The introduction of PCR-based assays has provided new methods for the rapid, specific and sensitive detection of Adenovirus. Many of these diagnostic approaches, however, do not effectively cover all Adenovirus serotypes or use low stringency conditions to permit detection of the genetically highly diverse adenoviruses.

The homology of adenovirus DNA sequences between different species is low. Even conserved regions within the Adenovirus genome display only limited homology between adenoviruses from different species. In many instances, considerable differences in DNA sequence even exist between serotypes belonging to the same species. These facts underscore the difficulty to develop molecular tests that facilitate reliable screening for Adenovirus infections with the required broad specificity.

The human metapneumovirus (hMPV) was isolated for the first time in 2001 and is now recognized to be the second major cause of acute respiratory tract disease in infants and adults. It is estimated that it infects over 50% of infants by two years of age and almost all children by five years. hMPV accounts for roughly 5 to 15% of respiratory disease in hospitalized young children (Alto, 2004, The Journal of the American Board of Family Practice/American Board of Family Practice 17:466-469; Williams et al., 2004, N Engl J Med 350:443-450). Infection with hMPV is a significant burden of disease in at-risk premature infants, chronic lung disease of prematurity, congestive heart disease, and immunodeficiency (Martino et al., 2005, Biology of Blood and Marrow Transplantation: Journal of the American Society for Blood and Marrow Transplantation 11:781-796).

There are two distinct genetic lineages that have been established for hMPV and are designated as subtypes A and B. These lineages have further been divided into subgroups A1, A2, B1 and B2, as determined by performing phylogenetic analysis of sequence data, most often utilizing the fusion protein and G glycoprotein gene. No significant differences have been observed among patients infected with different subgroups of hMPV in terms of clinical manifestations (Wei, H., Tsao, K., Huang, C., Huang, Y., Lin, T. J Microbiol Immunol Infect. 2012 Sep. 26. pii: S1684-1182 (12)00151-X). Although information on the mode of transmission and virulence is not definitive, hMPV is likely spread by similar means as common respiratory viruses such as influenza. hMPV has been shown to co-infect with other respiratory pathogens. hMPV appears to provide only partial immunity following infection, likely due to the variety of strains and subtypes that circulate during any given season, and can re-infect individuals potentially leading to repeated episodes of illness. Infections occur mainly during late winter and early spring and the prevalence of each subtype of hMPV varies, seemingly both from year to year, and by location.

Likewise, the overall incidence of hMPV can vary from year to year and its prevalence has been reported to range from 2 to 26% in patients with symptoms of respiratory infection.

Human rhinoviruses (HRVs) are the most frequent cause of acute upper respiratory tract infections in humans and are usually associated with the common cold. Common colds caused by HRV occur throughout the year, with peaks of incidence in the autumn and spring, are one of the main reasons for absences from work and school, which have major economic impact. Rhinoviruses can also cause lower respiratory tract infections resulting in severe disease in children, in the elderly and in immunosuppressed patients.

The HRVs, which include over 100 different serotypes, are small, non-enveloped, positive (+)-strand RNA viruses. HRVs are one of the six genera of Picomaviridae, which also includes enteroviruses (EVs). Reverse transcription-polymerase chain reaction (RT-PCR) has been developed in the past few years for the detection of the HRVs in clinical specimens (see, e.g., Billaud et al. (2003) J. Virol. Methods 108: 223-228; Blomqvist et al. (1999) J. Clin, Microbiol. 37:2813-2816; Kares et al. (2003) J Clin Virol. 2004 February; 29(2):99-104; Loens et al. (2003) J. Clin. Microbiol. 41: 1971-1976; Savolainen et al. (2002) J. General Virol. 83:

333-340; Steininger et al. (2001) J. Clin. Microbiol. 39: 129-133). Most of these RT-PCR methods take advantage of the conserved sequences in the 5' noncoding region of the picornavirus genome.

The ability to detect HRV specifically—and particularly avoiding false positives that can result due to the relatedness of HRV and EV—is important to both diagnosis and selection of appropriate available therapy. Specific assays for HRV are also important for development of new drugs. For example, it is critical for clinical trial design that the participants be correctly identified as having an HRV infection where the trial is designed to evaluate a drug for use in treatment of HRV infections. Moreover, in other clinical trials, it may be important to exclude individuals infected with HRV. Further, the HRV detection assays must be simple to perform, provide easily interpreted results, and be relatively inexpensive to make them practical for use.

Conventional methods of differentiation of HRVs from EVs has been done either by virus neutralization assay, by selection with HRV-specific primer pairs, by distinguishing the amplification products of the two viruses based on differences in size, by sequencing the amplification products and comparing the sequence to known HRV and EV sequences, or by hybridization using HRV or EV-specific probes. These approaches can be time-consuming, expensive, and/or require a skilled technician who has experience in interpreting assay results accurately.

There remains a need in the field for a molecular based assay to permit the rapid, sensitive and specific detection of multiple adenovirus serotypes. There also remains a need in the field for the rapid, sensitive and specific detection of the multiple subtypes and subgroups of hMPV. There further remains a need in the field for methods for detecting RVs in a manner that is rapid, sensitive and specific, particularly with respect to the ability to distinguish an RV from an EV.

SUMMARY

It is an object of the present disclosure to provide methods, compositions and kits that can be used to specifically amplify and/or detect with high sensitivity one or more of an Adenovirus, a hMPV, and a HRV nucleic acid. Advantageously, the methods, compositions and kits may be used to specifically detect with high sensitivity many (eg. 5 or more, 10 or more, 20 or more, 30 or more, 40 or more or 50 or more), or all known serotypes and subgroups of adenovirus, hMPV and/or HRV.

1. A composition or kit comprising at least first and second amplification oligomers, wherein:
   the first amplification oligomer and second amplification oligomer are configured to amplify an Adenovirus amplicon of at least about 50 nucleotides in length comprising at least one Adenovirus position located in the range of nucleotide positions selected from 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47.

2. A composition or kit comprising at least first and second amplification oligomers, wherein:
   the first amplification oligomer and second amplification oligomer are configured to amplify a Metapneumovirus amplicon of at least about 50 nucleotides in length comprising at least one Metapneumovirus position located in the range of nucleotide positions selected from 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159.

3. A composition or kit comprising at least first and second amplification oligomers, wherein:
   the first amplification oligomer and second amplification oligomer are configured to amplify a Rhinovirus amplicon of at least about 50 nucleotides in length comprising at least one Rhinovirus position located in the range of nucleotide positions selected from 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76.

4. A composition or kit comprising at least first and second amplification oligomers configured for two or more target acids, wherein:
   (A) for a first target nucleic acid the first amplification oligomer and second amplification oligomer are configured to amplify an Adenovirus amplicon of at least about 50 nucleotides in length comprising at least one Adenovirus position located in the range of nucleotide positions selected from 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47; and
   (B) for a second target nucleic acid;
      (i) the first amplification oligomer and second amplification oligomer are configured to amplify a Metapneumovirus amplicon of at least about 50 nucleotides in length comprising at least one Metapneumovirus position located in the range of nucleotide positions selected from 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159; or
      (ii) the first amplification oligomer and second amplification oligomer are configured to amplify a Rhinovirus amplicon of at least about 50 nucleotides in length comprising at least one Rhinovirus position located in the range of nucleotide positions selected from 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76.

5. A composition or kit comprising at least first and second amplification oligomers configured for two or more target acids, wherein:
- (A) for a first target nucleic acid the first amplification oligomer and second amplification oligomer are configured to amplify a Metapneumovirus amplicon of at least about 50 nucleotides in length comprising at least one Metapneumovirus position located in the range of nucleotide positions selected from 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159; and
- (B) for a second target nucleic acid;
  - (i) the first amplification oligomer and second amplification oligomer are configured to amplify an Adenovirus amplicon of at least about 50 nucleotides in length comprising at least one Adenovirus position located in the range of nucleotide positions selected from 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47; or
  - (ii) the first amplification oligomer and second amplification oligomer are configured to amplify a Rhinovirus amplicon of at least about 50 nucleotides in length comprising at least one Rhinovirus position located in the range of nucleotide positions selected from 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76.

6. A composition or kit comprising at least first and second amplification oligomers configured for two or more target acids, wherein:
- (A) for a first target nucleic acid the first amplification oligomer and second amplification oligomer are configured to amplify a Rhinovirus amplicon of at least about 50 nucleotides in length comprising at least one Rhinovirus position located in the range of nucleotide positions selected from 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76; and
- (B) for a second target nucleic acid;
  - (i) the first amplification oligomer and second amplification oligomer are configured to amplify an Adenovirus amplicon of at least about 50 nucleotides in length comprising at least one Adenovirus position located in the range of nucleotide positions selected from 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47; or
  - (ii) the first amplification oligomer and second amplification oligomer are configured to amplify a Metapneumovirus amplicon of at least about 50 nucleotides in length comprising at least one Metapneumovirus position located in the range of nucleotide positions selected from 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159.

7. A composition or kit comprising at least first and second amplification oligomers configured for three or more target acids, wherein:
- (A) for a first target nucleic acid the first amplification oligomer and second amplification oligomer are configured to amplify an Adenovirus amplicon of at least about 50 nucleotides in length comprising at least one Adenovirus position located in the range of nucleotide positions selected from 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47; and
- (B) for a second target nucleic acid the first amplification oligomer and second amplification oligomer are configured to amplify a Metapneumovirus amplicon of at least about 50 nucleotides in length comprising at least one Metapneumovirus position located in the range of nucleotide positions selected from 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159; and
- (C) for a third target nucleic acid the first amplification oligomer and second amplification oligomer are configured to amplify a Rhinovirus amplicon of at least about 50 nucleotides in length comprising at least one Rhinovirus position located in the range of nucleotide positions selected from 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76.

8. The composition or kit of any one of claims 1 to 3, wherein the first amplification oligomer comprises a nucleic acid sequences that contains at least one 5-Me-dC, at least one non-Watson Crick base, at least one degenerate base, or a combination thereof.

9. The composition or kit of any of claims 1 to 3 or 8, wherein the second amplification oligomer comprises a nucleic acid sequence that contains at least one 5-Me-dC, or at least one non-Watson Crick base, or at least one degenerate base, or a combination thereof.

10. The composition or kit of claim 4 or claim 7, wherein the first amplification oligomer configured to amplify an Adenovirus amplicon comprises a nucleic acid sequences that contains at least one 5-Me-dC, or at least one non-Watson Crick base, or at least one degenerate base, or a combination thereof, and/or wherein the second amplification oligomer configured to amplify an Adenovirus amplicon comprises a nucleic acid sequences that contains at least one 5-Me-dC, or at least one non-Watson Crick base, or at least one degenerate base, or a combination thereof.

11. The composition or kit of claim 5 or claim 6, wherein the second target nucleic acid is an Adenovirus target nucleic acid and wherein the first amplification oligomer configured to amplify an Adenovirus amplicon comprises a nucleic acid sequences that contains at least one 5-Me-dC, at least one non-Watson Crick base, at least one degenerate base, or a combination thereof, or wherein the second amplification oligomer configured to amplify an Adenovirus amplicon comprises a nucleic acid sequences that contains at least one 5-Me-dC, at least one non-Watson Crick base, at least one degenerate base, or a combination thereof, or both.

12. The composition or kit of claim 5 or claim 7, wherein the first amplification oligomer configured to amplify a Metapneumovirus amplicon comprises a nucleic acid sequences that contains at least one 5-Me-dC, at least one non-Watson Crick base, at least one degenerate base, or a combination thereof, or wherein the second amplification oligomer configured to amplify an Metapneumovirus amplicon comprises a nucleic acid sequences that contains at least one 5-Me-dC, at least one non-Watson Crick base, at least one degenerate base, or a combination thereof, or both.

13. The composition or kit of claim 4 or claim 6, wherein the second target nucleic acid is an Metapneumovirus target nucleic acid and wherein the first amplification oligomer configured to amplify an Metapneumovirus amplicon comprises a nucleic acid sequences that contains at least one 5-Me-dC, at least one non-Watson Crick base, at least one degenerate base, or a combination thereof, or wherein the second amplification oligomer configured to amplify an Metapneumovirus amplicon comprises a nucleic acid sequences that contains at least one 5-Me-dC, at least one non-Watson Crick base, at least one degenerate base, or a combination thereof, or both.

14. The composition or kit of claim 6 or claim 7, wherein the first amplification oligomer configured to amplify a Rhinovirus amplicon comprises a nucleic acid sequences that contains at least one 5-Me-dC, at least one non-Watson Crick base, at least one degenerate base, or a combination thereof, or wherein the second amplification oligomer configured to amplify an Rhinovirus amplicon comprises a nucleic acid sequences that contains at least one 5-Me-dC, at least one non-Watson Crick base, at least one degenerate base, or a combination thereof, or both.

15. The composition or kit of claim 4 or claim 5, wherein the second target nucleic acid is an Rhinovirus target nucleic acid and wherein the first amplification oligomer configured to amplify an Rhinovirus amplicon comprises a nucleic acid sequences that contains at least one 5-Me-dC, at least one non-Watson Crick base, at least one degenerate base, or a combination thereof, or wherein the second amplification oligomer configured to amplify an Rhinovirus amplicon comprises a nucleic acid sequences that contains at least one 5-Me-dC, at least one non-Watson Crick base, at least one degenerate base, or a combination thereof, or both.

16. The composition or kit of any one of claims 1, 4, 7, 8, 10 or 11, wherein for the Adenovirus target nucleic acid the first amplification oligomer comprises a target hybridizing sequence selected from the group consisting of SEQ ID NOS: 1, 5, 11, 12, 25, 26, 31, 32, 33, 34, 35, 38, 71, 72, 73, 74.

17. The composition or kit of claim 5,6 or 9, wherein the second target nucleic acid is Adenovirus and wherein the first amplification oligomer comprises a target hybridizing sequence selected from the group consisting of SEQ ID NOS: 1, 5, 11, 12, 25, 26, 31, 32, 33, 34, 35, 38, 71, 72, 73, 74.

18. The composition or kit of any one of claims 1, 4, 7, 8, 10 or 11, wherein for the Adenovirus target nucleic acid the second amplification oligomer comprises a target hybridizing sequence selected from the group consisting of SEQ ID NOS: 2, 3, 6, 7, 8, 9, 13, 14, 15, 16, 27, 28, 42, 43, 44, 45, 46, 61, 62, 138, 139, 140, 141, 142, 143, 144, 145, 146, 147, 148, 149.

19. The composition or kit of claim 5, 6 or 9, wherein the second target nucleic acid is Adenovirus and wherein the second amplification oligomer comprises a target hybridizing sequence selected from the group consisting of SEQ ID NOS: 2, 3, 6, 7, 8, 9, 13, 14, 15, 16, 27, 28, 42, 43, 44, 45, 46, 61, 62, 138, 139, 140, 141, 142, 143, 144, 145, 146, 147, 148, 149.

20. The composition or kit of any one of claims 2, 5, 7, 8, 12 or 13, wherein for the Metapneumovirus target nucleic acid the first amplification oligomer comprises, consists of consists essentially of a target hybridizing sequence selected from the group consisting of SEQ ID NOS:52, 53, 151, 152, 153, 154, 160.

21. The composition or kit of claim 4, 6, or 9, wherein the second target nucleic acid is Metapneumovirus and wherein the first amplification oligomer comprises, consists of consists essentially of a target hybridizing sequence selected from the group consisting of SEQ ID NOS:52, 53, 151, 152, 153, 154, 160.

22. The composition or kit of any one of claims 2, 5, 7, 8, 12 or 13, wherein for the Metapneumovirus target nucleic acid the second amplification oligomer comprises, consists of consists essentially of a target hybridizing sequence selected from the group consisting of SEQ ID NOS:56, 68, 158, 177, 178.

23. The composition or kit of claim 4, 6, or 9, wherein the second target nucleic acid is Metapneumovirus and wherein the second amplification oligomer comprises, consists of consists essentially of a target hybridizing sequence selected from the group consisting of SEQ ID NOS:56, 68, 158, 177, 178.

24. The composition or kit of any one of claims 3, 6, 7, 8, 14 or 15, wherein for the Rhinovirus target nucleic acid the first amplification oligomer comprises, consists of consists essentially of a target hybridizing sequence selected from the group consisting of SEQ ID NOS:50, 51, 59, 60, 65, 75, 77 to 86, 102 to 108, 121 to 130.

25. The composition or kit of claim 4, 5, or 9, wherein the second target nucleic acid is Rhinovirus and wherein the first amplification oligomer comprises, consists of consists essentially of a target hybridizing sequence selected from the group consisting of SEQ ID NOS:50, 51, 59, 60, 65, 75, 77 to 86, 102 to 108, 121 to 130.

26. The composition or kit of any one of claims 3, 6, 7, 8, 14 or 15, wherein for the Rhinovirus target nucleic acid the second amplification oligomer comprises, consists of consists essentially of a target hybridizing sequence selected from the group consisting of SEQ ID NOS:57, 95 to 100, 115 to 119, 137.

27. The composition or kit of claim 4, 5, or 9, wherein the second target nucleic acid is Rhinovirus and wherein the second amplification oligomer comprises, consists of consists essentially of a target hybridizing sequence selected from the group consisting of SEQ ID NOS:57, 95 to 100, 115 to 119, 137.

28. The composition or kit of any one of claims 1 to 27, wherein the composition or kit further comprises a least one detection probe oligomer.

29. The composition or kit of any one of claims 1, 4, 7, 8 to 11, and 16 to 19, wherein the composition or kit further comprises an Adenovirus detection probe oligomer comprising a sequence selected from the group consisting of SEQ ID NOS:4, 10, 17, 18, 19, 20, 21, 22, 23, 24, 29, 30, 36, 37, 39, 40, 63, 64, 139, 140.

30. The composition or kit of any one of claim 5 or 6, wherein the second target nucleic acid is Adenovirus and wherein the composition or kit further comprises a detection probe oligomer comprising a sequence selected from the group consisting of SEQ ID Nos. 4, 10, 17, 18, 19, 20, 21, 22, 23, 24, 29, 30, 36, 37, 39, 40, 63, 64, 139, 140.

31. The composition or kit of any one of claims 1, 4, 7, 8 to 11, and 16 to 19, wherein the composition or kit further comprises an Adenovirus detection probe oligomer comprising a sequence that is from 18 to 36 nucleobases in length wherein the 18 to 36 nucleobases are all selected from contiguous nucleobases within SEQ ID NO:138.

32. The composition or kit of any one of claim 15 or 6, wherein the second target nucleic acid is Adenovirus and wherein the composition or kit further comprises a detection probe oligomer comprising a sequence that is from 18 to 36 nucleobases in length wherein the 18 to 36 nucleobases are all selected from contiguous nucleobases within SEQ ID NO:138.

33. The composition or kit of any one of claims 2, 5, 7, 8, 9, 12, 13, 20, 21, 22, and 23, wherein the composition or kit further comprises a Metapneumovirus detection probe oligomer comprising a sequence selected from the group consisting of SEQ ID Nos. 67, 69, 70, 155, 156, 157, 161, 162, 163, 164, 165, 166, 167, 168, 169, 170, 171, 172, 173, 174, 175, and 176.

34. The composition or kit of any one of claim 4 or 6, wherein the second target nucleic acid is Metapneumovirus and wherein the composition or kit further comprises a detection probe oligomer comprising a sequence selected from the group consisting of SEQ ID Nos. 67, 69, 70, 155, 156, 157, 161, 162, 163, 164, 165, 166, 167, 168, 169, 170, 171, 172, 173, 174, 175, and 176.

35. The composition or kit of any one of claims 2, 5, 7, 8, 9, 12, 13, 20, 21, 22, and 23, wherein the composition or kit further comprises a Metapneumovirus detection probe oligomer comprising a sequence that is from 18 to 36 nucleobases in length wherein the 18 to 36 nucleobases are all selected from contiguous nucleobases within SEQ ID NO:161 or within SEQ ID NO:155.

36. The composition or kit of any one of claim 4 or 6, wherein the second target nucleic acid is Metapneumovirus and wherein the composition or kit further comprises a detection probe oligomer comprising a sequence that is from 18 to 36 nucleobases in length wherein the 18 to 36 nucleobases are all selected from contiguous nucleobases within SEQ ID NO:161 or within SEQ ID NO:155.

37. The composition or kit of any one of claims 3, 6, 7, 8, 9, 14, 15, and 24 to 27, wherein the composition or kit further comprises a Rhinovirus detection probe oligomer comprising a sequence selected from the group consisting of SEQ ID Nos. 48, 49, 54, 87 to 94, 109 to 114, and 131 to 136.

38. The composition or kit of any one of claim 4 or 5, wherein the second target nucleic acid is Rhinovirus and wherein the composition or kit further comprises a detection probe oligomer comprising a sequence selected from the group consisting of SEQ ID Nos. 48, 49, 54, 87 to 94, 109 to 114, 131 to 136.

39. The composition or kit of any one of claims 28 to 38, wherein at least one of the detection probe oligomers comprises at least one 5-Me-dC, or at least one non-Watson Crick base, or at least one of a degenerate base, or a combination thereof.

40. The composition or kit of any one of claims 28 to 39, wherein at least one of the detection probe oligomers comprises a detectable label.

41. The composition or kit of claim 40, wherein the detectable label is a fluorophore.

42. The composition or kit of claim 40 or claim 41, wherein the detection probe oligomer is a dual labeled detection probe oligomer.

43. The composition or kit of claim 42, wherein the detection probe oligomer comprises a fluorescent detectable label and a quencher moiety that can quench a fluorescent emission from the fluorescent label.

44. The composition or kit of any one of claims 1, 4, 7 to 11, 16 to 19, 28 to 32, and 39 to 43, wherein the composition or kit further comprises one or more additional amplification oligomers each of which is configured to amplify an Adenovirus target nucleic acid.

45. The composition or kit of claim 5 or claim 6, wherein the second target nucleic acid is Adenovirus and wherein the composition or kit further comprises one or more additional amplification oligomers each of which is configured to amplify an Adenovirus target nucleic acid.

46. The composition or kit of claim 44 or 45, wherein each of the one or more additional amplification oligomers comprise a target hybridizing sequence separately selected from the group consisting of SEQ ID NOS: 1 to 9, 11 to 16, 25 to 28, 31 to 35, 38, 42 to 46, 61, 62, and 71 to 74.

47. The composition or kit of any one of claims 2, 5, 7, 8, 9, 12, 13, 20 to 23, 28, 33 to 36, and 39 to 43, wherein the composition or kit further comprises one or more additional amplification oligomers each of which is configured to amplify a Metapneumovirus target nucleic acid.

48. The composition or kit of claim 4 or claim 6, wherein the second target nucleic acid is Metapneumovirus and wherein the composition or kit further comprises one or more additional amplification oligomers each of which is configured to amplify a Metapneumovirus target nucleic acid.

49. The composition or kit of claim 47 or 48, wherein each of the one or more additional amplification oligomers comprise a target hybridizing sequence separately selected from the group consisting of SEQ ID NOS:52, 53, 56, 68, 151, 152, 153, 154, 158, 160, 177, 178.

50. The composition or kit of any one of claims 3, 6, 7, 8, 9, 14, 15, 24 to 28, and 37 to 43, wherein the composition or kit further comprises one or more additional amplification oligomers each of which is configured to amplify a Rhinovirus target nucleic acid.

51. The composition or kit of claim 4 or claim 5, wherein the second target nucleic acid is Rhinovirus and wherein the composition or kit further comprises one or more additional amplification oligomers each of which is configured to amplify a Rhinovirus target nucleic acid.

52. The composition or kit of claim 47 or 48, wherein each of the one or more additional amplification oligomers comprise a target hybridizing sequence separately selected from the group consisting of SEQ ID NOS:50, 51, 57, 59, 60, 65, 75, 77 to 86, 95 to 100, 102 to 108, 115 to 119, 121 to 130, 137.

53. The composition or kit of any one of claims 1, 4, 7 to 11, 16 to 19, 28 to 32, and 39 to 47, wherein the composition or kit comprises at least first and second amplification oligomers and one or more additional amplification oligomers configured to amplify an Adenovirus target nucleic acid each of the amplification oligomers independently comprising a sequences selected from the group consisting of: SEQ ID NOS:61, 62, 71, 72, 73, and 74.

54. The composition or kit of any one of claims 2, 5, 7, 8, 9, 12, 13, 20 to 23, 28, 33 to 36, 39 to 43, 46 to 49, and 53, wherein the composition or kit comprises at least first and second amplification oligomers and one or more additional amplification oligomers configured to amplify a Metapneumovirus target nucleic acid each of the amplification oligomers each independently comprising a sequences selected from the group consisting of: SEQ ID NOS:52, 53, 56, and 58.

55. The composition or kit of any one of claims 3, 6, 7, 8, 9, 14, 15, 24 to 28, 37 to 43, and 50 to 54, wherein the composition or kit comprises at least first and second amplification oligomers and one or more additional amplification oligomers configured to amplify a Rhinovirus target nucleic acid each of the amplification oligomers each independently comprising a sequences selected from the group consisting of: SEQ ID NOS:50, 51, 57, 59, 60, and 65.

56. The composition or kit of any one of claims 1, 4, 7 to 11, 16 to 19, 28 to 32, 39 to 47 and 53 to 55, wherein the composition or kit further comprises two Adenovirus detection probe oligomers, each of the detection probe oligomers independently comprising a sequence selected from the group consisting of SEQ ID NOS:63 and 64.

57. The composition or kit of any one of claims 2, 5, 7, 8, 9, 12, 13, 20 to 23, 28, 33 to 36, 39 to 43, 46 to 49, and 53 to 56, wherein the composition or kit further comprises three Metapneumovirus detection probe oligomers, each of the detection probe oligomers independently comprising a sequence selected from the group consisting of SEQ ID NOS:67, 69 and 70.

58. The composition or kit of any one of claims 3, 6, 7, 8, 9, 14, 15, 24 to 28, 37 to 43 and 50 to 57, wherein the composition or kit further comprises three Rhinovirus detection probe oligomers, each of the detection probe oligomers independently comprising a sequence selected from the group consisting of SEQ ID NOS:48, 49 and 54.

59. The composition or kit of any one of the preceding claims, wherein the composition or kit further comprises a nucleic acid target capture probe comprising a target hybridizing sequence and an immobilized probe binding region.

60. The composition or kit of claim 59, wherein the target hybridizing sequence is a poly-K nucleotide sequence.

61. The composition or kit of claim 60, wherein the poly-K nucleotide sequence is a random poly-GU sequence.

62. The composition or kit of claim 59, 60 or 61, wherein immobilized probe binding region is a homopolymeric nucleotide sequence, preferably comprising a nucleotide sequence selected from the group consisting of $T_{0-4}A_{10-36}$.

63. The composition or kit of any one of claims 1 to 62, wherein the composition further comprises an enzyme, a buffer, dNTPs, or a combination thereof.

64. A method for the determining the presence of absence of an Adenovirus target nucleic acid, a Metapneumovirus target nucleic acid, a Rhinovirus target nucleic acid, or a combination thereof in a sample, the method comprising the steps of:
  (A) contacting a sample with a combination of amplification oligomers from any one of claims 1 to 58;
  (B) performing an in vitro nucleic acid amplification reaction wherein any of an Adenovirus target nucleic acid, a Metapneumovirus target nucleic acid, or a Rhinovirus target nucleic acid in the sample is used by the combination of amplification oligomers configured to amplify that target nucleic acid to generate an amplification product; and
  (C) detecting the amplification product; thereby determining the presence or absence of the target nucleic acid in the sample.

65. The method of claim 64, wherein the sample is a sample derived from a human.

66. The method of claim 65, wherein the sample is a mucosal sample.

67. The method of claim 65 or claim 66, wherein the sample is obtained using a nasopharyngeal swab.

68. The method of any one of claims 64 to 67, wherein, before step (A) a sample preparation step is performed to separate any target nucleic acid in the sample away from other sample components.

69. The method of claim 68, wherein the sample preparation step comprises a target capture step.

70. The method of claim 69, wherein the target capture step comprise contacting the sample with a nucleic acid target capture probe comprising a target hybridizing sequence and an immobilized probe binding region.

71. The method of claim 70, wherein the target hybridizing sequence is a poly-K nucleotide sequence.

72. The method of claim 71, wherein the poly-K nucleotide sequence is a random poly-GU sequence.

73. The method of claim 70, 71 or 72, wherein immobilized probe binding region is a homopolymeric nucleotide sequence, preferably comprising a nucleotide sequence selected from the group consisting of $T_{0-4}A_{10-36}$.

74. The method of any one of claims 64 to 73, wherein the detecting step (C) is performed using one or more detection probe oligomers.
75. The method of claim 74, wherein each of the one or more detection probe oligomers are individually selected from the group consisting of: SEQ ID NOS:4, 10, 17, 18, 19, 20, 21, 22, 23, 24, 29, 30, 36, 37, 39, 40, 63, 64, 139, 140, 67, 69, 70, 155, 156, 157, 161, 162, 163, 164, 165, 166, 167, 168, 169, 170, 171, 172, 173, 174, 175, 176, 48, 49, 54, 87 to 94, 109 to 114, and 131 to 136.
76. The method of claim 74 or 75, wherein at least one of the detection probe oligomers comprises at least one 5-Me-dC, or at least one non-Watson Crick base, or at least one of a degenerate base, or a combination thereof.
77. The method of claim 74, 75 or 76, wherein at least one of the detection probe oligomers comprises a detectable label.
78. The method of claim 77, wherein the detectable label is a fluorophore.
79. The method of claim 77 or claim 78, wherein the detection probe oligomer is a dual labeled detection probe oligomer.
80. The method of claim 79, wherein the detection probe oligomer comprises a fluorescent detectable label and a quencher moiety that can quench a fluorescent emission from the fluorescent label.
81. The method of any one of claims 64 to 80, wherein the in vitro nucleic acid amplification reaction comprises thermal cycling.
82. The method of any one of claims 64 to 81, wherein the in vitro nucleic acid amplification reaction comprises PCR with a polymerase enzyme having 5' to 3' exonuclease activity.
83. The method of any one of claims 75 to 80, wherein the in vitro nucleic acid amplification reaction is performed using an enzyme having 5' to 3' exonuclease activity.
84. The method of any one of claims 77 to 80, wherein the in vitro nucleic acid amplification reaction is performed using an enzyme having 5' to 3' exonuclease activity and wherein an amplification product is detected by determining a fluorescence value that is above a predetermined threshold value.
85. A system for performing one or more steps of the method of claim 64, 65, 66, 67, 68, 69, 70, 71, 72, 73, 74, 75, 76, 77, 78, 79, 80, 81, 82, 83, or 84.
86. The system of claim 85, wherein the system is an automated system.
87. The system of claim 85 or 86, wherein the system performs all of the steps of the method.
88. A method for the in vitro detection of an Adenovirus target nucleic acid, a Metapneumovirus target nucleic acid, a Rhinovirus target nucleic acid, or a combination thereof in a sample, wherein the method comprises contacting an Adenovirus target nucleic acid, a Metapneumovirus target nucleic acid, and/or a Rhinovirus target nucleic acid with a detection probe oligomer from any of claims 29 to 43, wherein hybridization between the detection probe oligomers and the target nucleic acid to which the detection probe oligomer is configured to hybridize indicates the presence of that target nucleic acid.
89. The method of claim 88, wherein the method comprises contacting an amplification product from the Adenovirus target nucleic acid, the Metapneumovirus target nucleic acid, and/or the Rhinovirus target nucleic acid with the detection probe oligomer, wherein hybridization between the detection probe oligomers and the amplification product to which the detection probe oligomer is configured to hybridize indicates the presence of that target nucleic acid from which the amplification product was generated.
90. The method of claim 88 or 89, wherein the in vitro detection reaction is performed using an enzyme having 5' to 3' exonuclease activity.
91. The method of any one of claims 88 to 90, wherein the in vitro detection reaction is performed using an enzyme having 5' to 3' exonuclease activity and wherein the target nucleic acid or the amplification product generated therefrom is detected by determining a fluorescence value that is above a predetermined threshold value.
92. A system for performing the in vitro detection reaction of any one of claims 88 to 91.
93. The system of claim 92, wherein the system is an automated system.
94. The system of claim 92 or 93, wherein the system performs all of the steps of the method.
95. A dried composition comprising one or more of the amplification oligomers from any one of claims 1 to 27.
96. A dried composition comprising one or more of the amplification oligomers from any one of claims 44 to 55.
97. A dried composition comprising one or more of the detection probe oligomers from any of claims 29 to 43 or 56 to 58.
98. A dried composition comprising a combination of amplification oligomers and/or detection probe oligomers from any one of claims 1 to 58.
99. The dried composition of any one of claims 95 to 98, wherein the dried composition further comprises an enzyme, dNTPs, or both.
100. The dried composition of claim 99, wherein the enzyme having 5' to 3' exonuclease activity.
101. The dried composition of claim 99 or claim 100, wherein the enzyme is a polymerase enzyme.
102. The dried composition of any one of claims 95 to 101, wherein the dried composition has an inorganic salt concentration of 10 mM or less.
103. The dried composition of any one of claims 95 to 102, wherein the dried composition has an inorganic salt concentration of 7 mM or less.
104. The dried composition of any one of claims 95 to 103, wherein the dried composition has an inorganic salt concentration of 5 mM or less.
105. The dried composition of any one of claims 95 to 101, wherein the dried composition has an inorganic salt concentration of between about 0.5 mM to about 10 mM.

DETAILED DESCRIPTION

Nucleic acid oligomer sequences are disclosed that may serve as primers for amplification detection of Adenovirus, Metapneumovirus, and/or Rhinovirus nucleic acids. These target nucleic acids may be detected in a sample by using methods of in vitro nucleic acid amplification—such as PCR (e.g., TAQMAN™ PCR)—or transcription-mediated amplification—such as TMA® reaction (Hologic, Inc.) or NASBA. Probes for detection of the amplified nucleic acid sequences are also described. Detection probes hybridize specifically to at least a portion of the amplified sequence, either after completion of or during the amplification process. Methods disclosed herein can be used to amplify and detect Adenovirus, Metapneumovirus, and/or Rhinovirus nucleic acids present in samples from or derived from animals and humans.

The disclosed nucleic acid sequences and methods are useful for amplifying and detecting Adenovirus, Metapneumovirus, and/or Rhinovirus nucleic acids from or derived from viral particles present in a sample in a relatively short time so that diagnosis can be made quickly, allowing initiation of effective treatment and limiting spread of the virus. The methods are useful for screening for individuals who have Adenovirus, Metapneumovirus, and/or Rhinovirus infections and are particularly useful for screening patients who have a higher risk of death or serious complications from Adenovirus, Metapneumovirus, and/or Rhinovirus infections, eg., the young, elderly, or immunocompromised individuals. The methods are also useful for rapid screening of many samples. The methods are useful because they minimize the risk of exposure of laboratory personnel to the infectious agents, thereby limiting the risk of infection and spread of the virus. Thus, the methods and compositions disclosed herein respond to a need for rapid, sensitive, and specific testing of clinical samples that may contain Adenovirus, Metapneumovirus, and/or Rhinovirus.

The disclosed probe sequences may be used as primers, and the disclosed primers may be used as probes. The same is true for the disclosed probe domains and primer domains. Thus, the probe domains disclosed herein may be used as primer domains. Likewise, primer domains disclosed herein may be used as probe domains.

The amplification oligomers disclosed herein are further contemplated as components of multiplex amplification reactions wherein several different amplicon species can be produced from an assortment (eg. two or more, three or more, for or more, five or more, six or more, or even ten or more) of target-specific primers. For example, it is contemplated that more than one of the amplification systems disclosed herein can be combined to result in a multiplex assay that is both robust and broad in its capacity for target detection—such as the ability to amplify and detect nucleic acid from at least two, at least three, at least four or more organisms. For example, the amplification systems disclosed herein can be combined to result in a multiplex assay for target detection of: Adenovirus target nucleic acid and at least one additional target nucleic acid; Metapneumovirus target nucleic acid and at least one additional target nucleic acid; Rhinovirus target nucleic acid and at least one additional target nucleic acid; Adenovirus target nucleic acid and Metapneumovirus target nucleic acid and at least one additional target nucleic acid; Adenovirus target nucleic acid and Rhinovirus target nucleic acids and at least one additional target nucleic acid; Rhinovirus target nucleic acid and Metapneumovirus target nucleic acid and at least one additional target nucleic acid; Adenovirus target nucleic acid and Metapneumovirus target nucleic acids and Rhinovirus target nucleic acid and at least one additional target nucleic acid. The multiplex assay described herein includes providing two or more amplification systems that each amplify and detect a different subtype or subgroup of a species, different species of an organism, or a combination thereof.

To aid in understanding aspects of the disclosure, some terms used herein are described in more detail. All other scientific and technical terms used herein have the same meaning as commonly understood by those skilled in the relevant art, such as may be provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and references cited herein. Unless mentioned otherwise, the techniques employed or contemplated herein are standard methods well known to a person of ordinary skill in the art of molecular biology.

Definitions

It is to be noted that the term "a" or "an" "the" entity refers to one or more of that entity; for example, "a nucleic acid," is understood to represent one or more nucleic acids. As such, the terms "a" (or "an"), "one or more," and "at least one" can be used interchangeably herein.

Sample. A "sample" or "specimen", including "biological" or "clinical" samples may contain or may be suspected of containing Adeno, hMPV and/or HRV organisms or components thereof, such as nucleic acids or fragments of nucleic acids. A sample may be a complex mixture of components. Samples include "biological samples" which include any tissue or material derived from a living or dead mammal or organism, including, for example, blood, plasma, serum, blood cells, saliva, mucous and cerebrospinal fluid. Samples may also include samples of in vitro cell culture constituents including, eg., conditioned media resulting from the growth of cells and tissues in culture medium. The sample may be treated to physically or mechanically disrupt tissue or cell structure to release intracellular nucleic acids into a solution which may contain enzymes, buffers, salts, detergents and the like, to prepare the sample for analysis. In one step of the methods described herein, a sample is provided that is suspected of containing at least an Adeno, hMPV and/or HRV target nucleic acid. Accordingly, this step excludes the physical step of obtaining the sample from a subject.

Nucleic add. This refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5 methyl 2' deoyxcytosine (5-Me-dC), isoguanine; *The Biochemistry of the Nucleic Acids* 5-36, Adams et al., ed., 11$^{th}$ ed., 1992, Abraham et al., 2007, BioTechniques 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, Biochemistry 43(42):13233-41). Nucleic acids may include modified bases to alter the function or behaviour of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

Polynucleotide and Oligonucleotide. These terms denote a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid. Oligonucleotide is may be used interchangeably with "oligomer and "oligo" and refers to a nucleic acid having generally less than 1,000 nucleotide (nt) residues, including polymers in a range of from about 5 nt residues to about 900 nt residues, from about 10 nt residues to about 800 nt residues with a lower limit of about 12 to 15 nt and an upper limit of about 40 to 600 nt, and other embodiments are in a range having a lower limit of about 15 to 20 nt and an upper limit of about 22 to 100 nt. It is understood that these ranges are exemplary only, and an oligonucleotide may contain each whole number included in the range. Oligonucleotides may be purified from naturally occurring sources, but may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (eg., a T7 provider), and it may function to prevent hybridization or impede primer extension if appropriately situated and/or modified.

Nucleotide. This is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me, or 2' methoxy). As used herein, methoxy oligonucleotides containing "T" residues have a methoxy group at the 2' position of the ribose moiety, and a uracil at the base position of the nucleotide. "C residues" present in an oligonucleotide (e.g., a primer or probe) include methylated (e.g., 5-Me-dC) and unmethylated cytosines unless the context indicates otherwise.

Non-nucleotide unit. This is a unit that does not significantly participate in hybridization of a polymer. Such units must not, for example, participate in any significant hydrogen bonding with a nucleotide, and would exclude units having as a component one of the five nucleotide bases or analogs thereof.

Target nucleic acid. This is a nucleic acid comprising a "target sequence" to be amplified. Target nucleic acids may be DNA or RNA and may be either single-stranded or double-stranded. The target nucleic acid may include other sequences besides the target sequence that may be amplified. Typical target nucleic acids are or are derived from the Adv, hMPV and HRV genomes.

Target sequence. This term refers to the particular nucleotide sequence of the target nucleic acid that is to be amplified. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. The terms "target(s) a sequence" or "target(s) a target nucleic acid" as used herein in reference to a region of an Adeno, hMPV or HRV nucleic acid refers to a process whereby an oligonucleotide stably hybridizes to the target sequence in a manner that allows for amplification and/or detection as described herein.

In one embodiment, the oligonucleotide is complementary to the target sequence and contains no mismatches. In another embodiment, the oligonucleotide is complementary but contains 1; or 2; or 3; or 4; or 5 or more mismatches with the target sequence. In another embodiment, the oligonucleotide is complementary to the target sequence but contains one or a combination of a degenerate nucleotide residue, a non-Watson Crick residue, or a nucleoside analog. Preferably, the oligonucleotide that stably hybridizes to the target sequence includes at least 10, 11, 12, 13, 14, 15, 16, 17, 18, 19, 20, 21, 22, 23, 24, 25, 30, 35, 40, 45 or 50 contiguous nucleotides complementary to the target sequence. It is understood that at least 10 and as many as 50 is an inclusive range such that 10, 50 and each whole number there between are included. The term "configured to target a sequence" as used herein means that the target hybridizing region of an amplification oligonucleotide is designed to have a polynucleotide sequence that could target a sequence of the referenced Adeno, hMPV or HRV region. Such an amplification oligonucleotide is not limited to targeting that sequence only, but is rather useful as a composition, in a kit or in a method for targeting an Adeno, hMPV or HRV target nucleic acid, as is described herein. The term "configured to" denotes an actual arrangement of the polynucleotide sequence configuration of the amplification oligonucleotide target hybridizing sequence.

Isolated, Separating, Purifying. refer to taking a nucleic acid from its natural milieu, but these terms do not necessarily connote any degree of purification. These terms mean that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

Region. This term refers to a portion of a nucleic acid wherein said portion is smaller than the entire nucleic acid. For example, when the nucleic acid in reference is an oligonucleotide promoter provider, the term "region" may be used refer to the smaller promoter portion of the entire oligonucleotide. Similarly, and also as example only, when the nucleic acid is a target nucleic acid, the term "region" may be used to refer to a smaller area of the nucleic acid.

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence. Unless otherwise indicated, reference to an Adv, hMPV or HRV nucleic acid includes the respective Adv, hMPV, or HRV RNA and DNA equivalents thereof.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

Corresponds. As used herein, a nucleic acid "corresponds" to a specified nucleic acid if the nucleic acid is 100% identical or complementary to the specified nucleic acid.

Substantially corresponding to. As used herein, a nucleic acid "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. Substantially corresponding nucleic acids vary by at least one nucleotide from the specified nucleic acid. This variation may be stated in terms of a percentage of identity or complementarity between the nucleic acid and the specified nucleic acid. Thus, nucleic acid substantially corresponds to a reference nucleic acid sequence if these percentages of base identity or complementarity are from less than 100% to about 80% (inclusive of all whole and rational numbers therein).

Blocking moiety. As used herein, a "blocking moiety" is a substance used to "block" the 3'-terminus of an oligonucleotide or other nucleic acid so that it cannot be efficiently extended by a nucleic acid polymerase. Oligomers not intended for primer-based extension by a nucleic acid polymerase may include a blocker group that replaces the 3'OH to prevent the enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

Amplification oligomer. An "amplification oligomer", which may also be called an "amplification oligonucleotide" or a "primer" is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a primer that hybridizes to a target nucleic acid and contains a 3' OH end that is extended by a polymerase in an amplification process. Another example of an amplification oligomer is a "promoter-based amplification oligomer," which comprises a target hybridizing sequence, and a promoter sequence for initiating transcription by an appropriate polymerase. Size ranges for amplification oligonucleotides include those comprising target hybridizing regions that are about 10 to about 70 nt long (inclusive of all whole and rational numbers therein). In one embodiment, an amplification oligomer may optionally contains one or a combination of a degenerate nucleotide residue, a non-Watson Crick residue, or a nucleoside analog. An amplification oligomer designated to comprise at least one degenerate nucleobase is thus a collection of amplification oligomer species each independently having one of the nucleic acid residues represented by the degenerate nucleotide.

Amplification. This refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, eg., produced by using an amplification oligonucleotide that hybridizes to, and initiates polymerization from, an internal position of the target nucleic acid. Known amplification methods include both thermally cyclical and isothermal amplification methods. For some embodiment, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods (see e.g., U.S. Pat. Nos. 4,786,600; 4,683,195, 4,683,202, and 4,800,159; 5,427,930 and 5,516,663; and 5,422,252; 5,547, 861; and 5,648,211).

By "assay conditions" is meant conditions permitting stable hybridization of an oligonucleotide to a target nucleic acid. Assay conditions do not require preferential hybridization of the oligonucleotide to the target nucleic acid.

In cyclic amplification methods that detect amplicons in real-time, the term "Threshold cycle" (Ct) is a measure of the emergence time of a signal associated with amplification of target, and is generally 10×standard deviation of the normalized reporter signal. Once an amplification reaches the "threshold cycle," generally there is considered to be a positive amplification product of a sequence to which the probe binds. The identity of the amplification product can then be determined through methods known to one of skill in the art, such as gel electrophoresis, nucleic acid sequencing, and other such well known methods.

Real-time amplification. As used herein, the term "real-time amplification" refers to amplification of target nucleic acid that is monitored by real-time detection means.

Amplicon. This term, which is used interchangeably with "amplification product", refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

Probe. A probe, also known as a "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (eg., U.S. Pat. Nos. 5,118,801; 5,312,728; 6,849,412; 6,835,542; 6,534,274; and 6,361,945; and US Pub. No. 20060068417). In a preferred embodiment, the detection probe comprises a 2' methoxy backbone which can result in a higher signal being obtained. In another preferred embodiment, the probe comprises a fluorophore covalently attached to the 5'-end of the probe and a quencher at the 3'-end. Such probes are known as TAQMAN™ probes. In another embodiment, a probe may optionally contains one or a combination of a degenerate nucleotide residue, a non-Watson Crick residue, or a nucleoside analog. A probe designated to comprise at least one degenerate nucleobase is thus a collection of probe species each independently having one of the nucleic acid residues represented by the degenerate nucleotide.

Stable. By "stable" or "stable for detection" is meant that the temperature of a reaction mixture is at least 2.deg.C below the melting temperature of a nucleic acid duplex.

Label. As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels (e.g., U.S. Pat. Nos. 5,656,207, 5,658,737, and 5,639,604)), or fluorophore. Labels may be detectable in a homogeneous assay in which bound labeled probe in a mixture exhibits a detectable change different from that of an unbound labeled probe, e.g., instability or differential degradation properties (e.g., U.S. Pat. Nos. 5,283,174, 5,656,207, and 5,658,737). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, e.g., BLACK HOLE QUENCHER™ (or BHQ™, BHQ-1™, or BHQ-2™) or TAMRA™ compounds. Synthesis and methods of attaching labels to nucleic acids and detecting labels are well known (e.g., Sambrook et al., *Molecular Cloning. A Laboratory Manual,* 2nd ed. (Cold Spring Harbor Laboratory Press, Cold Spring Harbor, N.Y., 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a different detectable signal (e.g., U.S. Pat. Nos. 6,180,340 and 6,350,579).

Capture oligonucleotide. As used herein, a "capture oligonucleotide," "target capture oligonucleotide" or "capture probe" refers to a nucleic acid oligomer that hybridizes to a target sequence in a target nucleic acid by and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-K poly-GU, poly-GT, or poly U sequences to bind non-specifically to a target nucleic acid and link it to an immobilized probe on a support. (see e.g., PCT Pub No. WO 2008/016988 and U.S. Pat. No. 9,051,601). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence. Thus, a non-limiting example of preferred nucleic acid tails can in some embodiments include $T_{1-4}A_{10-36}$ sequences.

Immobilized oligonucleotide. As used herein, an "immobilized oligonucleotide", "immobilized probe" or "immobilized nucleic acid" refers to a nucleic acid binding partner that joins a capture oligomer to a support, directly or indirectly to facilitate separation of a capture probe bound target nucleic acid from unbound material in a sample. One embodiment of an immobilized probe is an oligomer joined to a support, such as nitrocellulose, nylon, glass, polyacrylate, mixed polymers, polystyrene, silane, polypropylene, metal, or other compositions, of which one embodiment is magnetically attractable particles.

Complementary. By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing, or are modified nucleotides such as abasic residues, modified nucleotides or nucleotide analogs. Sufficiently complementary contiguous sequences typically are at least 80%, or at least 90%, complementary to a sequence to which an oligomer is intended to specifically hybridize (a %-complementarity range includes all whole and rational numbers of the range). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary.

Preferentially hybridize. By "preferentially hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (e.g., Sambrook et al., *Molecular Cloning. A Laboratory Manual,* $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57).

Nucleic acid hybrid. By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

Sample preparation. This refers to any steps or methods that treat a sample for subsequent amplification and/or detection of one or more of an Adv, hMPV or HRV nucleic acid present in the sample. The target nucleic acid may be a minority component in the sample. Sample preparation may include any known method of isolating or concentrating components, such as viruses or nucleic acids using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically captures a target nucleic acid and separates it from other sample components (eg., as described in U.S. Pat. Nos. 6,110,678; 9,051,601, and PCT Pub. No. WO 2008/016988).

Specificity. The term "specificity," in the context of an amplification system, is used herein to refer to the characteristic of an amplification system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio).

Sensitivity. The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

Relative fluorescence unit. As used herein, the term "relative fluorescence unit"("RFU") is an arbitrary unit of measurement of fluorescence intensity. RFU varies with the characteristics of the detection means used for the measurement.

References, particularly in the claims, to "the sequence of SEQ ID NO: X" refer to the base sequence of the corresponding sequence listing entry and do not require identity of the backbone (e.g., RNA, 2'-O-Me RNA, or DNA) or base modifications (e.g., methylation of cytosine residues) unless otherwise indicated.

A "degenerate" position in an oligomer refers to a position where more than one base pair is present in a population of the oligomer. For example, in SEQ ID NO: 81, the eighth nucleotide is R, which represents G or A. Oligomers with degenerate positions can be synthesized by providing a mixture of nucleotide precursors corresponding to the desired degenerate combination at the step of the synthesis where incorporation of a degenerate position is desired. The resulting oligomers are a mixture of species each containing one of the nucleotides represented by the degenerate designation.

A "non-Watson Crick" (NWC) position in an oligomer refers to a position where the oligomer is configured to hybridize to at least one target nucleic acid sequence with a non-Watson Crick pairing, such as G-U, G-T, or G-A (either the G or the U/T/A can be the base in the oligomer). In some embodiments, the NWC position is configured to hybridize via a wobble (G-U or G-T) or purine-purine (G-A) pair.

Oliaonucleotides for the Amnlification of Adenovirus. Metanneumovirs. And/or Rhinovirus Oligonucleotides for amplifying an each of an Adenovirus, Metapneumovirus, and/or Rhinovirus target nucleic acid typically comprise at least two amplification oligomers per target. Some embodiments of the disclosure may utilise two, three, four, five, six or more amplification oligomers per target in, for example, multiplex amplification assays. Thus, by way of example, oligonucleotides for amplifying each target organism may comprise one, two, three, four, five or more forward amplification primers and one, two, three, four, five or more reverse amplification primers. For example, oligonucleotides for amplifying Adenovirus may comprise one, two, three, four, five or more forward amplification primers and one, two, three, four, five or more reverse amplification primers. Oligonucleotides for amplifying hMPV may comprise one, two, three, four, five or more forward amplification primers and one, two, three, four, five or more reverse amplification primers. Oligonucleotides for amplifying HRV may comprise one, two, three, four, five or more forward amplification primers and one, two, three, four, five or more reverse amplification primers. Moreover, the subtypes or subgroups of a target organism may require at least two amplification oligomers, each comprising a nucleotide sequence that is specific for a different member or members of one or more of the organism's subtypes/subgroups.

Oligonucleotides for detecting each of an Adenovirus, Metapneumovirus, and/or Rhinovirus target nucleic acid typically comprise at least one detection oligomer per target. Some embodiments of the disclosure may utilise two, three, four, five, six or more detection probe oligomers per target in, for example, a multiplex detection assay. For example, oligonucleotides for detecting Adenovirus may comprise one, two, three, four or more detection probe oligomers. Oligonucleotides for detecting hMPV may comprise one, two, three, four or more detection probe oligomers. Oligonucleotides for detecting HRV may comprise one, two, three, four or more detection probe oligomers. Moreover, the subtypes or subgroups of a target organism may require at least two detection probe oligomers, each comprising a nucleotide sequence that is specific for a different member or members of one or more of the organism's subtypes/subgroups. Combinations of oligomers for the multiplexed amplifying and detecting of one or more of Adenovirus, Metapneumovirus, and Rhinovirus target nucleic acids typically comprise at least two forward amplification oligomers, at least two reverse amplification oligomers, and at least two detection probe oligomers. Some embodiments of the disclosure may utilise two, three, four, five, or even six or more amplification oligomers and two, three, four, five or even six or more probes for each intended target nucleic acid. Thus, by way of example, oligonucleotides for the multiplexed amplifying and detecting of a number of targets may comprise from 6 to 40 amplification oligomers and from 3 to 15 detection probe oligomers.

The methods for detecting an Adenovirus, Metapneumovirus, and/or Rhinovirus target nucleic acid (including an amplicon) optionally include a detecting step that uses at least one probe that binds specifically to the amplified product (RNA or DNA amplicon, preferably DNA amplicon). Preferably, the probe is labeled and produces a signal detected in a homogeneous system, that is, without separation of bound probe from unbound probe. Other examples of probes may be labeled with a fluorescent compound which emits a detectable signal only when the probe is bound to its target, e.g., a TAQMAN™ detection probe as described herein.

In one embodiment, at least one of the amplification oligomers is configured to specifically hybridize to a region within a target sequence of Adenovirus corresponding to nucleotides 1 to 99 of SEQ ID No. 47, or corresponding to nucleotides 83 to 175 of SEQ ID No. 47. In one embodiment, at least two amplification oligomers are used, wherein each of said at least two amplification oligomers is from 10 to about 50 nucleotides in length and wherein the amplification oligomers are respectively configured to specifically hybridize to regions within a target sequence of Adenovirus selected from the group consisting of from nucleotides 1 to 99 of SEQ ID No. 47 and from nucleotides 83 to 175 of SEQ ID No. 47 in order to generate an amplicon that can be subsequently detected. In one embodiment, at least one of the amplification oligomers is configured to specifically hybridize to a region within a target sequence of Adenovirus corresponding to nucleotides 52 to 99 and/or 40 to 87 and/or 1 to 23 and/or 7 to 23 and/or 7 to 45 and/or 139 to 155 and/or 103 to 175 and/or 83 to 99 and/or 83 to 98 SEQ ID No. 47 in order to generate an amplicon that can be subsequently detected. In one embodiment, at least one of the amplification oligomers is configured to specifically hybridize to a region within a target sequence of Adenovirus corresponding to nucleotides 52 to 74 and/or 76 to 99 and/or 40 to 56 and/or 65 to 87 and/or 1 to 18 and/or 7 to 23 and/or 28 to 45 and/or 27 to 45 and/or 26 to 45 and/or 139 to 155 and/or 103 to 123 and/or 159 to 175 and/or 83 to 99 and/or 83 to 98 of SEQ ID No. 47 in order to generate an amplicon that can be subsequently detected.

Oligonucleotides for amplifying and/or detecting the Adenovirus target nucleic acid include oligonucleotide sequences selected from the group consisting of SEQ ID NOS: 1 to 46, 62 to 64, 71 to 75, and 138 to 149. Embodiments of amplification oligomers specific for Adenovirus nucleic acid include the amplification oligomers comprising, consisting or consisting essentially of a target hybridizing sequence selected from the group consisting of SEQ ID NOS: 1 to 9, 11 to 16, 25 to 28, 31 to 35, 38, 42 to 46, 61, 62, and 71 to 74 or a combination of two or more thereof. According to one embodiment, at least one first amplification oligomer comprises, consists of consists essentially of a target hybridizing sequence selected from the group consisting of SEQ ID NOS: 1, 5, 11, 12, 25, 26, 31, 32, 33, 34, 35, 38, 71, 72, 73, 74, or a combination of two or more thereof. According to one embodiment, at least one second amplification oligomer comprises, consists of consists essentially of a target hybridizing sequence selected from the group consisting of SEQ ID NOS: 2, 3, 6, 7, 8, 9, 13, 14, 15, 16, 27, 28, 42, 43, 44, 45, 46, 61, 62, 138, 139, 140, 141, 142, 143, 144, 145, 146, 147, 148, 149, or a combination of two or more thereof. In one embodiment, one or more of the amplification oligomers for amplifying an Adenovirus target nucleic acid comprises at least one of a 5-Me-dC, non-Watson Crick base, degenerate base, or combination thereof.

In one embodiment, one or more detection probes are configured to detect a sequence in a region corresponding to nucleotides 74 to 139 of SEQ ID NO:47; and/or nucleotides 56 to 103 of SEQ ID NO:47; and/or nucleotides 18 to 83 of SEQ ID NO:47; and/or nucleotides 23 to 83 of SEQ ID NO:47; and/or nucleotides 23 to 83 of SEQ ID NO:47; and/or nucleotides 23 to 83 of SEQ ID NO:47 and/or nucleotides 52 to 99 of SEQ ID NO:47. In one embodiment, there is provided a detection probe oligonucleotide that is from 18 to 36 nucleobases in length wherein the 18 to 36 nucleobases are all selected from contiguous nucleobases within SEQ ID NO:138.

Probes for the specific detection of Adenovirus sequences include oligomers selected from the group consisting of SEQ ID Nos. 4, 10, 17, 18, 19, 20, 21, 22, 23, 24, 29, 30, 36, 37, 39, 40, 63, 64, 139, 140 or a combination of two or more thereof. In one embodiment, one or more of the detection probe oligomers for detecting an Adenovirus target nucleic acid (including an Adenovirus amplicon) comprises at least one of a 5-Me-dC, non-Watson Crick base, degenerate base, or combination thereof.

Oligonucleotides for amplifying and/or detecting an hMPV target nucleic acid include oligonucleotide sequences that are configured to hybridize to a region of an hMPV in a region corresponding to nucleotides 966 to 1147 of SEQ ID NO:150, and/or nucleotides 844 to 1027 of SEQ ID NO:159, and/or 1000 to 1040 of SEQ ID NO:150, and/or 880 to 915 of SEQ ID NO:159, and/or 1027 to 1080 of SEQ ID NO:150, and/or 913 to 958 of SEQ ID NO:159, and/or 1073 to 1115 of SEQ ID NO:150, and/or 953 to 995 of SEQ ID NO:159. Oligonucleotides for amplifying and/or detecting an hMPV target nucleic acid include oligonucleotide sequences selected from the group consisting of SEQ ID NOS:52, 53, 56, 67 to 70, 151 to 158, and 161 to 178. Embodiments of amplification oligomers include the amplification oligomers comprising, consisting or consisting essentially of a target hybridizing sequence selected from the group consisting of SEQ ID NOS:52, 53, 56, 68, 151, 152, 153, 154, 158, 160, 177, 178, or a combination of two or more thereof. Embodiments of first amplification oligomers include the amplification oligomers comprising, consisting or consisting essentially of a target hybridizing sequence selected from the group consisting of SEQ ID NOS:52, 53, 151, 152, 153, 154, 160, or a combination of two or more thereof. Embodiments of second amplification oligomers include the amplification oligomers comprising, consisting or consisting essentially of a target hybridizing sequence selected from the group consisting of SEQ ID NOS:56, 68, 158, 177, 178, or a combination of two or more thereof. In one embodiment, one or more of the amplification oligomers for amplifying an hMPV target nucleic acid comprises at least one of a 5-Me-dC, non-Watson Crick base, degenerate base, or combination thereof.

Probes for the specific detection of hMPV sequences include oligomers selected from the group consisting of SEQ ID Nos. 67, 69, 70, 155, 156, 157, 161, 162, 163, 164, 165, 166, 167, 168, 169, 170, 171, 172, 173, 174, 175, 176, or a combination of two or more thereof. In one embodiment, there is provided a detection probe oligonucleotide that is from 18 to 36 nucleobases in length wherein the 18 to 36 nucleobases are all selected from contiguous nucleobases within SEQ ID NO:161 or within SEQ ID NO:155. In one embodiment, one or more of the detection probe oligomers for detecting an hMPV target nucleic acid (including an hMPV amplicon) comprises at least one of a 5-Me-dC, non-Watson Crick base, degenerate base, or combination thereof.

Oligonucleotides for amplifying and/or detecting an HRV target nucleic acid include oligonucleotide sequences that are configured to hybridize to a region of an HRV in a region corresponding to nucleotides 230 to 556 of SEQ ID NO:120, and/or 199 to 525 of SEQ ID NO:101, and/or 80 to 410 of SEQ ID NO:76, and/or 263 to 303 of SEQ ID NO:120, and/or 231 to 264 of SEQ ID NO:101, and/or 106 to 156 of SEQ ID NO:76, and/or 312 to 346 of SEQ ID NO:120, and/or 279 to 314 of SEQ ID NO:101, and/or 455 to 506 of SEQ ID NO:76, and/or 480 to 533 of SEQ ID NO:120, and/or 455 to 506 of SEQ ID NO:101, and/or 338 to 397 of SEQ ID NO:76. Oligonucleotides for amplifying and/or detecting an HRV target nucleic acid include oligonucleotide sequences selected from the group consisting of SEQ ID NOS:48, 49, 50, 51, 54, 57, 59, 60, 65, 75, 77 to 100, 102 to 119, 121 to 137, or a combination of two or more thereof. Embodiments of amplification oligomers include the amplification oligomers comprising, consisting or consisting essentially of a target hybridizing sequence selected from the group consisting of SEQ ID NOS:50, 51, 57, 59, 60, 65, 75, 77 to 86, 95 to 100, 102 to 108, 115 to 119, 121 to 130, 137, or a combination of two or more thereof. Embodiments of first amplification oligomers include the amplification oligomers comprising, consisting or consisting essentially of a target hybridizing sequence selected from the group consisting of SEQ ID NOS:50, 51, 59, 60, 65, 75, 77 to 86, 102 to 108, 121 to 130, or a combination of two or more thereof. Embodiments of second amplification oligomers include the amplification oligomers comprising, consisting or consisting essentially of a target hybridizing sequence selected from the group consisting of SEQ ID NOS:57, 95 to 100, 115 to 119, 137, or a combination of two or more thereof. In one embodiment, there is provided an amplification oligonucleotide that is from 18 to 29 nucleobases in length wherein the 18 to 29 nucleobases are all selected from contiguous nucleobases within SEQ ID NO:77. In one embodiment, there is provided an amplification oligonucleotide that is from 18 to 27 nucleobases in length wherein the 18 to 27 nucleobases are all selected from contiguous nucleobases within SEQ ID NO:95. In one embodiment, there is provided an amplification oligonucleotide that is from 18 to 35 nucleobases in length wherein the 18 to 35 nucleobases are all selected from contiguous nucleobases within SEQ ID NO:96. In one embodiment, there is provided an amplification oligonucleotide that is from 18 to 27 nucleobases in length wherein the 18 to 27 nucleobases are all selected from contiguous nucleobases within SEQ ID NO:115. In one embodiment, there is provided an amplification oligonucleotide that is from 18 to 27 nucleobases in length wherein the 18 to 27 nucleobases are all selected from contiguous nucleobases within SEQ ID NO:137. In one embodiment, one or more of the amplification oligomers for amplifying an HRV target nucleic acid comprises at least one of a 5-Me-dC, non-Watson Crick base, degenerate base, or combination thereof.

Probes for the specific detection of HRV sequences include oligomers selected from the group consisting of SEQ ID Nos. 48, 49, 54, 87 to 94, 109 to 114, 131 to 136, or a combination of two or more thereof. In one embodiment, one or more of the detection probe oligomers for detecting an HRV target nucleic acid (including an HRV amplicon) comprises at least one of a 5-Me-dC, non-Watson Crick base, degenerate base, or combination thereof.

Assays for detection of Adeno, hMPV, and/or HRV nucleic acid may include an internal control (IC) nucleic acid that is amplified and detected by using IC-specific primers and probe in the same reaction mixtures used for target nucleic acid amplification and detection. Amplification and detection of the IC-specific sequence demonstrates that assay reagents and conditions were properly used even when no target-specific signal is detected for a tested sample (i.e., negative samples). The IC may be used as an internal calibrator for the assay that provides a quantitative result. The IC may be a randomized sequence derived from a naturally occurring source that is not a target nucleic acid.

Sample Preparation

Preparation of samples for amplification and detection of target nucleic acid sequences may include methods of separating and/or concentrating organisms contained in a sample from other sample components. Sample preparation may include routine methods of disrupting samples or lysing samples to release intracellular contents, including target nucleic acids or genetic sequences comprising target nucleic acid. Sample preparation before amplification may include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, other methods of physically separating nucleic acids from a mixture that contains Adenovirus nucleic acid and other sample components.

Amplification of the Adenovirus Target Region

Amplifying a target nucleic acid target region using two or more primers may be accomplished using a variety of known nucleic acid amplification reactions. For example, amplification may be achieved using PCR amplification (U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well known variations of the basic PCR method may also be used, e.g., PCR coupled with real-time detection—such as TAQMAN™ PCR.

Nucleic Aid Detection

Detection of the nucleic acids may be accomplished by a variety of methods. Detection methods may use nucleic acid probes comprising a target hybridizing sequence that is complementary to a portion of the amplified product and detecting the presence of the probe: product complex, or by using a complex of probes that may amplify the detectable signal associated with the amplified products (e.g., U.S. Pat. Nos. 5,424,413; 5,451,503; 5,849,481; 5,639,604 and 5,283,174). Directly or indirectly labeled probes that specifically associate with the amplified product provide a detectable signal that indicates the presence of the target nucleic acid in the sample. For example, if the target nucleic acid is Adenovirus DNA, the amplified product will contain a sequence in or complementary to an Adenovirus target sequence. A probe is configured to bind directly or indirectly to a portion of the amplification product to indicate the presence of Adenovirus in the tested sample.

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes are described, e.g., in U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1).

Homogeneously detectable labels, such as fluorescent labels and electronically detectable labels, are intended for use in the practice of the present disclosure. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred, hi addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other, wherein fluorescent emission from a fluorophore attached to one portion of the probe is quenched by a quencher moiety on another portion of the probe (e.g., "Taqman" detection probe chemistry). Label moieties for the Taqman probes include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a detection probe having a pair of interactive labels in the "quenched" state is stimulated by an appropriate frequency of light, a fluorescent signal is generated at a first level, which may be very low. When this same probe is in an "unquenched" state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Examples of fluorophore/quencher label pairs that may be used in connection with the disclosure, include fluorescein/tetramethylrhodamine, IAEDANS/fluororescein, EDANS/DABCYL, coumarin/D ABCYL, fluorescein/fluorescein, BODIPY FL/JBODIPY FL, fluorescein/D ABCYL, lucifer yellow/D ABCYL, BODIPY/D ABCYL, eosine/D ABCYL, erythrosine/D ABCYL, tetramethylrhodamine/D ABCYL, CalOrange/BHQ1, CalRed/BHQ2, Texas Red/DABCYL, CY5/BH1, CY5/BH2, CY3/BH1, CY3/BH2, fluorescein/QSY7, FAM/BHQ1 and Quasar/BHQ2. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation.

Synthetic techniques and methods of bonding labels to nucleic acids and detecting labels are well known in the art (e.g., see Sambrook et al., Molecular Cloning. A Laboratory Manual. 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Kits

The oligomers for use in the methods described herein are suited for preparation of kits. Such a kit may comprise containers, each with one or more of the various oligomers optionally together with one or more of the reagents (eg. enzymes) required to perform the methods described herein. The components of the kit may be supplied in concentrated form. A set of instructions for using the components of the kit will also typically be included. Where the kit comprises combinations of oligomers then the individual oligomers may be provided in individual form, with appropriate instructions for mixing same, or combinations thereof that are ready mixed.

In one aspect, there is provided a kit comprising the composition of the present disclosure and optionally a set of instructions for performing same.

Correlation of Detection of a Target Sequence with Diagnosis

The detection of amplified target sequences characteristic of Adenovirus, Metapneumovirus, and/or Rhinovirus in a biological sample from an individual is indicative, respectively, of infection by Adenovirus, Metapneumovirus, and/or Rhinovirus.

EXAMPLES

Example 1: Analysis of Certain Adenovirus Amplification Primers and Probes

Materials & Methods

In a first amplification reaction, the following was used: FAST START™ Master Buffer (Roche) at 1× to 2× concentration, 2 Units of FAST START™ Taq DNA polymerase (Roche), 100 nM of a forward amplification primer (SEQ ID No. 5) and 100 nM of a reverse amplification primer (SEQ ID No. 6 or SEQ ID No. 8) and 100 nM probe (SEQ ID No. 10).

The total reaction volume was 20 microlitres with 5 microlitres of template nucleic acid extracted from Adenovirus added per reaction. Control reactions were performed by setting up a reaction as described above but not adding any template nucleic acids. The amplification cycles used were as follows for both sets of amplification reactions: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 1

Adenovirus Amplification and Detection with Primer and Probe Sets

| | SEQ ID Nos. 5, 6 and 10 | | SEQ ID Nos. 5, 8 and 10 | |
|---|---|---|---|---|
| | $C_T$ | RFU | $C_T$ | RFU |
| Target/Sample | 26.9 | 519 | 26.4 | 383 |

The results are presented as $C_T$/RFU (cycle threshold/relative fluorescent unit) values and represent the average of 12 experiments using various Adenovirus serotypes. Amplification was not seen in any of the control reactions.

Conclusion

The primers and probes used appeared to be sensitive and specific for Adenovirus nucleic acid.

Example 2: Analysis of Further Certain Adenovirus Amplification Primers and Probes Materials & Methods The following reagents were used: FAST START™ Master Buffer (Roche) at 1× to 2× concentration, 2 Units of FAST START™ Taq DNA polymerase (Roche), 200 nM of a forward amplification primer (SEQ ID No. 11 or SEQ ID No. 12) and 200 nM of a reverse amplification primer (SEQ ID No. 13 or SEQ ID No: 15) and 200 nM probe (SEQ ID No. 17 or SEQ ID No. 19).

The total reaction volume was 20 microlitres with 5 microlitres of template nucleic acid extracted from Adenovirus added per reaction. Control reactions were performed by setting up a reaction as described above but not adding any template nucleic acids. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 2

Adenovirus Amplification and Detection with Primer and Probe Sets

| | SEQ ID Nos. 11, 13 and 17 | | SEQ ID Nos. 11, 13 and 19 | |
|---|---|---|---|---|
| | $C_T$ | RFU | $C_T$ | RFU |
| Target/Sample | 8.7 | 29.8 | 32 | 460 |
| | SEQ ID Nos. 11, 15 and 17 | | SEQ ID Nos. 11, 15 and 19 | |
| | $C_T$ | RFU | $C_T$ | RFU |
| Target/Sample | 13.3 | 29.5 | 32.3 | 406.4 |
| | SEQ ID Nos. 12, 15 and 19 | | SEQ ID Nos. 12, 15 and 17 | |
| | $C_T$ | RFU | $C_T$ | RFU |
| Target/Sample | 29.6 | 620 | 12.6 | 32.8 |
| | SEQ ID Nos. 12, 13 and 19 | | SEQ ID Nos. 12, 13 and 17 | |
| | $C_T$ | RFU | $C_T$ | RFU |
| Target/Sample | 29.6 | 504 | 8.3 | 18.9 |

The results are presented as $C_T$/RFU values and represent the average of 8 experiments using various Adenovirus serotypes. Amplification was not seen in any of the control reactions.

Conclusion

Combinations of SEQ ID Nos. 11, 13 and 19, SEQ ID Nos. 11, 15 and 19, SEQ ID Nos. 12, 15 and 19 or SEQ ID Nos. 12, 13 and 19 were sensitive and specific for Adenovirus nucleic acid. The combinations comprising the SEQ ID No. 12 forward primer appears to have better sensitivity than the combination comprising the SEQ ID No. 11 forward primer. The combination comprising SEQ ID Nos. 12, 15 and 19 appeared to be most sensitive in these experiments.

Example 3: Adenovirus Serotyne Analysis Using SEQ ID Nos. 12. 15 and 19

Materials & Methods

The following reagents were used: FAST START™ Master Buffer (Roche) at 1× concentration, 2 Units of FAST START™ Taq DNA polymerase (Roche), 400 nM of a forward amplification primer (SEQ ID No. 12) and 400 nM of a reverse amplification primer (SEQ ID No. 15) was used together with 400 nM probe (SEQ ID No. 19). The total reaction volume was 20 microlitres with 5 microlitres of template nucleic acid extracted from Adenovirus added per reaction. Control reactions were set-up, but no template nucleic acid was added. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 3

Adenovirus Serotype Analysis

| Serotype | $C_T$ | RFU |
|---|---|---|
| 2-1 | 26 | 1203 |
| 4-1 | 31 | 666 |

TABLE 3-continued

Adenovirus Serotype Analysis

| Serotype | $C_T$ | RFU |
|---|---|---|
| 6-1 | 29 | 926 |
| 7-1 | 32 | 605 |
| 9-1 | 26 | 1137 |
| 10-1 | 28 | 1252 |
| 11-1 | 28 | 630 |
| 12-1 | 26 | 1119 |
| 13-1 | 26 | 1100 |
| 14-1 | 30 | 682 |
| 15-1 | 26 | 1078 |
| 16-1 | 29 | 723 |
| 17-1 | 23 | 1100 |
| 18-1 | 34 | 387 |
| 19-1 | 27 | 1146 |
| 20-1 | 23 | 996 |
| 21-1 | 31 | 568 |
| 22-1 | 25 | 1044 |
| 23-1 | 23 | 1109 |
| 24-1 | 25 | 1221 |
| 25-1 | 32 | 836 |
| 26-1 | 24 | 1107 |
| 27-1 | 25 | 1070 |
| 28-1 | 26 | 989 |
| 29-1 | 27 | 1116 |
| 30-1 | 22 | 1166 |
| 31-1 | 21 | 1127 |
| 33-1 | 28 | 941 |
| 34-1 | 28 | 654 |
| 35-1 | 29 | 542 |
| 36-1 | 24 | 997 |
| 37-1 | 24 | 1125 |
| 38-1 | 26 | 1033 |
| 39-1 | 23 | 1143 |
| 40-1 | 27 | 1114 |
| 41-1 | 25 | 994 |
| 42-1 | 23 | 1125 |
| 43-1 | 22 | 1149 |
| 44-1 | 22 | 1141 |
| 45-1 | 27 | 1071 |
| 46-1 | 27 | 1047 |
| 47-1 | 22 | 1144 |
| 48-1 | 25 | 1174 |
| 49-1 | 26 | 1068 |
| 50-1 | 25 | 672 |
| 51-1 | 26 | 1099 |
| 1-1 | 29 | 956 |
| 3-1 | 32 | 540 |
| 5-1 | 29 | 791 |
| 7A-1 | 26 | 632 |
| 8-1 | 34 | 553 |
| 32-2 | 24 | 974 |

The Serotype column is set-up to reflect "serotype number-1×10$^v$TCID$_{50}$/mL." $C_T$ values have all been rounded down. The results are presented as $C_T$/RFU values.

Conclusion

The combination of SEQ ID Nos. 12, 15 and 19 was able to detect all serotypes of Adenovirus that were tested.

Example 4: Analysis of Further Adenovirus Probe Combinations Together with SEQ ID NOS: 12 and 15 Primers Materials & Methods The following were reagents used: FAST START™ Master Buffer (Roche) at 1× concentration, 2 Units of FAST START™ Taq DNA polymerase (Roche), 100 nM of a forward amplification primer (SEQ ID No. 12) and 100 nM of a reverse amplification primer (SEQ ID No. 15) was used together with either: 150 nM probe (SEQ ID No. 21) and 50 nM probe (SEQ ID No. 24); 100 nM probe (SEQ ID No. 21) and 100 nM probe (SEQ ID No. 24); 50 nM probe (SEQ ID No. 21) and 150 nM probe (SEQ ID No. 24). The total reaction volume was 20 microlitres with 5 microlitres of template nucleic acid extracted from Adenovirus added per reaction. Control reactions were set-up without the addition of template nucleic acid. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 4

Amplification and detection using different concentrations of probe combinations

| | 150 nM SEQ ID No. 21 and 50 nM SEQ ID No. 24; | | 100 nM SEQ ID No. 21 and 100 nM SEQ ID No. 24; | |
|---|---|---|---|---|
| | $C_T$ | RFU | $C_T$ | RFU |
| Target | 34.8 | 291 | 26.9 | 318 |

| | 50 nM SEQ ID No. 21 and 150 nM SEQ ID No. 24 | |
|---|---|---|
| | $C_T$ | RFU |
| Target | 26.8 | 339 |

The results are presented as $C_T$/RFU values and represent the average of 6 experiments using various Adenovirus serotypes.

Conclusion

SEQ ID No. 21 and ID No. 24 probes in combination with SEQ ID No. 12 and 15 were able to sensitively and specifically detect Adenovirus at the various concentrations tested.

Example 5: Analysis of Further Probe and Primer Combinations for the Detection of Adenovirus Materials & Methods FAST START™ Master Buffer (Roche) at 1× concentration, 2 Units of FAST START™ Taq DNA polymerase (Roche) and either: (i) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21 and SEQ ID No. 23); (ii) 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21 and SEQ ID No. 23); (iii) 50 mM of a forward amplification primer (SEQ ID No. 25), 50 mM of a reverse amplification primer (SEQ ID No. 27), 50 mM of a reverse amplification primer (SEQ ID No. 28) and 100 nM of probes (SEQ ID No. 21 and SEQ ID No. 23); (iv) 50 mM of a forward amplification primer (SEQ ID No. 25), 50 mM of a forward amplification primer (SEQ ID No. 26), 50 mM of a reverse amplification primer (SEQ ID No. 28) and 100 nM of probes (SEQ ID No. 21 and SEQ ID No. 23); (v) 50 mM of a forward amplification primer (SEQ ID No. 25), 50 mM of a forward amplification primer (SEQ ID No. 26), 50 mM of a reverse amplification primer (SEQ ID No. 28) and 100 nM of probes (SEQ ID No. 21 and SEQ ID No. 23); (vi) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probe (SEQ ID No. 23); or (vii) 50 mM of a forward amplification primer (SEQ ID No. 25), 50 mM of a forward amplification primer (SEQ ID No. 26), 50 mM of a reverse amplification primer (SEQ ID No. 27), 50 mM of a reverse amplification primer (SEQ ID No. 28) and 100 nM of probes (SEQ ID No. 21).

The total reaction volume was 20 microlitres with 5 microlitres of template nucleic acid extracted from Adenovirus added per reaction. Two different concentrations were tested.

The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

Tables 5a-5d. Amplification and detection using different concentrations and combinations of primers and probes.

TABLE 5a

| | SEQ ID Nos. 25, 26, 27, 28, 21 and 23 | | SEQ ID Nos. 26, 27, 28, 21 and 23 | |
|---|---|---|---|---|
| | $C_T$ | RFU | $C_T$ | RFU |
| Target($10^1$) | 38.5 | 240 | 39.2 | 143 |
| Target($10^3$) | 29.8 | 373 | 30.8 | 227 |

TABLE 5b

| | SEQ ID Nos. 25, 27, 28, 21 and 23 | | SEQ ID Nos. 25, 26, 28, 21 and 23 | |
|---|---|---|---|---|
| | $C_T$ | RFU | $C_T$ | RFU |
| Target($10^1$) | 37.8 | 212 | 41.5 | 99 |
| Target($10^3$) | 30.2 | 275 | 32 | 258 |

TABLE 5c

| | SEQ ID Nos. 25, 26, 27, 21 and 23 | | SEQ ID Nos. 25, 26, 27, 28 and 23 | |
|---|---|---|---|---|
| | $C_T$ | RFU | $C_T$ | RFU |
| Target($10^1$) | 41.8 | 96 | 37.7 | 254 |
| Target($10^3$) | 31.8 | 320 | 30 | 360 |

TABLE 5d

| | SEQ ID Nos. 25, 26, 27, 28 and 21 | |
|---|---|---|
| | $C_T$ | RFU |
| Target($10^1$) | 7.1 | 21 |
| Target($10^3$) | 0 | 3 |

The results are presented as RFU values and represent the average of 6 experiments for each concentration.

Conclusion

Leaving out one of the primers or probes from the assay made little difference for the most part. However, omitting probe SEQ ID No. 23 resulted in lower detection in this particular experiment.

Example 6: Analysis of Primer and Probe Combinations for Detecting Adenovirus 18

Materials & Methods

The following reagents were used: FAST START™ Master Buffer (Roche) at 1× concentration, 3 Units of FAST START™ Taq DNA polymerase (Roche), 150 nM forward amplification primers (SEQ ID No. 25 and SEQ ID No. 26) and 150 nM reverse amplification primers (SEQ ID No. 27 and SEQ ID No. 28) were used together with 300 nM probe (SEQ ID No. 29). The total reaction volume was 20 microlitres with 5 microlitres of template nucleic acid extracted from Adenovirus 18 added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 6

Amplification and detection of Adenovirus 18.

| Serotype | $C_T$ | RFU |
|---|---|---|
| 18-6 | 17 | 1240 |
| 18-5 | 20 | 975 |
| 18-4 | 24 | 1242 |
| 18-3 | 30 | 1023 |
| 18-2 | 33 | 942 |
| 18-1 | 35 | 747 |
| 18-0 | 31 | 1215 |

The Serotype column is set-up to reflect "serotype number-$1\times10^x$ TCID$_{50}$/mL." $C_T$ values have all been rounded down. The results are presented as $C_T$/RFU values.

Conclusion

This combination of primers and probes successfully detects Adenovirus 18.

Example 7: Analysis of Further Primer and Probe Combinations for Detecting Adenovirus Materials & Methods The following reagents were used: FAST START™ Master Buffer (Roche) at 1× concentration, 3 Units of FAST START™ Taq DNA polymerase (Roche), 150 nM forward amplification primers (SEQ ID No. 31 and SEQ ID No. 26) and 150 nM reverse amplification primers (SEQ ID No. 27 and SEQ ID No. 28) were used together with 150 nM probe (SEQ ID No. 21 and SEQ ID No. 23). The total reaction volume was 20 microlitres with 5 microlitres of template nucleic acid extracted from various Adenovirus serotypes added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 7

Primer and probe combinations for detecting various Adenovirus serotypes.

| Serotype | FAM | | Cy5 | |
|---|---|---|---|---|
| | $C_T$ | RFU | $C_T$ | RFU |
| 1 | 38.7 | 40 | 35.9 | 172 |
| 3 | 37.4 | 59 | 35.5 | 208 |
| 4 | 0 | 22 | 37.2 | 185 |
| 7 | 32.2 | 711 | 32 | 209 |
| 11 | 24.2 | 843 | 32.2 | 190 |
| 14 | 28.8 | 737 | 31.9 | 196 |
| 16 | 23.8 | 879 | 32.1 | 212 |
| 21 | 31.9 | 671 | 31.4 | 219 |
| 25 | 32.8 | 399 | 31.7 | 217 |
| 34 | 29.3 | 645 | 31.7 | 205 |
| 35 | 29.6 | 771 | 30.7 | 220 |
| 50 | 24.6 | 786 | 30.9 | 210 |

The results are presented as $C_T$/RFU values. The Fam-channel shows detection results for the template nucleic acids. The Cy5-channel shows detection results for an internal control nucleic acid.

Conclusion

With the exception of serotype 4, this combination of primers and probes successfully detected all of the serotypes tested.

Example 8: Analysis of Further Primer and Probe Combinations for Detecting Adenovirus Materials & Methods The following reagents were used: FAST START™ Master Buffer (Roche) at 1× concentration, 3 Units of FAST START™ Taq DNA polymerase (Roche) and either: (i) 150 nM forward amplification primers (SEQ ID Nos. 33 and 34) and 150 nM reverse amplification primers (SEQ ID No. 27 and SEQ ID No. 28) were used together with 150 nM probe (SEQ ID No. 21 and SEQ ID No. 23); (ii) 150 nM forward amplification primers (SEQ ID Nos. 33 and 35) and 150 nM reverse amplification primers (SEQ ID No. 27 and SEQ ID No. 28) were used together with 150 nM probe (SEQ ID No. 21 and SEQ ID No. 23); or (iii) 150 nM forward amplification primers (SEQ ID Nos. 34 and 35) and 150 nM reverse amplification primers (SEQ ID No. 27 and SEQ ID No. 28) were used together with 150 nM probe (SEQ ID No. 21 and SEQ ID No. 23). The total reaction volume was 20 microlitres with 5 microlitres of template nucleic acid extracted from various Adenovirus serotypes added per reaction. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

Tables 8a-8c. Amplification and detection of various Adenovirus serotypes using combinations of primers and probes.

TABLE 8a

SEQ ID Nos. 33, 34, 27, 28, 21 and 23

| Serotype | FAM | | Cy5 | |
|---|---|---|---|---|
| | $C_T$ | RFU | $C_T$ | RFU |
| 1 | 35.6 | 318 | 35.9 | 243 |
| 3 | 37.3 | 87 | 35.8 | 210 |
| 4 | 36.9 | 150 | 35.6 | 232 |
| 19 | 38.1 | 95 | 35.2 | 217 |
| 31 | 35.7 | 247 | 34.6 | 257 |
| 41 | 36.7 | 244 | 35.9 | 285 |
| 14 | 29.7 | 868 | 31.5 | 250 |

TABLE 8b

SEQ ID Nos. 33, 35, 27, 28, 21 and 23

| Serotype | FAM | | Cy5 | |
|---|---|---|---|---|
| | $C_T$ | RFU | $C_T$ | RFU |
| 1 | 0 | 12 | 35.7 | 248 |
| 3 | 36.4 | 159 | 35.1 | 231 |
| 4 | 36.8 | 171 | 35.6 | 249 |
| 19 | 36.7 | 151 | 35.3 | 181 |
| 31 | 35.8 | 170 | 34.6 | 197 |
| 41 | 39.3 | 50 | 36 | 243 |
| 14 | 29.2 | 1062 | 31.5 | 256 |

TABLE 8c

SEQ ID Nos. 34, 35, 27, 28, 21 and 23

| Serotype | FAM | | Cy5 | |
|---|---|---|---|---|
| | $C_T$ | RFU | $C_T$ | RFU |
| 1 | 37.5 | 198 | 35.5 | 199 |
| 3 | 0 | 5 | 35.5 | 213 |
| 4 | 0 | 15 | 36.1 | 158 |
| 19 | 0 | 12 | 35.1 | 224 |
| 31 | 35.6 | 369 | 34.6 | 240 |
| 41 | 36.6 | 284 | 35.7 | 263 |
| 14 | 33.1 | 942 | 32.1 | 203 |

The results are presented as $C_T$ and RFU values. The Fam-channel shows detection results for the template nucleic acids. The Cy5-channel shows detection results for an internal control nucleic acid.

Conclusion

Table 8a of primers and probes successfully detected all of the serotypes tested. Tables 8b and 8c detected most serotypes tested.

Example 9: Analysis of Further Primer and Probe Combinations for Detecting Adenovirus Materials & Methods The following reagents were used: FAST START™ Master Buffer (Roche) at 1× concentration, 3 Units of FAST START™ Taq DNA polymerase (Roche) and 150 nM forward amplification primers (SEQ ID Nos. 25 and 26) and 150 nM reverse amplification primers (SEQ ID No. 27 and SEQ ID No. 28) were used together with 150 nM probe (SEQ ID No. 36 and SEQ ID No. 37). The total reaction volume was 20 microlitres with 5 microlitres of template nucleic acid extracted from the Adenovirus 19 serotype positive control plasmid, which added per reaction at six different concentrations. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 9

Amplification and detection of a serial dilution of target nucleic acid

| Concentration | FAM | |
|---|---|---|
| | $C_T$ | RFU |
| $10^4$ | 28.1 | 1127 |
| $10^4$ | 28.2 | 1040 |
| $10^4$ | 28 | 1196 |
| $10^3$ | 31.9 | 938 |
| $10^3$ | 32.1 | 922 |
| $10^3$ | 32.3 | 969 |
| $10^2$ | 35.3 | 865 |
| $10^2$ | 35.4 | 800 |
| $10^2$ | 35.2 | 800 |
| $10^1$ | 37.8 | 571 |
| $10^1$ | 33.6 | 59 |
| $10^1$ | 38.6 | 419 |
| $10^0$ | 0 | 10 |
| $10^0$ | 0 | 0 |
| $10^0$ | 0 | 0 |
| $10^{-1}$ | 0 | 0 |
| $10^{-1}$ | 0 | 0 |
| $10^{-1}$ | 0 | 0 |

The results are presented as $C_T$/RFU values.

Conclusion

These primers and probes successfully detected the control tested Adenovirus 19 serotype.

Example 10: Further Analysis of the Primer and Probe Combination from Example 9

Materials & Methods

The following reagents were used: FAST START™ Master Buffer (Roche) at 1× concentration, 3 Units of FAST START™ Taq DNA polymerase (Roche) and 150 nM forward amplification primers (SEQ ID Nos. 25 and 26) and 150 nM reverse amplification primers (SEQ ID No. 27 and SEQ ID No. 28) were used together with 150 nM probe (SEQ ID No. 36 and SEQ ID No. 37). The total reaction volume was 20 microlitres with 5 microlitres of template nucleic acid extracted from various Adenovirus serotypes and tested at a concentration of $3 \times 10^0$. The amplification cycles used were as follows: Hold for 600 seconds at 95 deg. C. with optics off; 95 deg. C. for 30 seconds with optics off and 55 deg. C. for 60 seconds with optics on (5 cycles); 95 deg. C. for 10 seconds with optics off and 55 deg. C. for 60 seconds (40 cycles) with optics on.

Results

TABLE 10

Amplification and detection of Adenovirus target nucleic acids

| Serotype | $C_T$ | RFU |
|---|---|---|
| 2 | 31.6 | 1465 |
| 5 | 33.9 | 903 |
| 6 | 0 | 0 |
| 7 | 39 | 366 |
| 8 | 37.4 | 625 |
| 9 | 32 | 1223 |
| 10 | 36.3 | 837 |
| 11 | 26.6 | 950 |
| 12 | 31.8 | 1176 |
| 13 | 29.7 | 1487 |
| 14 | 34 | 671 |
| 15 | 33.5 | 1018 |
| 16 | 33.4 | 729 |
| 17 | 30.2 | 1622 |
| 18 | 40 | 175 |
| 20 | 27.2 | 1217 |
| 21 | 34.1 | 733 |
| 22 | 31.2 | 1150 |
| 23 | 30.1 | 1471 |
| 24 | 33.2 | 1110 |
| 25 | 37.3 | 661 |
| 26 | 29.1 | 1814 |
| 27 | 29.5 | 1637 |
| 28 | 34.2 | 1032 |
| 29 | 32.9 | 1159 |
| 30 | 28.4 | 1496 |
| 32 | 26.6 | 2079 |
| 33 | 33.9 | 1017 |
| 34 | 34.2 | 690 |
| 35 | 33.1 | 702 |
| 36 | 29.1 | 1312 |
| 37 | 30.2 | 1393 |
| 38 | 31.8 | 1202 |
| 39 | 30 | 1650 |
| 40 | 32.6 | 1290 |
| 42 | 29.1 | 1261 |
| 43 | 28.8 | 1832 |
| 44 | 23.3 | 1218 |
| 45 | 32.1 | 1289 |
| 46 | 32.5 | 1183 |
| 47 | 26.4 | 1209 |
| 48 | 29.4 | 1565 |
| 49 | 31.5 | 1264 |
| 50 | 32 | 846 |
| 51 | 31.4 | 1125 |

The results are presented as $C_T$ and RFU values.

Discussion

All of the serotypes tested were detected using this primer and probe concentration with the exception of serotype 6. This serotype was successfully detected at $3 \times 10^1 TCID_{50}$/mL and above.

Example 11. Multiplex Amplification and Detection of Adenovirus and Human Metapneumovirus and Rhinovirus Materials & Methods Analytical Sensitivity and Reactivity: A PCR formulation containing primers and probes for the amplification and detection of Adenovirus, human Metapneumovirus, and Rhinovirus was prepared to include (per reaction): 15 uL of Supermix (11.1 Units Taq); 1.2 uL of MMLV reverse transcriptase (RT) (24 Units); 2.0 uL of Primer Probe Mix; 0.084 uL of 0.5M EDTA; and 1.716 uL of Water. (AMR formulation.) Target nucleic acids were extracted from a number of stock organisms[1] and diluted to 0.1 $TCID_{50}$/mL, 1 $TCID_{50}$/mL and 10 $TCID_{50}$/mL for each organism. 10 uL of target nucleic acid elute from each dilution was individually combined with a reaction volume of the PCR formulation for a 30 uL total reaction volume. Primers and probes used in this experiment are shown in SEQ ID NOs:48-49, & 51-74, which include internal controls. Probes used in this example were dual labelled probes comprising quenchers and fluorophores.

[1]Target nucleic acids were isolated from previously characterized stock organisms obtained from TriCore Reference Laboratories (Albuquerque, NM); ZeptoMetrix Corporation (Buffalo, NY); and ATCC (Manassas, VA).

A multiplex, real-time PCR reaction was set up using the Panther PANTHER® instrument (Hologic, Inc., San Diego, CA) for sample preparation and the benchtop PCR thermocycler for real-time amplification and detection. Detection reactions used TAQMAN™ (Roche Molecular Systems, Inc., Pleasanton, CA) chemistry. Adenovirus target nucleic acids were detected in a ROX channel, hMPV nucleic acids were detected in a HEX channel, HRV nucleic acids were detected in a FAM channel, and the internal control was detected in a RED677 channel of the thermocycler. The assay was performed using 10 replicates of each viral target at the known concentrations. Each individual sample preparation was evaluated as one real time RT-PCR replicate on a benchtop PCR thermocycler. Positive or negative determinations were made using background subtracted curves. Table 11 thru Table 13 demonstrate 100% hit rate at viral concentrations at or below 10 $TCID_{50}$/mL.

Subsequent to these studies, two additional bases were added to the 5' end of primer SEQ ID NO:75 to generate primer SEQ ID NO:50. A Rhinovirus sensitivity assay was performed as above with SEQ ID NO:50 in place of SEQ ID NO:75 and the results are presented in Table 14.

TABLE 11

Rhinovirus detection using AdV/hMPV/RV combined oligonucleotide formulation

| Rhinovirus | Concentration (TCID50/ml) | Percent Hit Rate (n = 10) | Avg Ct | StDev Ct | RFU | StDev RFU |
|---|---|---|---|---|---|---|
| Rhinovirus A-18 | $10^0$ | 100% | 34.2 | 0.4 | 14828 | 4048 |
| Rhinovirus B-26 | $10^0$ | 100% | 35.1 | 0.4 | 4641 | 662 |

TABLE 12 hMPV detection using AdV/hMPV/RV combined oligonucleotide formulation

| hMPV | Concentration (TCID50/ml) | Percent Hit Rate (n = 10) | Avg Ct | StDev Ct | RFU | StDev RFU |
|---|---|---|---|---|---|---|
| hMPV A1-16 | $10^1$ | 100% | 37.7 | 0.6 | 3019 | 630 |
| hMPV A2-20 | $10^1$ | 100% | 34.8 | 0.3 | 6186 | 583 |
| hMPV B1-3 | $10^1$ | 100% | 35.8 | 1.0 | 5818 | 1357 |
| hMPV B2-8 | $10^1$ | 100% | 34.1 | 0.4 | 8043 | 1206 |

TABLE 13

Adenovirus detection using AdV/hMPV/RV combined oligonucleotide formulation

| Adenovirus | Concentration (TCID50/ml) | Percent Hit Rate (n = 10) | Avg Ct | StDev Ct | RFU | StDev RFU |
|---|---|---|---|---|---|---|
| AdV 1 (Species C) | $10^{-1}$ | 100% | 38.1 | 0.8 | 2919 | 921 |
| AdV 3 (Species B) | $10^0$ | 100% | 36.1 | 0.3 | 5809 | 1157 |
| AdV 4 (Species E) | $10^{-3}$ | 100% | 37.9 | 1.9 | 2738 | 965 |
| AdV 9 (Species D) | $10^{-1}$ | 100% | 37.6 | 0.7 | 2786 | 831 |
| AdV 12 (Species A) | $10^{-1}$ | 100% | 36.4 | 0.8 | 2186 | 549 |
| AdV 40 (Species F) | $10^0$ | 100% | 38.5 | 1.4 | 2320 | 1184 |

TABLE 14

Rhinovirus B detection using AdV/hMPV/RV combined oligonucleotide formulation containing SEQ ID NO: 74

| Rhinovirus | Concentration (TCID50/ml) | Percent Hit Rate (n = 10) | Avg Ct | StDev Ct | RFU | StDev RFU |
|---|---|---|---|---|---|---|
| Rhinovirus B-26 | $10^0$ | 100% | 36.4 | 0.3 | 7509 | 1459 |

Conclusion

A multiplexed combination of the amplification and detection oligonucleotides presented in this review is capable of detecting viral concentrations at or below 10 $TCID_{50}$/mL.

Example 12. Clinical Specimen Detection and Clinical Specificity Using a Multiplexed Amplification and Detection Assay Materials & Methods PCR formulations (AMR formulation) containing all of the primers and probes listed above in Example 11 (using SEQ ID NO:74) were used to test clinical specimens that had been identified to be Rhinovirus positive, hMPV positive, and/or Adenovirus positive or negative for all three viruses by a commercial assay. The commercial assays include the BioFire FILMARRAY™ RVP Respiratory Panel (BioFire Diagnostics, Salt Lake City, UT), the GenMark eSENSOR™ Respiratory Virus Panel (RVP) (GenMark Diagnostics, Inc., Carlsbad, CA), and the Luminex xTAG™ Respiratory Virus Panel (Luminex Corporation, Austin, TX). All samples were extracted using the PANTHER® instrument (Hologic, Inc.) and PCR cycling was performed on a benchtop PCR thermocycler instrument as described above. The AMR assay detected HRV, hMPV, and Adenovirus in these previously characterized clinical specimens with a concordance of 94.8% (164/173) for HRV, 97.2% (279/287) for hMPV, and 93.2% (466/500) for Adenovirus. The AMR assay identified 86 of 88 clinical specimen as negative, providing a 97.7% concordance with the reference assay (Luminex xTAG™ Respiratory Virus Panel). In addition the internal control was valid for all clinically negative specimens. The two 'false positive' results received using the AMR formulation assay were determined to be true positives using the GenMark eSENSOR™ RVP assay and the Prodesse PROADENO+™ Assay (Hologic, Inc., San Diego, CA). Thus, removing the clinical specimen falsely identified as negative by the Luminex assay indicated a 100% concordance by the AMR assay (86/86).

Conclusion

A multiplexed combination of the amplification and detection oligonucleotides presented in this example is capable of detecting viral targets in clinical specimens and demonstrates good concordance with competitor assays.

Specificity

Materials & Methods

A PCR formulation (AMR formulation) containing all of the primers and probes listed in Example 11 (using SEQ ID NO:74) were evaluated for cross reactivity with other organisms. These organisms are those commonly found in specimen type (nasopharyngeal and lower respiratory specimens) that are tested in the clinic for the presence or absence of one or more of Adenovirus, hMPV and HRV. Organisms were either pooled and tested or tested individually (see, AMR panels 1 thru 26 in Table 15). Three replicates from each panel were individually processed on the PANTHER® instrument (Hologic, Inc.) and PCR cycling was performed on a benchtop PCR thermocycler instrument as described above. Table 15 demonstrates that only viruses targeted by the AMR formulation (AMR 24-26) were detected. Cross-reactivity with organisms not targeted by the assay (AMR 1-23) was not observed.

TABLE 15

Organisms and concentrations of the AMR formulation specificity panel[2]

| Panel | Organism | Test Concentration | Cross-Reactivity Results |
|---|---|---|---|
| AMR 1 | *Acinetobacter baumannii* 307-0294 | $1 \times 10^{\wedge}7.6$ CFU/ml | Not observed |
| | Comavirus 229E | $1 \times 10^{\wedge}4.0$ TCID50/ml | Not observed |
| | *Bordetella parapertussis* | $1 \times 10^{\wedge}7.2$ CFU/ml | Not observed |
| | *Burkholderia cepacia* Z066 | $1 \times 10^{\wedge}8.0$ CFU/ml | Not observed |
| | *Candida albicans* Z006 | $1 \times 10^{\wedge}6.5$ CFU/ml | Not observed |
| | *Chlamydia pneumoniae* | $1 \times 10^{\wedge}5.8$ CFU/ml | Not observed |
| AMR 2 | *Bordetella pertussis* | $1 \times 10^{\wedge}7.6$ CFU/ml | Not observed |
| | *Candida glabrata* Z007 | $1 \times 10^{\wedge}6.9$ CFU/ml | Not observed |
| | *Chlamydia trachomatis* | $1 \times 10^{\wedge}5.8$ CFU/ml | Not observed |
| | *Corynebacterium diphtheriae* Z116 | $1 \times 10^{\wedge}7.9$ CFU/ml | Not observed |
| | Comavirus NL63 | $1 \times 10^{\wedge}3.5$ TCID50/ml | Not observed |
| | Cytomegalovirus AD-169, MRC-5 | $1 \times 10^{\wedge}3.9$ TCID50/ml | Not observed |
| AMR 3 | *E. coli* ETEC; ST+, LT+ | $1 \times 10^{\wedge}7.8$ CFU/ml | Not observed |
| | HPIV-1 | $1 \times 10^{\wedge}3.7$ TCID50/ml | Not observed |
| | HSV-1 Macinytre Strain | $1 \times 10^{\wedge}5.8$ TCID50/ml | Not observed |
| | Cornavirus OC43 | $1 \times 10^{\wedge}5.3$ TCID50/ml | Not observed |
| | IA/California/07/2009 2009 H1N1 | $1 \times 10^{\wedge}3.5$ TCID50/ml | Not observed |
| | *Lactobacillus acidophilus* Z048 | $1 \times 10^{\wedge}6.7$ CFU/ml | Not observed |
| AMR 4 | HPIV-2 | $1 \times 10^{\wedge}5.6$ TCID50/ml | Not observed |

TABLE 15-continued

Organisms and concentrations of the AMR formulation specificity panel[2]

| Panel | Organism | Test Concentration | Cross-Reactivity Results |
|---|---|---|---|
| | *Neisseria elongata* Z071 | $1 \times 10^{\wedge}8.1$ CFU/ml | Not observed |
| | RSV A | $1 \times 10^{\wedge}6.1$ TCID50/ml | Not observed |
| | IA/Massachusetts/15/13 2009 H1N1 | $1 \times 10^{\wedge}3.4$ TCID50/ml | Not observed |
| | *Legionella pneumophila* Philadelphia | $1 \times 10^{\wedge}8.5$ CFU/ml | Not observed |
| | *Mycobacterium* inracellular lysate | $1 \times 10^{\wedge}5.6$ CFU/ml | Not observed |
| AMR 5 | HPIV-3 | $1 \times 10^{\wedge}6.1$ TCID50/ml | Not observed |
| | HSV-2 Type 2G Strain | $1 \times 10^{\wedge}4.8$ TCID50/ml | Not observed |
| | IA/Victoria/361/2011 | $1 \times 10^{\wedge}3.5$ TCID50/ml | Not observed |
| | *Staphylococcus aureus* MSSA | $1 \times 107.9$ CFU/ml | Not observed |
| | Epstein-Barr Virus B95-8 | $1 \times 10^{\wedge}6.8$ copies/ml | Not observed |
| | *Haemophilus Influenzae* type b; Eagan | $1 \times 10^{\wedge}7.2$ CFU/ml | Not observed |
| AMR 6 | HPIV-4a | $1 \times 10^{\wedge}4.0$ TCID50/ml | Not observed |
| | IA/Switzerland/9715293/2013 H3N2 | $1 \times 10^{\wedge}3.4$ TCID50/ml | Not observed |
| | *Mycoplasma pneumoniae* M129 | $1 \times 10^{\wedge}6.1$ CFU/ml | Not observed |
| | *Streptococcus pyogenes* Z018 | $1 \times 10^{\wedge}7.7$ CFU/ml | Not observed |
| | *Staphylococcus haemolyticus* Z067 | $1 \times 10^{\wedge}7.3$ CFU/ml | Not observed |
| | *Lactobacillus plantarum* 17-5 | $1 \times 10^{\wedge}7.2$ CFU/ml | Not observed |
| AMR 7 | *Legionella micdadei* Tatlock | $1 \times 10^{\wedge}7.7$ CFU/ml | Not observed |
| | IB/Brisbane/33/08 | $1 \times 10^{\wedge}3.45$ TCID50/ml | Not observed |
| | *Staphylococcus epidermidis* MRSE | $1 \times 10^{\wedge}7.8$ TCID50/ml | Not observed |
| | *Streptococcus agalactiae* | $1 \times 10^{\wedge}7.2$ CFU/ml | Not observed |
| | *Klebsiella pneumonia* Z026 | $1 \times 10^{\wedge}8.1$ CFU/ml | Not observed |
| AMR 8 | Measles Virus | $1 \times 10^{\wedge}3.7$ TCID50/ml | Not observed |
| | *Moraxella catarrhalis* Ne 11 | $1 \times 10^{\wedge}5.3$ CFU/ml | Not observed |
| | IB/Massachusetts/2/2012 | $1 \times 10^{\wedge}3.5$ TCID50/ml | Not observed |
| | *Streptococcus pneumoniae* | $1 \times 10^{\wedge}6.2$ CFU/ml | Not observed |
| | Mumps Virus 1 | $1 \times 10^{\wedge}4.3$ TCID50/ml | Not observed |
| AMR 9 | *Mycobacterium tuberculosis* lysate | $1 \times 10^{\wedge}5.4$ TCID50/ml | Not observed |
| | *Neisseria meningitidis* A | $1 \times 10^{\wedge}7.2$ CFU/ml | Not observed |
| | *Mycoplasma hominis* | $1 \times 103.3$ CFU/ml | Not observed |
| | RSV B | $1 \times 10^{\wedge}6.4$ TCID50/ml | Not observed |
| | *Streptococcus salivarius* | $1 \times 10^{\wedge}6.7$ CFU/ml | Not observed |
| AMR 10 | *Pseudomonas aeruginosa* Z139 | $11 \times 10^{\wedge}8.3$ CFU/ml | Not observed |
| | *Serratia marcescens* Z053 | $11 \times 10^{\wedge}7.9$ CFU/ml | Not observed |
| | *Streptococcus sanguinis* Z089 | $11 \times 10^{\wedge}7.3$ CFU/ml | Not observed |
| | *Ureaplasma urealyticum* | $1 \times 10^{\wedge}8.0$ CFU/ml | Not observed |
| | Varicella Zoster Virus Ellen | $1 \times 10^{\wedge}3.5$ TCID50/ml | Not observed |

TABLE 15-continued

Organisms and concentrations of the AMR formulation specificity panel[2]

| Panel | Organism | Test Concentration | Cross-Reactivity Results |
|---|---|---|---|
| AMR 11 | Coxsackie B3 | 1×10^6.6 TCID50/ml | Not observed |
| AMR 12 | Coxsackie B4 | 1×10^3.8 TCID50/ml | Not observed |
| AMR 13 | Coxsackie B5/10/2006 | 1×10^5.8 TCID50/ml | Not observed |
| AMR 14 | Coxsackievirus A10 | 1×10^3.7 TCID50/ml | Not observed |
| AMR 15 | Coxsackievirus A21 | 1×10^3.9 TCID50/ml | Not observed |
| AMR 16 | Echovirus 6 | 1×10^6.3 TCID50/ml | Not observed |
| AMR 17 | Enterovirus 11 | 1×10^6.8 TCID50/ml | Not observed |
| AMR 18 | Enterovirus 2 | 1×10^6.8 TCID50/ml | Not observed |
| AMR 19 | Enterovirus 3 | 1×10^4.8 TCID50/ml | Not observed |
| AMR 20 | Enterovirus 68 | 1×10^2.8 TCID50/ml | Not observed |
| AMR 21 | Enterovirus 70 | 1×10^3.8 TCID50/ml | Not observed |
| AMR 22 | Enterovirus 71 | 1×10^6.2 TCID50/ml | Not observed |
| AMR 23 | Poliovirus 1 | 1×10^6.3 TCID50/ml | Not observed |
| AMR 24 | Adenovirus 1 | 1×10^6.3 TCID50/ml | 17.3 AdV Ct |
|  | hMPV-3 Subtype B1 | 1×10^6.1 TCID50/ml | 22.9 hMPV Ct |
|  | Rhino virus 1A | 1×10^4.4 TCID50/ml | 22.5 RV Ct |
| AMR 25 | Adenovirus 4 | 1×10^3.7 TCID50/ml | 21.4 AdV Ct |
|  | hMPV-9 Subtype A1 | 1×10^7.5 TCID50/ml | 19.1 hMPV Ct |
|  | Rhinovirus 26B | 1×10^3.7 TCID50/ml | 24.0 RV Ct |
| AMR 26 | Adenovirus 7a | 1×10^5.6 TCID50/ml | 16.9 AdV Ct |

[2]Target nucleic acids were isolated from previously characterized stock organisms obtained from TriCore Reference Laboratories (Albuquerque, NM); ZeptoMetrix Corporation (Buffalo, NY); and ATCC (Manassas, VA).
$C_T$ = cycle time.

Conclusion

A multiplexed combination of the amplification and detection oligonucleotides presented in this review exhibits specificity for the targets of the AdV/hMPV/RV assay.

As described above in Example 11, SEQ ID NO:50 was subsequently substituted by SEQ ID NO:75 in the multiplex reagent. This modified PCR reaction formulation was tested in an amplification and detection reaction using clinical samples and challenge organisms. The modified AMR formulation provided results similar to those shown in this Example 12 (data not shown).

Exemplary Nucleic Acid Sequences.

The instant Table 16 provides exemplary sequences that are useful with the present disclosure. This table does not limit the scope of the disclosure. Sequences are presented according to World Intellectual Property Organization (WIPO) Handbook on Industrial Property Information and Documentation, Standard ST.25 (1998), including Tables 1 through 6 of Appendix 2.

TABLE 16

Exemplary nucleic acid sequences

| SEQ ID No | Sequence 5'>3' |
|---|---|
| 1 | CAGGACGCCTCGGRGTAYCTSAG |
| 2 | GGAGCCACVGTGGGRTT |
| 3 | AAYCCCACBGTGGCTCC |
| 4 | CCGGGTCTGGTGCAGTTTGCCCGC |
| 5 | CACATCGCCGGACAGGA |
| 6 | CATACTGAAGTAGGTGTCTGT |
| 7 | ACAGACACCTACTTCAGTATG |
| 8 | CGGTGGTCACATCGTGG |
| 9 | CCACGATGTGACCACCG |
| 10 | AGTACCTCAGTCCGGGTCTGGTG |
| 11 | ATGGCTACCCCTTCGATG |
| 12 | ACCCCMTCGATGATGCC |
| 13 | GCGGGCGAATTGCACCA |
| 14 | TGGTGCAATTCGCCCGC |
| 15 | GCGGGCAAAYTGCACCA |

TABLE 16-continued

Exemplary nucleic acid sequences

| SEQ ID No | Sequence 5'>3' |
|---|---|
| 16 | TGGTGCARTTTGCCCGC |
| 17 | GACTCAGGTACTCCGAAGCATCCT |
| 18 | AGGATGCTTCGGAGTACCTGAGTC |
| 19 | CTCAGGTACTCCGAGGCGTCCT |
| 20 | AGGACGCCTCGGAGTACCTGAG |
| 21 | CTCAGGTACTCCGAAGCATCCT |
| 22 | AGGATGCTTCGGAGTACCTGAG |
| 23 | CAGGTACTCCGAGGCGTCCT |
| 24 | AGGACGCCTCGGAGTACCTG |
| 25 | ACCCCATCGATGATGCC |
| 26 | ACCCCCTCGATGATGCC |
| 27 | GCGGGCAAACTGCACCA |
| 28 | GCGGGCAAATTGCACCA |
| 29 | CTCAGGTATTCCGAGGCATCCT |
| 30 | AGGATGCCTCGGAATACCTGAG |
| 31 | ACCCCATCGATGCTGCC |
| 32 | ACCCCATCGATGATGCC |
| 33 | TGGGCGTACATGCACATC |
| 34 | GTGGTCTTACATGCACATC |
| 35 | GTGGGCATACATGCACATC |
| 36 | AGGATGCTTCGGAGTACCTGAG |
| 37 | AGGACGCCTCGGAGTACCTG |
| 38 | ARTGGKCDTACATGCACATC |
| 39 | CAGGACGCCTCGGAGTACCT |
| 40 | AGGATGCTTCGGAGTACCTGAG |
| 41 | CACGATGTGACCACAGA |
| 42 | CAYGATGTGACCACAGA |
| 43 | CACGAYGTGACCACAGA |
| 44 | CACGATGTGACCACSGA |
| 45 | CACGATGTGACCACVGA |
| 46 | CAYGAYGTGACCACVGA |
| 47 | Human adenovirus 9 gene for hexon, complete cds AB330090.1 and gi number GI: 190356540 |
| 48 | AGCCTGCGTGGCGGCCA |
| 49 | AGCCUGCGUGGUGCCCUGCC |
| 50 | CACTAGTUTGGTCGATGAGGCT |
| 51 | CCATCTGTAGATTAGGGUAATGAGGCT |
| 52 | CCCAACTTTGCAAGTGTTGTTCTCGG |

TABLE 16-continued

Exemplary nucleic acid sequences

| SEQ ID No | Sequence 5'>3' |
|---|---|
| 53 | CCCCAATTTTGCTAGTGTTGTTCTTGG |
| 54 | CCUGCGTGGCTGCCTGC |
| 55 | CGTCGACCGAAGTCCTGCAAAAGGTCAC |
| 56 | CTGCTGCTGAAAATAGTTCTGTGTTTGG |
| 57 | GAAACACGGACACCCAAAGTAGT |
| 58 | GGCCTCTGCTAAAGCAACACC |
| 59 | GTAGATCGGGGCAATGGGGCT |
| 60 | GTAGATCGGGGTAATGGGGCT |
| 61 | GTGGCGCGGGCGAACTGC |
| 62 | GTTGCACGGGCGAACTGC |
| 63 | TACATGCACATCGCCGGGCAGGA |
| 64 | TACATGCACATCTCGGGCCAGGA |
| 65 | TAGACCTGGCAGATGAGGC |
| 66 | TGCCGCAGAACGTTGCGAA |
| 67 | TGCCTCAGGCTTAGGCATAATAGGTATGTATCG |
| 68 | TGCTGCAGAAAATAGCTCTGTGTTTGG |
| 69 | TGCTTCAGGTCTAGGTATAATCGGAATGTACAG |
| 70 | TGCTTCAGGTTTAGGCATAATCGGAATGTACAG |
| 71 | TGGCCACTCCGTCGATGATG |
| 72 | TGGCTACCCCATCGATGATG |
| 73 | TGGCTACCCCATCGATGCTG |
| 74 | TGGCTACCCCUTCGATGATG |
| 75 | CTAGTUTGGTCGATGAGGCT |
| 76 | Human rhinovirus C isolate Resp_4051/07 5' UTR. HM581865.1 GI:302378331 |
| 77 | CCATCTGTAGRTYRGGGYAATGRGGCTAC |
| 78 | GTAGATTAGGGUAATGAGGCTAC |
| 79 | GTAGATTAGGGUAATGAGGCT |
| 80 | GTAGATCRGGGUAATGGGGCT |
| 81 | GTAGATCRGGGYAATGGGGCT |
| 82 | GTAGATCRGGGUAATGRGGCT |
| 83 | GTAGATCGGGGTAATGGGGCTAC |
| 84 | GTAGATCGGGGCAATGGGGCTAC |
| 85 | GTAGATCRGGGYAATGRGG |
| 86 | GTAGATCRGGGYAATGRGGCTAC |
| 87 | AGCCTGCGTGGYKSCCWRCC |
| 88 | AGCCYGCGTGGTGCCCYGCC |

TABLE 16-continued

Exemplary nucleic acid sequences

| SEQ ID No | Sequence 5'>3' |
|---|---|
| 89 | CUGCGTGGTGCCCYGCC |
| 90 | CYGCGTGGTGCCCUGCC |
| 91 | AGCCYGCGTGGTGC |
| 92 | AGCCTGCGTGGCGGCCA |
| 93 | AGCCYGCGTGGTGCCC |
| 94 | CCUGCGTGGCTGCCTGC |
| 95 | GRTTAGCCRCATTCAGGGGCCGGAGGA |
| 96 | GAAACACGGACACCCAAAGTAGTYGGTYCCRTCCC |
| 97 | AAGTAGTTGGTCCCATCCC |
| 98 | AAGTAGTTGGTTCCATCCC |
| 99 | AAGTAGTCGGTCCCATCCC |
| 100 | AAGTAGTTGGTCCCGTCCC |
| 101 | Human rhinovirus 37 5' UTR EU096024.1 |
| 102 | CACTAGTTTGGYCGATGAGGCT |
| 103 | CTAGTYTGGTCGATGAGGC |
| 104 | CTAGTYTGGTCGATGAGG |
| 105 | GTYTGGTCGATGAGGC |
| 106 | TAGTYTGGTCGATGAGGCT |
| 107 | TAGTUTGGTCGATGAGGCT |
| 108 | RCATTCAGGGGCCGGAGG |
| 109 | AGCCTGCGTGGCGGCCARCC |
| 110 | CCUGCGTGGCTGCCTRC |
| 111 | CTGCGTGGTGCCCTACC |
| 112 | CCYGCGTGGCTGCCTAC |
| 113 | AGCCYGCGTGGCTG |
| 114 | AGCCYGCGTGGCTGCC |
| 115 | GRTTAGCCRCATTCRGGRGCCGGAGGA |
| 116 | GCATTCAGGGGCCGGAGG |
| 117 | GAAACACGGACACCCAAAGTAGTYGG |
| 118 | GAAACACGGACACCCAAAGTAGTYGGTCC |
| 119 | AAGTAGTCGGTCCCGTCCC |
| 120 | Human rhinovirus A2 EU095989.1 GI: 158830711 |
| 121 | YRGRCYTGGCAGATGRGGC |
| 122 | TARACCTGGCAGATGRGGC |
| 123 | TAGACCTGGCAGATGGGGC |
| 124 | TAGACCTGGCAGATGRGGC |
| 125 | TARACCTGGCAGATGGGGC |

TABLE 16-continued

Exemplary nucleic acid sequences

| SEQ ID No | Sequence 5'>3' |
|---|---|
| 126 | TARACCTGGTAGATGRGGC |
| 127 | TARACCTGGCAGATGRG |
| 128 | TARACCTGGCAGATGRGG |
| 129 | CARACCTGGCAGATGRGGC |
| 130 | CCTGCCAGATGRGGC |
| 131 | WGCCTGCGYGGCKGCCWRC |
| 132 | CCYGCGCGGCTGCCTRC |
| 133 | CCYGCGTGGCTGCCTRC |
| 134 | CCYGCGTGGCTGCCTGC |
| 135 | WGCCYGCGTGGCTGCCTGC |
| 136 | AGCCYGCGTGGCTGCCTGC |
| 137 | GRTTAGCCGCATTCRGGRGCCGGAGGA |
| 138 | TACATGCACATCKCSGGVCAGGAYGCYTCGGAGTACCTGAGCCCCG |
| 139 | ACGCCTCGGAGTACCTGAGCCC |
| 140 | CGGGGCTCAGGTACTCCGAGGCGT |
| 141 | GTKGCRCGGGCRAAYTGCACCA |
| 142 | GTKGCRCGGGCGAACTGC |
| 143 | GTGGCGCGGGCAAACTG |
| 144 | GTKGCRCGGGCRAACTGC |
| 145 | GTGGCRCGGGCRAACTGC |
| 146 | GTKGCGCGGGCRAACTGC |
| 147 | GTGGCGCGGGCRAACTGC |
| 148 | GTGGCRCGGGCGAACTGC |
| 149 | GTKGCGCGGGCGAACTGC |
| 150 | Human metapneumovirus isolate NL/1/99, complete genome. AY525843.1 GI:50059145 |
| 151 | CSSCCAATTTTGCTAGTGTTGTTCTTGG |
| 152 | CGGCCAATTTTGCTAGTGTTGTTCTTGG |
| 153 | CAATTTTGCTAGTGTTGTTCTTGG |
| 154 | CCAATTTTGCTAGTGTTGTTCTTGG |
| 155 | TGCTTCAGGTYTAGGYATAATCGGAATGTWCAGAGG |
| 156 | TGCTTCAGGTTTAGGCATAATCGGAATGTTCAGAGG |
| 157 | TGCTTCAGGTCTAGGTATAATCGGAATGT |
| 158 | GCAGAAAATAGCTCTGTGTTTGG |
| 159 | Human metapneumovirus isolate SIN05NTU84 nucleoprotein (N) gene, partial cds JQ309642.1 GI:374721604 |
| 160 | CTTTGCAAGTGTTGTTCTCGG |
| 161 | TGCCTCAGGCYTAGGCATAATMGGYATGTATCGHGGG |

TABLE 16-continued

Exemplary nucleic acid sequences

| SEQ ID No | Sequence 5'>3' |
|---|---|
| 162 | TCAGGCTTAGGCATAATAGGTATGTATCG |
| 163 | CCTCAGGCTTAGGCATAATAGGTATGTATCGAG |
| 164 | CCTCAGGCTTAGGCATAATAGGTATGTATCG |
| 165 | CCTCAGGCTTAGGCATAATAGGTATGTATCGCG |
| 166 | CCTCAGGCTTAGGCATAATAGGTATGTATCGUG |
| 167 | TGCCTCAGGCCTAGGCATAATCGGCATGTATCGUGGG |
| 168 | TGCCTCAGGCCTAGGCATAATCGGCATGTATCGTGGG |
| 169 | CTCAGGCTTAGGCATAATAGGTATGTATCGCG |
| 170 | TGCCTCAGGCTTAGGCATAATAGGTATGTATCGC |
| 171 | TGCCTCAGGCTTAGGCATAATAGGTATGTATCGCG |
| 172 | TGCCTCAGGCTTAGGCATAATAGGTATGTATCGCGG |
| 173 | TGCCTCAGGCTTAGGCATAATAGGTATGTATCGUGGG |
| 174 | TGCCTCAGGCTTAGGCATAATAGGTATGTATCGAGGG |
| 175 | TGCCTCAGGCTTAGGCATAATCGGTATGTATCGCGGG |
| 176 | TGCCTCAGGCTTAGGCATAATAGGTATGTATCGCGGG |
| 177 | CTGCTGCWGAAAATAGYTCTGTGTTTGG |
| 178 | TGCTGAAAATAGTTCTGTGTTTGG |

Sequence symbols are per Table 1 of World Intellectual Property Organization (WIPO) Handbook on Industrial Property Information and Documentation, Standard ST.25 (1998) ("WIPO ST.25 (1998)").

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the disclosure is also thereby described in terms of any individual member or subgroup of members of the Markush group.

What is claimed is:

1. A method for determining the presence or absence of a Rhinovirus target nucleic acid in a sample, the method comprising the steps of:
(A) contacting the sample with a first amplification oligomer and a second amplification oligomer, wherein the first amplification oligomer comprises a target hybridizing sequence consisting of SEQ ID NO:121 and the second amplification oligomer comprises a target hybridizing sequence consisting of SEQ ID NO:57;
(B) performing an in vitro nucleic acid amplification reaction wherein the Rhinovirus target nucleic acid, if present in the sample, is used by the first amplification oligomer and the second amplification oligomer to generate the amplification product; and
(C) performing an in vitro nucleic acid detection reaction to detect the amplification product, thereby determining the presence or absence of the Rhinovirus target nucleic acid in the sample.

2. The method of claim 1, wherein the sample is a mucosal sample.

3. The method of claim 2 wherein the sample is obtained using a nasopharyngeal swab.

4. The method of claim 1, wherein, before step (A) a sample preparation step is performed to separate the target nucleic acid in the sample away from other sample components.

5. The method of claim 4, wherein the sample preparation step comprises a target capture step, wherein the sample is contacted with a nucleic acid target capture probe comprising a target hybridizing sequence and an immobilized probe binding region that is a homopolymeric nucleotide sequence.

6. The method of claim 5, wherein the target hybridizing sequence is a poly-K nucleotide sequence and the homopolymeric nucleotide sequence is $T_{0-4}A_{10-36}$.

7. The method of claim 1, wherein the first amplification oligomer target hybridizing sequence and/or the second amplification oligomer target hybridizing sequence contains at least one 5-Me-dC, or at least one non-Watson Crick base, or at least one degenerate base, or a combination thereof.

8. The method of claim 1, wherein the first amplification oligomer target hybridizing sequence consists of SEQ ID NO:65.

9. The method of claim 1, wherein the performing an in vitro nucleic acid detection reaction comprises detecting the amplification product with one or more detection probe oligomers.

10. The method of claim 9, wherein the one or more detection probe oligomers are independently selected from the group consisting of SEQ ID NOS: 48, 54, and 131 to 136.

11. The method of claim 9, wherein at least one of the detection probe oligomers contains at least one degenerate nucleotide residue, or at least one non-Watson Crick residue, or at least one nucleoside analog, or a combination thereof.

12. The method of claim 9, wherein at least one of the detection probe oligomers comprises a detectable fluorescent label.

13. The method of claim 9, wherein the detection probe oligomer comprises a detectable fluorescent label and a quencher moiety that can quench a fluorescent emission from the fluorescent detectable label.

14. The method of claim 1, wherein the in vitro nucleic acid amplification reaction comprises thermal cycling.

15. The method of claim 1, wherein the in vitro nucleic acid amplification reaction of step (B) and the in vitro nucleic acid detection reaction of step (C) are performed simultaneously.

16. The method of claim 9, wherein the one or more detection probe oligomers comprises a detection probe of from 17 to 19 contiguous nucleotides of SEQ ID NO:131.

17. A method for determining the presence or absence of a Rhinovirus target nucleic acid in a sample, the method comprising the steps of:
(A) contacting the sample with a formulation for the amplification and detection of a Rhinovirus target nucleic acid, containing:
a) a first amplification oligomer comprising a target hybridizing sequence consisting of SEQ ID NO:121 and a second amplification oligomer comprising a target hybridizing sequence consisting of SEQ ID NO:57;
b) a detection probe oligomer;
c) an enzyme;
d) dNTPs;
e) EDTA; and
f) water;
(B) performing an in vitro nucleic acid amplification reaction wherein the Rhinovirus target nucleic acid, if present in the sample, is used by the first amplification oligomer and the second amplification oligomer to generate the amplification product; and
(C) performing an in vitro nucleic acid detection reaction to detect the amplification product, thereby determining the presence or absence of the Rhinovirus target nucleic acid in the sample.

* * * * *

SEQUENCE LISTING

```
Sequence total quantity: 178
SEQ ID NO: 1             moltype = DNA  length = 23
FEATURE                  Location/Qualifiers
misc_feature             1..23
                         note = Synthetic Oligonucleotide
source                   1..23
                         mol_type = other DNA
                         organism = synthetic construct
SEQUENCE: 1
```
caggacgcct cggrgtayct sag                                          23

SEQ ID NO: 2           moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 2
ggagccacvg tgggrtt                                                 17

SEQ ID NO: 3           moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 3
aaycccacbg tggctcc                                                 17

SEQ ID NO: 4           moltype = DNA   length = 24
FEATURE                Location/Qualifiers
misc_feature           1..24
                       note = Synthetic Oligonucleotide
source                 1..24
                       mol_type = other DNA
                       organism = synthetic construct
SEQUENCE: 4
ccgggtctgg tgcagtttgc ccgc                                         24

SEQ ID NO: 5           moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 5
cacatcgccg gacagga                                                 17

SEQ ID NO: 6           moltype = DNA   length = 21
FEATURE                Location/Qualifiers
misc_feature           1..21
                       note = Synthetic Oligonucleotide
source                 1..21
                       mol_type = other DNA
                       organism = synthetic construct
SEQUENCE: 6
catactgaag taggtgtctg t                                            21

SEQ ID NO: 7           moltype = DNA   length = 21
FEATURE                Location/Qualifiers
misc_feature           1..21
                       note = Synthetic Oligonucleotide
source                 1..21
                       mol_type = other DNA
                       organism = synthetic construct
SEQUENCE: 7
acagacacct acttcagtat g                                            21

SEQ ID NO: 8           moltype = DNA   length = 17
FEATURE                Location/Qualifiers
misc_feature           1..17
                       note = Synthetic Oligonucleotide
source                 1..17
                       mol_type = other DNA
                       organism = synthetic construct
SEQUENCE: 8
cggtggtcac atcgtgg                                                 17

SEQ ID NO: 9           moltype = DNA   length = 17
FEATURE                Location/Qualifiers
misc_feature           1..17
                       note = Synthetic Oligonucleotide
source                 1..17
                       mol_type = other DNA
                       organism = synthetic construct

```
SEQUENCE: 9
ccacgatgtg accaccg                                                  17

SEQ ID NO: 10           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 10
agtacctcag tccgggtctg gtg                                           23

SEQ ID NO: 11           moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 11
atggctaccc cttcgatg                                                 18

SEQ ID NO: 12           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 12
accccmtcga tgatgcc                                                  17

SEQ ID NO: 13           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 13
gcgggcgaat tgcacca                                                  17

SEQ ID NO: 14           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 14
tggtgcaatt cgcccgc                                                  17

SEQ ID NO: 15           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 15
gcgggcaaay tgcacca                                                  17

SEQ ID NO: 16           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 16
tggtgcartt tgcccgc                                                  17

SEQ ID NO: 17           moltype = DNA  length = 24
FEATURE                 Location/Qualifiers
misc_feature            1..24
                        note = Synthetic Oligonucleotide
source                  1..24
                        mol_type = other DNA
```

```
                              organism = synthetic construct
SEQUENCE: 17
gactcaggta ctccgaagca tcct                                              24

SEQ ID NO: 18          moltype = DNA   length = 24
FEATURE                Location/Qualifiers
misc_feature           1..24
                       note = Synthetic Oligonucleotide
source                 1..24
                       mol_type = other DNA
                       organism = synthetic construct
SEQUENCE: 18
aggatgcttc ggagtacctg agtc                                              24

SEQ ID NO: 19          moltype = DNA   length = 22
FEATURE                Location/Qualifiers
misc_feature           1..22
                       note = Synthetic Oligonucleotide
source                 1..22
                       mol_type = other DNA
                       organism = synthetic construct
SEQUENCE: 19
ctcaggtact ccgaggcgtc ct                                                22

SEQ ID NO: 20          moltype = DNA   length = 22
FEATURE                Location/Qualifiers
misc_feature           1..22
                       note = Synthetic Oligonucleotide
source                 1..22
                       mol_type = other DNA
                       organism = synthetic construct
SEQUENCE: 20
aggacgcctc ggagtacctg ag                                                22

SEQ ID NO: 21          moltype = DNA   length = 22
FEATURE                Location/Qualifiers
misc_feature           1..22
                       note = Synthetic Oligonucleotide
source                 1..22
                       mol_type = other DNA
                       organism = synthetic construct
SEQUENCE: 21
ctcaggtact ccgaagcatc ct                                                22

SEQ ID NO: 22          moltype = DNA   length = 22
FEATURE                Location/Qualifiers
misc_feature           1..22
                       note = Synthetic Oligonucleotide
source                 1..22
                       mol_type = other DNA
                       organism = synthetic construct
SEQUENCE: 22
aggatgcttc ggagtacctg ag                                                22

SEQ ID NO: 23          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 23
caggtactcc gaggcgtcct                                                   20

SEQ ID NO: 24          moltype = DNA   length = 20
FEATURE                Location/Qualifiers
misc_feature           1..20
                       note = Synthetic Oligonucleotide
source                 1..20
                       mol_type = other DNA
                       organism = synthetic construct
SEQUENCE: 24
aggacgcctc ggagtacctg                                                   20

SEQ ID NO: 25          moltype = DNA   length = 17
FEATURE                Location/Qualifiers
misc_feature           1..17
                       note = Synthetic Oligonucleotide
source                 1..17
```

```
                        mol_type = other DNA
                        organism = synthetic construct
SEQUENCE: 25
accccatcga tgatgcc                                                      17

SEQ ID NO: 26           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 26
acccccctcga tgatgcc                                                     17

SEQ ID NO: 27           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 27
gcgggcaaac tgcacca                                                      17

SEQ ID NO: 28           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 28
gcgggcaaat tgcacca                                                      17

SEQ ID NO: 29           moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 29
ctcaggtatt ccgaggcatc ct                                                22

SEQ ID NO: 30           moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 30
aggatgcctc ggaatacctg ag                                                22

SEQ ID NO: 31           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 31
accccatcga tgctgcc                                                      17

SEQ ID NO: 32           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 32
accccatcga tgatgcc                                                      17

SEQ ID NO: 33           moltype = DNA  length = 18
FEATURE                 Location/Qualifiers
misc_feature            1..18
                        note = Synthetic Oligonucleotide
```

```
source                   1..18
                         mol_type = other DNA
                         organism = synthetic construct
SEQUENCE: 33
tgggcgtaca tgcacatc                                                    18

SEQ ID NO: 34            moltype = DNA   length = 19
FEATURE                  Location/Qualifiers
misc_feature             1..19
                         note = Synthetic Oligonucleotide
source                   1..19
                         mol_type = other DNA
                         organism = synthetic construct
SEQUENCE: 34
gtggtcttac atgcacatc                                                   19

SEQ ID NO: 35            moltype = DNA   length = 19
FEATURE                  Location/Qualifiers
misc_feature             1..19
                         note = Synthetic Oligonucleotide
source                   1..19
                         mol_type = other DNA
                         organism = synthetic construct
SEQUENCE: 35
gtgggcatac atgcacatc                                                   19

SEQ ID NO: 36            moltype = DNA   length = 22
FEATURE                  Location/Qualifiers
misc_feature             1..22
                         note = Synthetic Oligonucleotide
source                   1..22
                         mol_type = other DNA
                         organism = synthetic construct
SEQUENCE: 36
aggatgcttc ggagtacctg ag                                               22

SEQ ID NO: 37            moltype = DNA   length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 37
aggacgcctc ggagtacctg                                                  20

SEQ ID NO: 38            moltype = DNA   length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 38
artggkcdta catgcacatc                                                  20

SEQ ID NO: 39            moltype = DNA   length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 39
caggacgcct cggagtacct                                                  20

SEQ ID NO: 40            moltype = DNA   length = 22
FEATURE                  Location/Qualifiers
misc_feature             1..22
                         note = Synthetic Oligonucleotide
source                   1..22
                         mol_type = other DNA
                         organism = synthetic construct
SEQUENCE: 40
aggatgcttc ggagtacctg ag                                               22

SEQ ID NO: 41            moltype = DNA   length = 17
FEATURE                  Location/Qualifiers
misc_feature             1..17
```

|                  | note = Synthetic Oligonucleotide |     |
|---|---|---|
| source           | 1..17 |     |
|                  | mol_type = other DNA |     |
|                  | organism = synthetic construct |     |
| SEQUENCE: 41     |       |     |
| cacgatgtga ccacaga |     | 17  |

| SEQ ID NO: 42    | moltype = DNA  length = 17 |     |
|---|---|---|
| FEATURE          | Location/Qualifiers |     |
| misc_feature     | 1..17 |     |
|                  | note = Synthetic Oligonucleotide |     |
| source           | 1..17 |     |
|                  | mol_type = other DNA |     |
|                  | organism = synthetic construct |     |
| SEQUENCE: 42     |       |     |
| caygatgtga ccacaga |   | 17  |

| SEQ ID NO: 43    | moltype = DNA  length = 17 |     |
|---|---|---|
| FEATURE          | Location/Qualifiers |     |
| misc_feature     | 1..17 |     |
|                  | note = Synthetic Oligonucleotide |     |
| source           | 1..17 |     |
|                  | mol_type = other DNA |     |
|                  | organism = synthetic construct |     |
| SEQUENCE: 43     |       |     |
| cacgaygtga ccacaga |   | 17  |

| SEQ ID NO: 44    | moltype = DNA  length = 17 |     |
|---|---|---|
| FEATURE          | Location/Qualifiers |     |
| misc_feature     | 1..17 |     |
|                  | note = Synthetic Oligonucleotide |     |
| source           | 1..17 |     |
|                  | mol_type = other DNA |     |
|                  | organism = synthetic construct |     |
| SEQUENCE: 44     |       |     |
| cacgatgtga ccacsga |   | 17  |

| SEQ ID NO: 45    | moltype = DNA  length = 17 |     |
|---|---|---|
| FEATURE          | Location/Qualifiers |     |
| misc_feature     | 1..17 |     |
|                  | note = Synthetic Oligonucleotide |     |
| source           | 1..17 |     |
|                  | mol_type = other DNA |     |
|                  | organism = synthetic construct |     |
| SEQUENCE: 45     |       |     |
| cacgatgtga ccacvga |   | 17  |

| SEQ ID NO: 46    | moltype = DNA  length = 17 |     |
|---|---|---|
| FEATURE          | Location/Qualifiers |     |
| misc_feature     | 1..17 |     |
|                  | note = Synthetic Oligonucleotide |     |
| source           | 1..17 |     |
|                  | mol_type = other DNA |     |
|                  | organism = synthetic construct |     |
| SEQUENCE: 46     |       |     |
| caygaygtga ccacvga |   | 17  |

| SEQ ID NO: 47    | moltype = DNA  length = 2832 |     |
|---|---|---|
| FEATURE          | Location/Qualifiers |     |
| source           | 1..2832 |     |
|                  | mol_type = unassigned DNA |     |
|                  | organism = Human adenovirus type 9 |     |
| SEQUENCE: 47     |       |     |

```
atggccaccc cctcgatgat gccgcagtgg gcgtacatgc acatcgccgg gcaggacgcc   60
tcggagtacc tgagcccggg tctggtgcag tttgcccgcg ccaccgacac gtacttcagc  120
ctgggcaaca agtttaggaa ccccacggtg gccccgaccc acgatgtgac cacggaccgg  180
tcccagcgtc tgacgctgcg cttcgtgccc gtggatcgcg aggacaccac gtactcgtac  240
aaggcgcgct tcactctggc cgtgggcgac aaccgggtgc tagacatggc cagcacttac  300
tttgacatcc gcggcgtcct ggaccgcggt cccagcttca acccctactc gggcacagct  360
tacaacagtc tggcccccaa gggtgccccc aactccagcc agtggcttgc aaaagacacc  420
aatgctggcg atcaagcatt aaaaacccac acacatggcg tagctgctat gggggggaaca  480
gatatcacag caaagggttt gcaaattggt gttgacacga ctgaaaacaa gaatgagcct  540
atttatgcaa atgaaatata ccagccgaaa cctcaggtag gagaggaaaa cttgcaagat  600
gttgaaaact tttatggagg cagagctctt aaaaagaaa ccaaaatgaa accttgctat  660
ggctcgtttg ccagacccac aaatgaaaaa ggcggtcaag ccaaattttt aactgacggc  720
gatggtcagc taactaaaaa tcatgatatc acaatgaatt ctttgacac tcctggagga  780
acagttggtc aggatactga acttgaagca gacattgtta tgtatgctga aatgtgcat  840
ctggaaactc cagacacgca tgtggtgtac aaaccaggaa cttctgatga gagttcagaa  900
gcaaatttgg ttcagcagtc catgccaaac aggcccaact catcggctt cagggacaac  960
```

```
tttgtgggtc tcatgtacta taacagcact ggcaacatgg gtgtgctggc tggtcaagca  1020
tctcagttga atgctgtggt cgacttgcaa gacagaaaca cagagctgtc ttaccagctc  1080
ttgctagatt ctctgggtga cagaaccaga tactttagca tgtggaactc tgcagtggac  1140
agttatgatc ctgatgtcag gattattgaa atcacggtg tggaagatga acttccaaac  1200
tattgcttcc cattggatgg agctggcact aatgctacct accaaggtgt aaaagttaaa  1260
aatggccaag atggagatgg aaacgcagat tgggaaaaag atccaaatct tgcttcacga  1320
aaccaaatat gcaagggtaa catcttcgcc atggagatca acctccaggc caacctgtgg  1380
aagagttttc tgtactcgaa tgtggccctg tacctgcccg actcatacaa gtacacgccg  1440
gccaacgtca cgctgcccgc caataccaac acctacgagt acatgaacgg ccgcgtggta  1500
gcccctcgc tggtggacgc ctacatcaac atcggtcgct ggtggtcgct ggacccatg  1560
gacaacgtca accattcaa ccaccaccgc aacgcgggcc tgcgttaccg ctccatgctt  1620
ctgggcaacg gccgctacgt gcccttccac atccaagtgc cccaaaagtt ctttgccatc  1680
aagaacctgc tcctgctccc cggctcctac acctacgagt ggaacttccg caaggatgtc  1740
aacatgatcc tgcagagttc cctcggaaac gacctgcgcg tcgacggcgc ctccgtccga  1800
ttcgacagcg tcaacctcta cgccacattc ttccccatgg cgcacaacac cgcctccacc  1860
ctggaagcca tgctgcgcaa cgacaccaac gaccagtcct tcaacgacta cctctccggcc  1920
gccaacatgc tctaccccat cccggccaag gccaccaacg tgcccatctc catccccctcg  1980
cgcaactggg ccgccttccg cggctggagt ttcacccggc tcaagaccaa agaaactccc  2040
tccctcggct cgggtttcga tccctacttt gtatactcgg gttccatccc ctacctcgac  2100
gggaccttct acctcaacca caccttcaag aaggtctcca tcatgttcga ctcctcggtc  2160
agctggcccg gcaacgaccg gctgctcacg ccgaacgagt tcgagatcaa gcgcagtgtc  2220
gacggggagg gctacaatgt ggcccaatgc aacatggcag aggactggtt cctcgtccga  2280
atgctctccc actacaacat cggctaccag ggcttccacg tgcccgaggg ctacaaggac  2340
cgcatgtact ccttcttccg caacttccag cccatgagca ggcaggtggt cgatgagatc  2400
aactacaagg actacaaggc cgtcaccctg cccttccagc acaacaactc gggcttcacc  2460
ggctaccttg cacccaccat gcgtcagggg cagccctacc gccaacttt ccctatcct  2520
ctcatcggcc agacagccgt gccctctgtc acccagaaaa agttcctctg cgacagggtc  2580
atgtggcgca tccccttctc cagcaacttc atgtccatgg gcgccctcac cgacctgggt  2640
cagaacatgc tctatgccaa ctcggccac gcgctcgaca tgaccttcga ggtggacccc  2700
atggatgagc ccaccctcct ctatcttctc ttcgaagttt tcgacgtggt cagagtgcac  2760
cagccgcacc gcggcgtcat cgaggccgtc tacctgcgca cgcccttctc cgccggcaac  2820
gccaccacct aa                                                     2832

SEQ ID NO: 48          moltype = DNA  length = 17
FEATURE                Location/Qualifiers
misc_feature           1..17
                       note = Synthetic Oligonucleotide
source                 1..17
                       mol_type = other DNA
                       organism = synthetic construct SEQUENCE: 48
agcctgcgtg gcggcca                                                17

SEQ ID NO: 49          moltype = DNA  length = 20
FEATURE                Location/Qualifiers
misc_feature           1..20
                       note = Synthetic Oligonucleotide
source                 1..20
                       mol_type = other DNA
                       organism = synthetic construct
modified_base          17
                       mod_base = OTHER
                       note = uracil
modified_base          5
                       mod_base = OTHER
                       note = uracil SEQUENCE: 49
agcctgcgtg gtgccctgcc                                             20

SEQ ID NO: 50          moltype = DNA  length = 22
FEATURE                Location/Qualifiers
misc_feature           1..22
                       note = Synthetic Oligonucleotide
source                 1..22
                       mol_type = other DNA
                       organism = synthetic construct
modified_base          8
                       mod_base = OTHER
                       note = uracil SEQUENCE: 50
cactagtttg gtcgatgagg ct                                          22

SEQ ID NO: 51          moltype = DNA  length = 27
FEATURE                Location/Qualifiers
misc_feature           1..27
                       note = Synthetic Oligonucleotide
source                 1..27
                       mol_type = other DNA
                       organism = synthetic construct
```

```
                            modified_base       18
                                                mod_base = OTHER
                                                note = uracil
SEQUENCE: 51
ccatctgtag attagggtaa tgaggct                                             27

SEQ ID NO: 52           moltype = DNA  length = 26
FEATURE                 Location/Qualifiers
misc_feature            1..26
                        note = Synthetic Oligonucleotide
source                  1..26
                        mol_type = other DNA
                        organism = synthetic construct
SEQUENCE: 52
cccaactttg caagtgttgt tctcgg                                              26

SEQ ID NO: 53           moltype = DNA  length = 27
FEATURE                 Location/Qualifiers
misc_feature            1..27
                        note = Synthetic Oligonucleotide
source                  1..27
                        mol_type = other DNA
                        organism = synthetic construct
SEQUENCE: 53
ccccaattt tgctagtgttg ttcttgg                                             27

SEQ ID NO: 54           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
modified_base           3
                        mod_base = OTHER
                        note = uracil
SEQUENCE: 54
cctgcgtggc tgcctgc                                                        17

SEQ ID NO: 55           moltype = DNA  length = 28
FEATURE                 Location/Qualifiers
misc_feature            1..28
                        note = Synthetic Oligonucleotide
source                  1..28
                        mol_type = other DNA
                        organism = synthetic construct
SEQUENCE: 55
cgtcgaccga agtcctgcaa aaggtcac                                            28

SEQ ID NO: 56           moltype = DNA  length = 28
FEATURE                 Location/Qualifiers
misc_feature            1..28
                        note = Synthetic Oligonucleotide
source                  1..28
                        mol_type = other DNA
                        organism = synthetic construct
SEQUENCE: 56
ctgctgctga aaatagttct gtgtttgg                                            28

SEQ ID NO: 57           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 57
gaaacacgga cacccaaagt agt                                                 23

SEQ ID NO: 58           moltype = DNA  length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 58
ggcctctgct aaagcaacac c                                                   21
```

```
SEQ ID NO: 59              moltype = DNA   length = 21
FEATURE                    Location/Qualifiers
misc_feature               1..21
                           note = Synthetic Oligonucleotide
source                     1..21
                           mol_type = other DNA
                           organism = synthetic construct
SEQUENCE: 59
gtagatcggg gcaatggggc t                                              21

SEQ ID NO: 60              moltype = DNA   length = 21
FEATURE                    Location/Qualifiers
misc_feature               1..21
                           note = Synthetic Oligonucleotide
source                     1..21
                           mol_type = other DNA
                           organism = synthetic construct
SEQUENCE: 60
gtagatcggg gtaatggggc t                                              21

SEQ ID NO: 61              moltype = DNA   length = 18
FEATURE                    Location/Qualifiers
misc_feature               1..18
                           note = Synthetic Oligonucleotide
source                     1..18
                           mol_type = other DNA
                           organism = synthetic construct
SEQUENCE: 61
gtggcgcggg cgaactgc                                                  18

SEQ ID NO: 62              moltype = DNA   length = 18
FEATURE                    Location/Qualifiers
misc_feature               1..18
                           note = Synthetic Oligonucleotide
source                     1..18
                           mol_type = other DNA
                           organism = synthetic construct
SEQUENCE: 62
gttgcacggg cgaactgc                                                  18

SEQ ID NO: 63              moltype = DNA   length = 23
FEATURE                    Location/Qualifiers
misc_feature               1..23
                           note = Synthetic Oligonucleotide
source                     1..23
                           mol_type = other DNA
                           organism = synthetic construct
SEQUENCE: 63
tacatgcaca tcgccgggca gga                                            23

SEQ ID NO: 64              moltype = DNA   length = 23
FEATURE                    Location/Qualifiers
misc_feature               1..23
                           note = Synthetic Oligonucleotide
source                     1..23
                           mol_type = other DNA
                           organism = synthetic construct
SEQUENCE: 64
tacatgcaca tctcgggcca gga                                            23

SEQ ID NO: 65              moltype = DNA   length = 19
FEATURE                    Location/Qualifiers
misc_feature               1..19
                           note = Synthetic Oligonucleotide
source                     1..19
                           mol_type = other DNA
                           organism = synthetic construct
SEQUENCE: 65
tagacctggc agatgaggc                                                 19

SEQ ID NO: 66              moltype = DNA   length = 19
FEATURE                    Location/Qualifiers
misc_feature               1..19
                           note = Synthetic Oligonucleotide
source                     1..19
                           mol_type = other DNA
                           organism = synthetic construct
SEQUENCE: 66
tgccgcagaa cgttgcgaa                                                 19
```

```
SEQ ID NO: 67            moltype = DNA  length = 33
FEATURE                  Location/Qualifiers
misc_feature             1..33
                         note = Synthetic Oligonucleotide
source                   1..33
                         mol_type = other DNA
                         organism = synthetic construct
SEQUENCE: 67
tgcctcaggc ttaggcataa taggtatgta tcg                                   33

SEQ ID NO: 68            moltype = DNA  length = 27
FEATURE                  Location/Qualifiers
misc_feature             1..27
                         note = Synthetic Oligonucleotide
source                   1..27
                         mol_type = other DNA
                         organism = synthetic construct
SEQUENCE: 68
tgctgcagaa aatagctctg tgtttgg                                          27

SEQ ID NO: 69            moltype = DNA  length = 33
FEATURE                  Location/Qualifiers
misc_feature             1..33
                         note = Synthetic Oligonucleotide
source                   1..33
                         mol_type = other DNA
                         organism = synthetic construct
SEQUENCE: 69
tgcttcaggt ctaggtataa tcggaatgta cag                                   33

SEQ ID NO: 70            moltype = DNA  length = 33
FEATURE                  Location/Qualifiers
misc_feature             1..33
                         note = Synthetic Oligonucleotide
source                   1..33
                         mol_type = other DNA
                         organism = synthetic construct
SEQUENCE: 70
tgcttcaggt ttaggcataa tcggaatgta cag                                   33

SEQ ID NO: 71            moltype = DNA  length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 71
tggccactcc gtcgatgatg                                                  20

SEQ ID NO: 72            moltype = DNA  length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 72
tggctacccc atcgatgatg                                                  20

SEQ ID NO: 73            moltype = DNA  length = 20
FEATURE                  Location/Qualifiers
misc_feature             1..20
                         note = Synthetic Oligonucleotide
source                   1..20
                         mol_type = other DNA
                         organism = synthetic construct
SEQUENCE: 73
tggctacccc atcgatgctg                                                  20

SEQ ID NO: 74            moltype = DNA  length = 19
FEATURE                  Location/Qualifiers
misc_feature             1..19
                         note = Synthetic Oligonucleotide
source                   1..19
                         mol_type = other DNA
                         organism = synthetic construct
modified_base            11
```

|   |   |   |
|---|---|---|
| | mod_base = OTHER | |
| | note = uracil | |
| SEQUENCE: 74 | | |
| tggctacccc tcgatgatg | | 19 |
| | | |
| SEQ ID NO: 75 | moltype = DNA  length = 20 | |
| FEATURE | Location/Qualifiers | |
| misc_feature | 1..20 | |
| | note = Synthetic Oligonucleotide | |
| source | 1..20 | |
| | mol_type = other DNA | |
| | organism = synthetic construct | |
| modified_base | 6 | |
| | mod_base = OTHER | |
| | note = uracil | |
| SEQUENCE: 75 | | |
| ctagtttggt cgatgaggct | | 20 |
| | | |
| SEQ ID NO: 76 | moltype = DNA  length = 425 | |
| FEATURE | Location/Qualifiers | |
| source | 1..425 | |
| | mol_type = unassigned DNA | |
| | organism = Human rhinovirus | |
| SEQUENCE: 76 | | |
| ggtgtgtgaa tagactctaa cagggttgaa gctgtagcac tcgttatccg cacaactact | | 60 |
| acgcgaatgt tagtaacacc ctctaggtat agtgggattt cgctccgcag aaacccatc | | 120 |
| tgtagattag ggtaatgagg ctacacagac cccactggcg acagtggtgt agcctgcgtg | | 180 |
| gtgcccctacc tggggtttct cacccagga ttccacttta ctgacagggt gtgaaggcgc | | 240 |
| tagtgtgcta gttgtgagtc ctccggtccc tgaatgtggc taatcctaac cccgtggcca | | 300 |
| tttcatgtaa tccaacatgc aggtggtcgt aacgagcaat cacgggatgg aaccaactac | | 360 |
| tttgggtaac cgtgtttcct gttttacttt aatgtgtgtc ttatggttac aattatagag | | 420 |
| taacc | | 425 |
| | | |
| SEQ ID NO: 77 | moltype = DNA  length = 29 | |
| FEATURE | Location/Qualifiers | |
| misc_feature | 1..29 | |
| | note = Synthetic Oligonucleotide | |
| source | 1..29 | |
| | mol_type = other DNA | |
| | organism = synthetic construct | |
| SEQUENCE: 77 | | |
| ccatctgtag rtyrgggyaa tgrggctac | | 29 |
| | | |
| SEQ ID NO: 78 | moltype = DNA  length = 23 | |
| FEATURE | Location/Qualifiers | |
| misc_feature | 1..23 | |
| | note = Synthetic Oligonucleotide | |
| source | 1..23 | |
| | mol_type = other DNA | |
| | organism = synthetic construct | |
| modified_base | 12 | |
| | mod_base = OTHER | |
| | note = uracil | |
| SEQUENCE: 78 | | |
| gtagattagg gtaatgaggc tac | | 23 |
| | | |
| SEQ ID NO: 79 | moltype = DNA  length = 21 | |
| FEATURE | Location/Qualifiers | |
| misc_feature | 1..21 | |
| | note = Synthetic Oligonucleotide | |
| source | 1..21 | |
| | mol_type = other DNA | |
| | organism = synthetic construct | |
| modified_base | 12 | |
| | mod_base = OTHER | |
| | note = uracil | |
| SEQUENCE: 79 | | |
| gtagattagg gtaatgaggc t | | 21 |
| | | |
| SEQ ID NO: 80 | moltype = DNA  length = 21 | |
| FEATURE | Location/Qualifiers | |
| misc_feature | 1..21 | |
| | note = Synthetic Oligonucleotide | |
| source | 1..21 | |
| | mol_type = other DNA | |
| | organism = synthetic construct | |
| modified_base | 12 | |
| | mod_base = OTHER | |
| | note = uracil | |

```
SEQUENCE: 80
gtagatcrgg gtaatggggc t                                          21

SEQ ID NO: 81           moltype = DNA  length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 81
gtagatcrgg gyaatggggc t                                          21

SEQ ID NO: 82           moltype = DNA  length = 21
FEATURE                 Location/Qualifiers
misc_feature            1..21
                        note = Synthetic Oligonucleotide
source                  1..21
                        mol_type = other DNA
                        organism = synthetic construct
modified_base           12
                        mod_base = OTHER
                        note = uracil
SEQUENCE: 82
gtagatcrgg gtaatgrggc t                                          21

SEQ ID NO: 83           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 83
gtagatcggg gtaatggggc tac                                        23

SEQ ID NO: 84           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 84
gtagatcggg gcaatggggc tac                                        23

SEQ ID NO: 85           moltype = DNA  length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 85
gtagatcrgg gyaatgrgg                                             19

SEQ ID NO: 86           moltype = DNA  length = 23
FEATURE                 Location/Qualifiers
misc_feature            1..23
                        note = Synthetic Oligonucleotide
source                  1..23
                        mol_type = other DNA
                        organism = synthetic construct
SEQUENCE: 86
gtagatcrgg gyaatgrggc tac                                        23

SEQ ID NO: 87           moltype = DNA  length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 87
agcctgcgtg gyksccwrcc                                            20

SEQ ID NO: 88           moltype = DNA  length = 20
FEATURE                 Location/Qualifiers
misc_feature            1..20
```

```
                        note = Synthetic Oligonucleotide
source                  1..20
                        mol_type = other DNA
                        organism = synthetic construct
SEQUENCE: 88
agccygcgtg gtgcccygcc                                                    20

SEQ ID NO: 89           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
modified_base           2
                        mod_base = OTHER
                        note = uracil
SEQUENCE: 89
ctgcgtggtg cccygcc                                                       17

SEQ ID NO: 90           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
modified_base           14
                        mod_base = OTHER
                        note = uracil
SEQUENCE: 90
cygcgtggtg ccctgcc                                                       17

SEQ ID NO: 91           moltype = DNA  length = 14
FEATURE                 Location/Qualifiers
misc_feature            1..14
                        note = Synthetic Oligonucleotide
source                  1..14
                        mol_type = other DNA
                        organism = synthetic construct
SEQUENCE: 91
agccygcgtg gtgc                                                          14

SEQ ID NO: 92           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 92
agcctgcgtg gcggcca                                                       17

SEQ ID NO: 93           moltype = DNA  length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 93
agccygcgtg gtgccc                                                        16

SEQ ID NO: 94           moltype = DNA  length = 17
FEATURE                 Location/Qualifiers
misc_feature            1..17
                        note = Synthetic Oligonucleotide
source                  1..17
                        mol_type = other DNA
                        organism = synthetic construct
modified_base           3
                        mod_base = OTHER
                        note = uracil
SEQUENCE: 94
cctgcgtggc tgcctgc                                                       17

SEQ ID NO: 95           moltype = DNA  length = 27
FEATURE                 Location/Qualifiers
misc_feature            1..27
```

```
                    note = Synthetic Oligonucleotide
source              1..27
                    mol_type = other DNA
                    organism = synthetic construct
SEQUENCE: 95
grttagccrc attcaggggc cggagga                                        27

SEQ ID NO: 96       moltype = DNA   length = 35
FEATURE             Location/Qualifiers
misc_feature        1..35
                    note = Synthetic Oligonucleotide
source              1..35
                    mol_type = other DNA
                    organism = synthetic construct
SEQUENCE: 96
gaaacacgga cacccaaagt agtyggtycc rtccc                               35

SEQ ID NO: 97       moltype = DNA   length = 19
FEATURE             Location/Qualifiers
misc_feature        1..19
                    note = Synthetic Oligonucleotide
source              1..19
                    mol_type = other DNA
                    organism = synthetic construct
SEQUENCE: 97
aagtagttgg tcccatccc                                                 19

SEQ ID NO: 98       moltype = DNA   length = 19
FEATURE             Location/Qualifiers
misc_feature        1..19
                    note = Synthetic Oligonucleotide
source              1..19
                    mol_type = other DNA
                    organism = synthetic construct
SEQUENCE: 98
aagtagttgg ttccatccc                                                 19

SEQ ID NO: 99       moltype = DNA   length = 19
FEATURE             Location/Qualifiers
misc_feature        1..19
                    note = Synthetic Oligonucleotide
source              1..19
                    mol_type = other DNA
                    organism = synthetic construct
SEQUENCE: 99
aagtagtcgg tcccatccc                                                 19

SEQ ID NO: 100      moltype = DNA   length = 19
FEATURE             Location/Qualifiers
misc_feature        1..19
                    note = Synthetic Oligonucleotide
source              1..19
                    mol_type = other DNA
                    organism = synthetic construct
SEQUENCE: 100
aagtagttgg tcccgtccc                                                 19

SEQ ID NO: 101      moltype = DNA   length = 549
FEATURE             Location/Qualifiers
source              1..549
                    mol_type = unassigned DNA
                    organism = Human rhinovirus
SEQUENCE: 101
ttcctaatgt acccacccta aaacttccta cccaagtaac gttagaagtt tcatcaacaa    60
gtacaatagg aagcatcaca tccagtggtg ttttgtacaa gcacttctgt ttccccggag   120
cgaggtatag gctgtaccca ctgccgaaag cctttaaccg ttatccgcca accaactacg   180
taaaagctag tatcatcatg ttttaaaata ggcgttcgat caggtggatc cccctccac   240
tagtttggtc gatgaggcta ggaactcccc acgggtgacc gtgtcctagc ctgcgtggcg   300
gccaacccag cttctgctgg gacgccttt tatggacatg gtgtgaagac tcgcatgtgc   360
ttggttgtga ctcctccggc ccctgaatgc ggctaacctt aaccccggag ccctgtgttg   420
caatccagta acattagggt cgtaatgagc aatttcggga cgggaccgac tactttgggt   480
gtccgtgttt ctcatttttc ttattattgt cttatggtca cagcatatat ataacgtata   540
tactgtgat                                                          549

SEQ ID NO: 102      moltype = DNA   length = 22
FEATURE             Location/Qualifiers
misc_feature        1..22
                    note = Synthetic Oligonucleotide
source              1..22
```

```
                        mol_type = other DNA
                        organism = synthetic construct
SEQUENCE: 102
cactagtttg gycgatgagg ct                                              22

SEQ ID NO: 103          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 103
ctagtytggt cgatgaggc                                                  19

SEQ ID NO: 104          moltype = DNA   length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 104
ctagtytggt cgatgagg                                                   18

SEQ ID NO: 105          moltype = DNA   length = 16
FEATURE                 Location/Qualifiers
misc_feature            1..16
                        note = Synthetic Oligonucleotide
source                  1..16
                        mol_type = other DNA
                        organism = synthetic construct
SEQUENCE: 105
gtytggtcga tgaggc                                                     16

SEQ ID NO: 106          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 106
tagtytggtc gatgaggct                                                  19

SEQ ID NO: 107          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
modified_base           5
                        mod_base = OTHER
                        note = uracil
SEQUENCE: 107
tagtttggtc gatgaggct                                                  19

SEQ ID NO: 108          moltype = DNA   length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 108
rcattcaggg gccggagg                                                   18

SEQ ID NO: 109          moltype = DNA   length = 20
FEATURE                 Location/Qualifiers
misc_feature            1..20
                        note = Synthetic Oligonucleotide
source                  1..20
                        mol_type = other DNA
                        organism = synthetic construct
SEQUENCE: 109
agcctgcgtg gcggccarcc                                                 20

SEQ ID NO: 110          moltype = DNA   length = 17
```

```
FEATURE          Location/Qualifiers
misc_feature     1..17
                 note = Synthetic Oligonucleotide
source           1..17
                 mol_type = other DNA
                 organism = synthetic construct
modified_base    3
                 mod_base = OTHER
                 note = uracil
SEQUENCE: 110
cctgcgtggc tgcctrc                                              17

SEQ ID NO: 111   moltype = DNA  length = 17
FEATURE          Location/Qualifiers
misc_feature     1..17
                 note = Synthetic Oligonucleotide
source           1..17
                 mol_type = other DNA
                 organism = synthetic construct
SEQUENCE: 111
ctgcgtggtg ccctacc                                              17

SEQ ID NO: 112   moltype = DNA  length = 17
FEATURE          Location/Qualifiers
misc_feature     1..17
                 note = Synthetic Oligonucleotide
source           1..17
                 mol_type = other DNA
                 organism = synthetic construct
SEQUENCE: 112
ccygcgtggc tgcctac                                              17

SEQ ID NO: 113   moltype = DNA  length = 14
FEATURE          Location/Qualifiers
misc_feature     1..14
                 note = Synthetic Oligonucleotide
source           1..14
                 mol_type = other DNA
                 organism = synthetic construct
SEQUENCE: 113
agccygcgtg gctg                                                 14

SEQ ID NO: 114   moltype = DNA  length = 16
FEATURE          Location/Qualifiers
misc_feature     1..16
                 note = Synthetic Oligonucleotide
source           1..16
                 mol_type = other DNA
                 organism = synthetic construct
SEQUENCE: 114
agccygcgtg gctgcc                                               16

SEQ ID NO: 115   moltype = DNA  length = 27
FEATURE          Location/Qualifiers
misc_feature     1..27
                 note = Synthetic Oligonucleotide
source           1..27
                 mol_type = other DNA
                 organism = synthetic construct
SEQUENCE: 115
grttagccrc attcrggrgc cggagga                                   27

SEQ ID NO: 116   moltype = DNA  length = 18
FEATURE          Location/Qualifiers
misc_feature     1..18
                 note = Synthetic Oligonucleotide
source           1..18
                 mol_type = other DNA
                 organism = synthetic construct
SEQUENCE: 116
gcattcaggg gccggagg                                             18

SEQ ID NO: 117   moltype = DNA  length = 26
FEATURE          Location/Qualifiers
misc_feature     1..26
                 note = Synthetic Oligonucleotide
source           1..26
                 mol_type = other DNA
                 organism = synthetic construct
```

| | | |
|---|---|---|
| SEQUENCE: 117 | | |
| gaaacacgga cacccaaagt agtygg | | 26 |
| | | |
| SEQ ID NO: 118 | moltype = DNA length = 29 | |
| FEATURE | Location/Qualifiers | |
| misc_feature | 1..29 | |
| | note = Synthetic Oligonucleotide | |
| source | 1..29 | |
| | mol_type = other DNA | |
| | organism = synthetic construct | |
| SEQUENCE: 118 | | |
| gaaacacgga cacccaaagt agtyggtcc | | 29 |
| | | |
| SEQ ID NO: 119 | moltype = DNA length = 19 | |
| FEATURE | Location/Qualifiers | |
| misc_feature | 1..19 | |
| | note = Synthetic Oligonucleotide | |
| source | 1..19 | |
| | mol_type = other DNA | |
| | organism = synthetic construct | |
| SEQUENCE: 119 | | |
| aagtagtcgg tcccgtccc | | 19 |
| | | |
| SEQ ID NO: 120 | moltype = DNA length = 576 | |
| FEATURE | Location/Qualifiers | |
| source | 1..576 | |
| | mol_type = unassigned DNA | |
| | organism = Human rhinovirus | |
| SEQUENCE: 120 | | |
| tggatttccc acaggagtgg tactctgtta ttacggtaac tttgtacgcc agtttatct | | 60 |
| cccttccccc atgtaactta gaagtttttc acaaagacca atagccggta atcagccaga | | 120 |
| ttactgaagg tcaagcactt ctgtttcccc ggtcaatgtt gatatgctcc aacagggcaa | | 180 |
| aaacaactgc gatcgttatc cgcaaagcgc ctacgcaaag cttagtagca tctttgaaat | | 240 |
| cgtttggctg gtcgatccgc catttcccct ggtagacctg gcagatgagg ctagaaatac | | 300 |
| cccactggcg acagtgttct agcctgcgtg gctgcctgca caccctatgg gtgtgaagcc | | 360 |
| aaacaatgga caaggtgtga agagcccgt gtgctcgctt tgagtcctcc ggcccctgaa | | 420 |
| tgtggctaac cttaaccctg cagctagagc acgtaaccca acgtgtatct agtcgtaatg | | 480 |
| agcaattgcg ggatgggacc aactactttg ggtgtccgtg tttcacttttt tcctttatat | | 540 |
| ttgcttatgg tgacaatata tacaatatat atattg | | 576 |
| | | |
| SEQ ID NO: 121 | moltype = DNA length = 19 | |
| FEATURE | Location/Qualifiers | |
| misc_feature | 1..19 | |
| | note = Synthetic Oligonucleotide | |
| source | 1..19 | |
| | mol_type = other DNA | |
| | organism = synthetic construct | |
| SEQUENCE: 121 | | |
| yrgrcytggc agatgrggc | | 19 |
| | | |
| SEQ ID NO: 122 | moltype = DNA length = 19 | |
| FEATURE | Location/Qualifiers | |
| misc_feature | 1..19 | |
| | note = Synthetic Oligonucleotide | |
| source | 1..19 | |
| | mol_type = other DNA | |
| | organism = synthetic construct | |
| SEQUENCE: 122 | | |
| taracctggc agatgrggc | | 19 |
| | | |
| SEQ ID NO: 123 | moltype = DNA length = 19 | |
| FEATURE | Location/Qualifiers | |
| misc_feature | 1..19 | |
| | note = Synthetic Oligonucleotide | |
| source | 1..19 | |
| | mol_type = other DNA | |
| | organism = synthetic construct | |
| SEQUENCE: 123 | | |
| tagacctggc agatggggc | | 19 |
| | | |
| SEQ ID NO: 124 | moltype = DNA length = 19 | |
| FEATURE | Location/Qualifiers | |
| misc_feature | 1..19 | |
| | note = Synthetic Oligonucleotide | |
| source | 1..19 | |
| | mol_type = other DNA | |
| | organism = synthetic construct | |
| SEQUENCE: 124 | | |
| tagacctggc agatgrggc | | 19 |

```
SEQ ID NO: 125          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 125
taracctggc agatggggc                                                    19

SEQ ID NO: 126          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 126
taracctggt agatgrggc                                                    19

SEQ ID NO: 127          moltype = DNA   length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 127
taracctggc agatgrg                                                      17

SEQ ID NO: 128          moltype = DNA   length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 128
taracctggc agatgrgg                                                     18

SEQ ID NO: 129          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 129
caracctggc agatgrggc                                                    19

SEQ ID NO: 130          moltype = DNA   length = 15
FEATURE                 Location/Qualifiers
misc_feature            1..15
                        note = Synthetic Oligonucleotide
source                  1..15
                        mol_type = other DNA
                        organism = synthetic construct
SEQUENCE: 130
cctgccagat grggc                                                        15

SEQ ID NO: 131          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 131
wgcctgcgyg gckgccwrc                                                    19

SEQ ID NO: 132          moltype = DNA   length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 132
```

```
ccygcgcggc tgcctrc                                                    17

SEQ ID NO: 133          moltype = DNA   length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 133
ccygcgtggc tgcctrc                                                    17

SEQ ID NO: 134          moltype = DNA   length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 134
ccygcgtggc tgcctgc                                                    17

SEQ ID NO: 135          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 135
wgccygcgtg gctgcctgc                                                  19

SEQ ID NO: 136          moltype = DNA   length = 19
FEATURE                 Location/Qualifiers
misc_feature            1..19
                        note = Synthetic Oligonucleotide
source                  1..19
                        mol_type = other DNA
                        organism = synthetic construct
SEQUENCE: 136
agccygcgtg gctgcctgc                                                  19

SEQ ID NO: 137          moltype = DNA   length = 27
FEATURE                 Location/Qualifiers
misc_feature            1..27
                        note = Synthetic Oligonucleotide
source                  1..27
                        mol_type = other DNA
                        organism = synthetic construct
SEQUENCE: 137
grttagccgc attcrggrgc cggagga                                         27

SEQ ID NO: 138          moltype = DNA   length = 46
FEATURE                 Location/Qualifiers
misc_feature            1..46
                        note = Synthetic Oligonucleotide
source                  1..46
                        mol_type = other DNA
                        organism = synthetic construct
SEQUENCE: 138
tacatgcaca tckcsggvca ggaygcytcg gagtacctga gccccg                    46

SEQ ID NO: 139          moltype = DNA   length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 139
acgcctcgga gtacctgagc cc                                              22

SEQ ID NO: 140          moltype = DNA   length = 24
FEATURE                 Location/Qualifiers
misc_feature            1..24
                        note = Synthetic Oligonucleotide
source                  1..24
                        mol_type = other DNA
                        organism = synthetic construct
```

```
SEQUENCE: 140
cggggctcag gtactccgag gcgt                                              24

SEQ ID NO: 141          moltype = DNA  length = 22
FEATURE                 Location/Qualifiers
misc_feature            1..22
                        note = Synthetic Oligonucleotide
source                  1..22
                        mol_type = other DNA
                        organism = synthetic construct
SEQUENCE: 141
gtkgcrcggg craaytgcac ca                                                22

SEQ ID NO: 142          moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 142
gtkgcrcggg cgaactgc                                                     18

SEQ ID NO: 143          moltype = DNA  length = 17
FEATURE                 Location/Qualifiers
misc_feature            1..17
                        note = Synthetic Oligonucleotide
source                  1..17
                        mol_type = other DNA
                        organism = synthetic construct
SEQUENCE: 143
gtggcgcggg caaactg                                                      17

SEQ ID NO: 144          moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 144
gtkgcrcggg craactgc                                                     18

SEQ ID NO: 145          moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 145
gtggcrcggg craactgc                                                     18

SEQ ID NO: 146          moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 146
gtkgcgcggg craactgc                                                     18

SEQ ID NO: 147          moltype = DNA  length = 18
FEATURE                 Location/Qualifiers
misc_feature            1..18
                        note = Synthetic Oligonucleotide
source                  1..18
                        mol_type = other DNA
                        organism = synthetic construct
SEQUENCE: 147
gtggcgcggg craactgc                                                     18

SEQ ID NO: 148          moltype = DNA  length = 18
FEATURE                 Location/Qualifiers
misc_feature            1..18
                        note = Synthetic Oligonucleotide
source                  1..18
                        mol_type = other DNA
```

```
                         organism = synthetic construct
SEQUENCE: 148
gtggcrcggg cgaactgc                                            18

SEQ ID NO: 149           moltype = DNA  length = 18
FEATURE                  Location/Qualifiers
misc_feature             1..18
                         note = Synthetic Oligonucleotide
source                   1..18
                         mol_type = other DNA
                         organism = synthetic construct
SEQUENCE: 149
gtkgcgcggg cgaactgc                                            18

SEQ ID NO: 150           moltype = DNA  length = 13293
FEATURE                  Location/Qualifiers
source                   1..13293
                         mol_type = unassigned DNA
                         organism = Human Metapneumovirus
SEQUENCE: 150
acgcgaaaaa aacgcgtata aattaaattc caaacaaaac gggacaaata aaaatgtctc  60
ttcaagggat tcacctaagt gatctatcat ataaacatgc tatattaaaa gagtctcaat  120
acacaataaa aagagatgta ggcaccacaa ctgcagtgac accttcatca ttacaacaag  180
aaataacact tttgtgtggg gaaatacttt acactaaaca cactgattac aaatatgctg  240
ctgagatagg aatacaatat atttgcacag ctctaggatc agaaagagta caacagattt  300
tgagaaactc aggtagtgaa gttcaggtgg ttctaaccaa aacatactcc ttagggaaag  360
gcaaaaacag taaaggggaa gagctgcaga tgttagatat acatggagtg gaaaagagtt  420
ggatagaaga aatagacaaa gaggcaagaa agacaatggt aactttgctt aaggaatcat  480
caggtaacat cccacaaaac cagagacctt cagcaccaga cacaccaata attttattat  540
gtgtaggtgc cctaatattc actaaactag catcaacaat agaagttgga ttagagacta  600
cagttagaag agctaataga gtgctaagtg atgcactcaa aagataccca aggatagata  660
taccaaagat tgctagatct ttttatgaac tatttgaaca aaaagtgtac tacagaagtt  720
tattcattga gtacggaaaa gctttaggct catcttcaac aggaagcaaa gcagaaagtt  780
tgtttgtaaa tatatttatg caagcttatg gagctggcca aacactgcta aggtggggtg  840
tcattgccag atcatccaac aacataatgc tagggcatgt atctgtgcaa tctgaattga  900
agcaagttac agaggtttat gacttggtga gagaaatggg tcctgaatct gggcttttac  960
atctaagaca aagtccaaag gcagggctgt tatcattggc caattgcccc aatttgcta  1020
gtgttgttct tggcaatgct tcaggtctag gcataatcgg aatgtacaga gggagagtac  1080
caaacacaga gctattttct gcagcagaaa gttatgccag aagcttaaaa gaaagcaata  1140
aaatcaactt ctcttcgtta gggcttacag atgaagaaaa agaagctgca gaacacttct  1200
taaacatgag tggtgacaat caagatgatt atgagtaatt aaaaaactgg gacaagtcaa  1260
aatgtcattc cctgaaggaa aggatattct gttcatgggt aatgaagcag caaaaatagc  1320
cgaagctttc cagaaatcac tgaaaaaatc aggtcacaag agaactcaat ctattgtagg  1380
ggaaaaagtt aacactatat cagaaactct agaactacct accatcagca aacctgcacg  1440
atcatctaca ctgctggaac caaaattggc atgggcagac aacagcggaa tcaccaaaat  1500
cacagaaaaa ccagcaacca aaacaacaga tcctgttgaa gaagaggaat tcaatgaaaa  1560
gaaagtgtta ccttccagtg atgggaagac tcctgcagag aaaaaatcaa agttttcaac  1620
cagtgtaaaa aagaaagttt cctttacatc aaatgaacca gggaaataca ccaaactaga  1680
gaaagatgcc ctagatttgc tctcagacaa tgaggaagaa gacgcagaat cctcaatcct  1740
aacttttgag gagaaagata catcatcact aagcattgaa gctagactag aatctataga  1800
agagaagttg agcatgatat taggactgct tcgtacactt aacattgcaa cagcaggacc  1860
aacagctgca cgagatggaa ttagggatgc aatgattggt ataagagaag agctaatagc  1920
agagataatt aaggaagcca agggaaaagc agctgaaatg atggaagaag agatgaatca  1980
aagatcaaaa ataggaaatg gcagtgtaaa actaaccgag aaggcaaaag agctcaacaa  2040
aattgttgaa gacgagagca caagcggtga atcagaagaa gaagaagaac caaaagaaac  2100
tcaggataac aatcaaggag aagatattta tcagttaatc atgtagttta ataaaaataa  2160
acaatgggac aagtcaagat ggagtcctat ctagtagaca cttatcaagg cattccatat  2220
acagctgctg ttcaagttga cctggtagaa aaagatttac tgccagcaag tttgacaata  2280
tggtttcctt tatttcaggc caacacacca ccagcagttc tgcttgatca gctaaaaacc  2340
ttgacaataa caactctgta tgctgcatca cagaatggtc caatactcaa ggtaaatgca  2400
tctgcccaag gtgctgccat gtctgtactt cccaaaaaat tcgaggtaaa tgcaactgta  2460
gcacttgatg aatacagtaa acttgatttt gacaagctga cggtctgcga tgttaaaaca  2520
gtttatttga caactatgaa accgtacggg atggtgtcaa aatttgtgag ttcagccaaa  2580
tcagttggca aaaagacaca tgatctaatt gcactatgtg acttcatgga cctagagaaa  2640
aatatacctg tgacaatacc agcattcata aagtcagttt caatcaaaga gagtgaatca  2700
gccactgttg aagctgcaat aagcagcgaa gccgaccaag ccttgacaca agccaagatt  2760
gcgccctatg caggactaat tatgatcatg accatgaaca atccaaaagg tatattcaag  2820
aaactagggg ctggaacaca agtgatagta gagctggggg catatgttca ggctgagagc  2880
atcagtagga tctgcaagag ctggagtcac caaggaacaa gatacgtact aaaatccaga  2940
taaaaataac tgtcttaatc aataattgct tatataactc tagagattaa taagcttatt  3000
attatagtta tataaaaata aattagaatt agaagggcat caatagaaag cgggacaaat  3060
aaaaatgtct tggaaagtga tgatcatcat ttcgttactc ataacacccc agcacgggct  3120
aaaggagagt tatttggaag aatcatgtag tactataact gagggatacc tcagtgtttt  3180
aagaacaggc tggtacacta atgtcttcac attagaagtt ggtgatgttg aaaatcttac  3240
atgtactgat ggacctagct taatcaaaac agaacttgat ctaacaaaaa gtgctttaag  3300
ggaactcaaa acagtctctg ctgatcagtt ggcgagagag gagcaaattg aaaatcccag  3360
acaatcaaga tttgtcttag gtgcgatagc tctcggagtt gctacagcag cagcagtcac  3420
agcaggcatt gcaatagcca aaaccataag gcttgagagt gaggtgaatg caattaaagg  3480
tgctctcaaa caaactaatg aagcagtatc cacattaggg aatggtgtgc gggtcctagc  3540
```

```
cactgcagtg agagagctaa aagaatttgt gagcaaaaac ctgactagtg caatcaacag   3600
gaacaaatgt gacattgctg atctgaagat ggctgtcagc ttcagtcaat tcaacagaag   3660
atttctaaat gttgtgcggc agttttcaga caatgcaggg ataacaccag caatatcatt   3720
ggacctgatg actgatgctg agttggccag agctgtatca tacatgccaa catctgcagg   3780
gcagataaaa ctgatgttgg agaaccgcgc aatggtaagg agaaaaggat ttggaatcct   3840
gatagggggtc tacggaagct ctgtgatttta catggttcaa ttgccgatct ttggtgtcat   3900
agatacacct tgttggatca tcaaggcagc tccctcttgc tcagaaaaaa acgggaatta   3960
tgcttgcctc ctaagagagg atcaagggtg gtattgtaaa aatgcaggat ctactgttta   4020
ctacccaaat gaaaaagact gcgaaacaag aggtgatcat gttttttgtg acacagcagc   4080
agggatcaat gttgctgagc aatcaagaga atgcaacatc aacatatcta ctaccaacta   4140
cccatgcaaa gtcagcacag gaagacaccc tataagcatg gttgcactat cacctctcgg   4200
tgctttggtg gcttgctata aaggggtaag ctgctcgatt ggcagcaatt gggttggaat   4260
catcaaacaa ttacccaaag gctgctcata cataaccaac caggatgcag acactgtaac   4320
aattgacaat accgtgtatc aactaagcaa agttgaaggt gaacagcatg taataaaagg   4380
gagaccagtt tcaagcagtt ttgatcaatc aagtttcct gaggatcagt tcaatgttgc   4440
gcttgatcaa gtcttcgaaa gcattgagaa cagtcaggca ctagtggacc agtcaaacaa   4500
aattctaaac agtgcagaaa aaggaaacac tggtttcatt atcgtagtaa ttttggttgc   4560
tgttcttggt ctaaccatga tttcagtgag catcatcatc ataatcaaga aaacaaggaa   4620
gcccacagga gcacctccag agctgaatgg tgtcaccaac ggcggtttca taccacatag   4680
ttagttaatt aaaaaatggg acaaatcatc atgtctcgta aggctccatg caaatatgaa   4740
gtgcgggggca aatgcaacag agggagtgat tgcaaattca atcacaatta ctggagttgg   4800
cctgatagat atttattgtt aagatcaaat tatctcttaa atcagctttt aagaaacaca   4860
gataaggctg atggtttgtc aataatatca ggagcaggta gagaagatag aactcaagac   4920
tttgttcttg gttctactaa tgtggttcaa gggtacattg atgacaacca aggaataacc   4980
aaggctgcag cttgctatag tctacacaac ataatcaagc aactacaaga aacagaagta   5040
agacaggcta gagacaacaa gctttctgat agcaaacatg tggcgctcca caacttgata   5100
ttatcctata tggagatgag caaaactcct gcatctctaa tcaacaacct aaagaaacta   5160
ccaagggaaa aactgaagaa attagcaaga ttaataattg atttatcagc aggaactgac   5220
aatgactctt catatgcctt gcaagacagt gaaagcacta atcaagtgca gtaaacatgg   5280
tcccaaattc attaccatag aggcagatga tatgatatgg actcacaaag aattaaaaga   5340
aacactgtct gatgggatag taaaatcaca caccaatatt tatagttgtt acttagaaaa   5400
tatagaaata atatatgtta aaacttactt aagttagtaa aaaataaaaa tagaatggga   5460
taaatgacaa tgaaaacatt agatgtcata aaaagtgatg gatcctcaga aacgtgtaat   5520
caactcaaaa aaataataaa aaaacactca ggtaaagtgc ttattgcact aaaactgata   5580
ttggccttac tgacattttt cacagcaaca atcactgtca actatataaa agtagaaaac   5640
aatttgcagg catgtcaacc aaaaaatgaa tcagacaaaa aggtcacaaa gccaaatacc   5700
acatcaacaa caatcagacc cacacccgat ccaactgtag tacatcattt gaaaaggctg   5760
attcagagac acaccaactc tgtcacaaaa gacagcgata cttgttggag aatacacaag   5820
aatcaagtaa caaatataaa aatatacaag ttcttatgct ctgggttcac aaattcaaaa   5880
ggtacagatt gtgaggaacc aacagcccta tgcgacaaaa agttaaaaac catagtagaa   5940
aaacatagaa aagcagaatg tcactgtcta catacaaccg agtgggggtg ccttcatccc   6000
taaaataaca cggcttttcaa cattaaaatc agaacaacct ccaccaggt ctatcaatac   6060
agtggtttag ccatttaaaa accgaatatt atctaggctg cacgacactt tgcaataaa   6120
tgcaatagtc aatagttaaa ccactgctgc aaactcatcc ataatataat cactgagtaa   6180
tacaaaacaa gaaaatggga caagtggcta tggaagtaag agtggagaac attcgagcga   6240
tagacatgtt caaagcaaag ataaaaaacc gtataagaag cagcaggtgc tatagaaatg   6300
ctacactgat ccttattgga ctaacagcgt taagcatgcc actaatatt ttcctgatca   6360
tcgatcatgc aacattaaga aacatgatca aaacagaaaa ctgtgctaac atgccgtcgg   6420
cagaaccaag caaaaagacc ccaatgacct ccacagcagg cccaaacacc aaacccaatc   6480
cacagcaagc aacacagtgg accacagaga actcaacatc cccagtagca accccagagg   6540
gccatccata cacagggaca actcaaacat cagacacaac agctcccccag caaaccagg   6600
acaaacacac agcaccgcta aaatcaacca atgaacagat cacccagaca accagagga   6660
aaagacaat cagagcaaca acccaaaaaa gggaaaaagg aaaagaaaac acaaaccaaa   6720
ccacaagcac agctgcaacc caaacaacca acaccaccaa ccaaatcaga aatgcaagtg   6780
agacaatcac aacatccgac agacccagaa ctgacaccac aacccaaagc agcgaacaga   6840
caacccgggc aacagaccca agctccccac cacaccatgc atagagaggt gcaaaactca   6900
aatgagcaca acacacaaac atcccatcca agtagttaac aaaaaaccac aaaataacct   6960
tgaaaaccaa aaaaccaaaa cataaaccca gacccagaaa aacatagaca ccatatggaa   7020
ggttctagca tatgccaccaa tgagatggca tctgttcatg tatcaatagc accaccatca   7080
ttcaaggaat aagaagaggc gaaaatttaa gggataaatg acaatggatc ccttttgtga   7140
atctactgtt aatgttttatc tccctgattc atatctcaaa ggagtaatat cttttagtga   7200
aaccaatgca attggatcat gtcttttgaa aagaccctat ctaaaaatg acaacactgc   7260
caaagttgct gtagaaaacc ctgttgttga acatgtgagg cttagaaatg cagtcatgac   7320
caaaatgaag atatcagatt aaaagtggt tgaaccagtt aatatgcagc atgaaatat   7380
gaaaaatata catagttgtg agcttacatt attaaaacaa ttcttaacga aagcaaaaa   7440
cattagctct ctaaaattaa atatgatatg tgattggtta cagttaaaat ccacttcaga   7500
taacacatca attctcaatt ttatagatgt ggagttcata cccgtttggg taagcaattg   7560
gttcagtaac tggtatataatc tcaataaatt aatcttagag tttagaagag aagaagtaat   7620
aagaactggt tcaattttat gtagatcact aggcaagtta gtttttattg tatcatctta   7680
tggatgtgta gtaaaagca acaaaagtaa aagagtgagc tttttcacct ataaccaact   7740
gttaacatgg aaagatgtga tgttaagtag attcaatgca aactttttgta tatgggtaag   7800
taacaacctg aacaaaatc aagaaggact aggacttaga agcaatctgc aaggtatgtt   7860
aaccaataaa ttatatgaaa ctgttgatta catgctaagc ctatgctgca atgaaggatt   7920
ctctctggtg aagagtttg aaggatttat tgtgagtcaa attctaaaaa ttactgactg   7980
tgctcagttc agtactaggt ttaggaatac tttattgaat gggttaactg aacaattatc   8040
agtgttgaaa gctaagaaca gatctagagt tcttggaact atattagaaa acaacaatta   8100
ccctatgtac gaagtagtac ttaaattatt aggggacacc ttgaaaagca taagttatt   8160
aattaacaag aatttagaaa atgctgcaga attatattat atattcagaa tttttggaca   8220
ccctatggta gatgagaggg aagcaatgga tgctgttaaa ttaaacaatg agattacaaa   8280
```

```
aattcttaaa ttagagagtt taacagaact aagaggagca tttatactaa gaattataaa   8340
agggtttgta gacaataata aaagatggcc taaaattaag aatttaaaag tgctcagcaa   8400
aagatgggct atgtatttca aagctaaaag ttaccctagc caacttgagc taagtgtaca   8460
agatttttta gaacttgctg cagtacaatt tgagcaggaa ttctctgtac ctgaaaaaac   8520
caaccttgag atggtattaa atgataaagc aatatcacct ccaaaaaagc taatatggtc   8580
tgtatatcca aaaaactacc tgcctgaaac tataaaaaat caatatttag aagaggcttt   8640
caatgcaagt gacagccaaa gaacaaggag agtcttagaa ttttacttaa aagattgtaa   8700
atttgatcaa aaagaactta aacgttatgt aattaaacaa gagtatctga atgacaaaga   8760
ccacattgtc tcgttaactg ggaaggaaag agaattaagt gtaggtagga tgtttgcaat   8820
gcaaccagga aaacaaagac agatacagat attagctgag aaacttctag ctgataatat   8880
tgtacctttt ttcccagaaa cttttaacaaa gtatggtgac ttagatctcc aaagaattat   8940
ggaaataaaa tcagaacttt cttccattaa aactagaaag aatgatagct acaacaatta   9000
tattgcaagg gcctctatag taacagactt aagtaagttc aatcaggcct ttagatatga   9060
aaccacagct atatgtgcag atgtagctga tgagttacat gggacacaaa gcttattctg   9120
ttggttacat cttattgttc ccatgactac aatgatatgt gcatacagac atgcaccacc   9180
agaaacaaaa ggggaatatg atatagacaa aatacaagag caaagcggat tatacagata   9240
tcatatggga gggattgaag ggtggtgcca gaagttatgg acaatggaag caatatcctt   9300
gttagatgtg gtatctgtga agactcgctg tcagatgacc tctctattaa acggagcaa   9360
tcagtcaata gatgttagta aaccagtaaa attgtctgaa ggtatagatg aagtaaaagc   9420
agactatagc ttagcaatta gaatgcttaa agaaataaga gatgcttata aaaacattgg   9480
tcataaactc aaagaaggtg aaacatatat atcaagggat ctccaattta taagtaaggt   9540
gattcaatct gaaggagtca tgcatcctac ccctataaaa aagatattaa gagtaggtcc   9600
ttggataaat acaatactag atgatattaa aaccagtgca gaatcaatag gaagtctatg   9660
tcaagaacta gaattcagag gggagagtat actagttagc ttgatattaa ggaatttctg   9720
gctgtataac ttgtacatgt atgagtcaaa acagcaccca ttagctggga agcaactgtt   9780
caagcaattg aacaaaacat taacatctgt gcagagattt tttgaactga agaaagaaaa   9840
tgatgtggtt gacctatgga tgaatatacc aatgcagttt ggaggggggg atccagtagt   9900
tttttacaga tctttttaca gaaggactcc cgatttccta actgaagcaa tcagccatgt   9960
ggatttactg ttaaaagtgt caaacaatat caaagatgag actaagatac gatttttcaa  10020
agccttatta tctatagaaa agaatgaacg tgctacatta acaacactaa tgagagaccc  10080
tcaggcagta ggatcagaac gacaagctaa ggtaacaagt gatataaata gaacagcagt  10140
taccagcata ctgagtctat ctccgaatca gctcttctgt gatagtgcta tacattatag  10200
tagaaatgag gaagaagttg ggatcattgc agacaacata cacctgtct atcctcatgg  10260
gctgagagtg ctctatgaat cactacctt tcataaggct gaaaaggttg tcaaatatgat  10320
atcaggcaca aagtctataa ctaatctatt acagagaaca tctgctatca atggtgaaga  10380
tattgataga gcagtgtcta tgatgttaga gaacttaggg ttgttatcta gaatattgtc  10440
agtaataatt aatagtatag aaataccaat caagtccaat ggcagattga tatgctgtca  10500
aatttccaag accttgagag aaaaaatcatg gaacaatatg gaaatagtag gagtgacatc  10560
tcctagtatt gtgacatgta tggatgttgt gtatgcaact agttctcatt taaaaggaat  10620
aattattgaa aaattcagta ctgacaagac cacaagaggt cagaggggac caaaaagccc  10680
ctgggtagga tcaagcactc aagagaaaaa attggttcct gtttataata gacaaattct  10740
ttcaaaacaa caaaaagagc aactggaagc aataggggaaa atgaggtggg tgtacaaagg  10800
aactccaggg ctaagaagat tgctcaacaa gatttgccta ggaagcttag gtattagcta  10860
taaatgtgtg aaacctttat taccaagatt catgagtgta aacttcttac ataggttatc  10920
tgttagtagt agacccatgg aattcccagc ttctgttcca gcttacagga caacaaatta  10980
ccattttgac actagtccaa tcaaccaagc attaagtgag aggttcggga acgaagacat  11040
taatttagtg ttccaaaatg caatcagctg cggaattagt ataatgagtg ttgtagaaca  11100
gttaactgt agaagcccaa aacaattagt cctaatccct caattagaag agatagatat  11160
tatgcctcct cctgtatttc aaggaaaatt caattataaa ctagttgata agataacctc  11220
cgatcaacac atcttcagtc ctgacaaaat agacatatta acactaggga agatgcttat  11280
gcctaccata aaaggtcaaa aaactgatca gttcttaaat aagagagaaa actatttca  11340
tggaaataat ttaattgaat ctttatctgc agcacttgca tgccactggt gtgggatatt  11400
aacagaacag tgcatagaaa acaatatctt taggaaagat tggggtgatg ggttcatctc  11460
agatcatgcc ttcatggatt tcaaggtatt tctatgtgta tttaaaacca aacttttatg  11520
tagttgggga tctcaaggaa agaatgttaa agatgaagat ataatagatg aatccattga  11580
caaattatta agaattgaca acaccttttg gagaatgttc agcaaagtca tgtttgaatc  11640
aaaagtcaaa aaaagaataa tgttatatga tgtgaaattc ctatcattag taggttatat  11700
aggatttaaa aactggttta tagaacagtt aagagtggta gaattgcatg aggtaccttg  11760
gattgtcaat gctgaaggag agttagttga aattaaatca atcaaaattt atctgcagtt  11820
aatagaacaa agtctatctt tgagaataac tgtattgaat tatacagaca tggcacatgc  11880
tcttacacga ttaattagga aaaaattgat gtgtgataat gcactcttta atccaagttc  11940
atcaccaatg tttaatctaa ctcaggttat tgatcccaca acacaactag actattttcc  12000
taggataata tttgagaggt taaaaagtta tgataccagt tcagactaca caaagggaaa  12060
gttaacaagg aattacatga cattattacc atggcaacag gtaaacaggt acaatttttgt  12120
ctttagttct acaggttgta aagtcagttt gaagacatgc atcgggaaat tgataaagga  12180
tttaaatcct aaagttcttt actttattgg agaaggagca ggtaactgga tggcaagaac  12240
agcatgtgaa tatcctgata taaatttgt atataggagt tttaaaggatg accttgatca  12300
ccattaccca ttagaaatatc aaagggtaat aggtgatcta aaatggggta tagatagtgg  12360
tgaaggatta tcaatggaaa ccacgatgc aactcaaaaa actcattggg acttgataca  12420
cagaatagt aaagatgctt tattgataac attgtgtgat gcagaattca aaaacagaga  12480
tgatttcttt aagatggtaa tccttttggag aaaaacatga ttatcttgta gaatctgtac  12540
agcttatgga acagatcttt acttatttgc aaagtatcat gcggtggact gcaatataaa  12600
attaccattt tttgtaagat ctgtagctac ttttattatg caaggaagca aattatcagg  12660
gtcagaatgt gaaatcaaat tccaaatga gaatagcagt gtgtaatgat ttctatgcct caaagaaact  12780
ggacaacaaa tcaattgaag caactgcaa atctcttcta tcaggattga gaataccttat  12840
aaacaaaaag gagttaaata gacaaaagaa attgttaaca ctacaaagta accattcttc  12900
tatagcaaca gttggcggca gtaagattat agaatccaaa tggttaaaga ataaagcaag  12960
tacaataatt gattggttag agcatattt gaattctcca aaaggtgaat taactatga  13020
```

```
tttctttgaa gcattagaga acacataccc caatatgatc aagcttatag ataatttggg   13080
aaatgcagaa ataagaaac  taatcaaggt cactgggtat atgcttgtga gtaagaagta   13140
ataataatga taatgattaa ccataatctc acacaactga gaaataatc  gtctaacagt   13200
ttagttgatc attagttatt taaaattata aatagtaac  taactgataa aaaatcagaa   13260
attgaaattg aatgtatacg gttttttttgc cgt                               13293

SEQ ID NO: 151          moltype = DNA   length = 28
FEATURE                 Location/Qualifiers
misc_feature            1..28
                        note = Synthetic Oligonucleotide
source                  1..28
                        mol_type = other DNA
                        organism = synthetic construct
SEQUENCE: 151
cssccaatttt tgctagtgtt gttcttgg                                       28

SEQ ID NO: 152          moltype = DNA   length = 28
FEATURE                 Location/Qualifiers
misc_feature            1..28
                        note = Synthetic Oligonucleotide
source                  1..28
                        mol_type = other DNA
                        organism = synthetic construct
SEQUENCE: 152
cggccaattt tgctagtgtt gttcttgg                                        28

SEQ ID NO: 153          moltype = DNA   length = 24
FEATURE                 Location/Qualifiers
misc_feature            1..24
                        note = Synthetic Oligonucleotide
source                  1..24
                        mol_type = other DNA
                        organism = synthetic construct
SEQUENCE: 153
caattttgct agtgttgttc ttgg                                            24

SEQ ID NO: 154          moltype = DNA   length = 25
FEATURE                 Location/Qualifiers
misc_feature            1..25
                        note = Synthetic Oligonucleotide
source                  1..25
                        mol_type = other DNA
                        organism = synthetic construct
SEQUENCE: 154
ccaattttgc tagtgttgtt cttgg                                           25

SEQ ID NO: 155          moltype = DNA   length = 36
FEATURE                 Location/Qualifiers
misc_feature            1..36
                        note = Synthetic Oligonucleotide
source                  1..36
                        mol_type = other DNA
                        organism = synthetic construct
SEQUENCE: 155
tgcttcaggt ytaggyataa tcggaatgtw cagagg                               36

SEQ ID NO: 156          moltype = DNA   length = 36
FEATURE                 Location/Qualifiers
misc_feature            1..36
                        note = Synthetic Oligonucleotide
source                  1..36
                        mol_type = other DNA
                        organism = synthetic construct
SEQUENCE: 156
tgcttcaggt ttaggcataa tcggaatgtt cagagg                               36

SEQ ID NO: 157          moltype = DNA   length = 29
FEATURE                 Location/Qualifiers
misc_feature            1..29
                        note = Synthetic Oligonucleotide
source                  1..29
                        mol_type = other DNA
                        organism = synthetic construct
SEQUENCE: 157
tgcttcaggt ctaggtataa tcggaatgt                                       29

SEQ ID NO: 158          moltype = DNA   length = 23
FEATURE                 Location/Qualifiers
misc_feature            1..23
```

```
                        note = Synthetic Oligonucleotide
source                  1..23
                        mol_type = other DNA
                        organism = synthetic construct
SEQUENCE: 158
gcagaaaata gctctgtgtt tgg                                               23

SEQ ID NO: 159          moltype = DNA   length = 1045
FEATURE                 Location/Qualifiers
source                  1..1045
                        mol_type = unassigned DNA
                        organism = Human Metapneumovirus
SEQUENCE: 159
cacaataaag agagatgtgg gcacaacaac agcagtaaca ccctcatcat tgcaacaaga         60
aataacactg ttgtgtggag aaattctata tgctaagcat actgattaca aatatgctgc        120
agaaatagga atacaatata ttagcacagc tctagggtca gagagagtac agcagattct        180
aagaaactca ggcagtgaag tccaagcggt tttaaccaga acgtactctt tggggaaagt        240
taaaaacaat aaaggagaag atttacagat gttagacata catggagtag aaaaaagctg        300
ggtggaagag atagacaaag aagcaagaaa aacaatggca actttactta agaatcatc         360
aggcaatatt ccacaaaatc agaggccttc agcaccagac acacctataa tcttattatg        420
tgtaggtgcc ttaatattta ccaaactagc atcaactata gaagtgggat tagagaccac        480
agtcagagaa gctaaccgtg tactaagtga tgcactcaaa agatacccta gaatggacat        540
accaaaaatt gctagatcct tctatgactt atttgaacaa aaagtgtatc acagaagttt        600
gttcattgag tatggcaaag cattaggctc atcctctaca ggcagcaaag cagaaagttt        660
attcgtcaac atattcatgc aagcttatgg tgctggtcaa acaatgctga ggtgggggt         720
tatcgccagg tcatctaaca atataatgtt aggacatga tctgtacaag ccgagctgaa        780
acaggtcaca gaagtctatg acctagtgcg ggaaatgggc cctgaatctg ggctcctaca        840
tttaaggcaa agcccaaaag ctggactgtt atcccttgca aattgtccca actttgcaag        900
tgttgttctc ggcaatgcct caggcttagg cataataggg atgtatcgag ggagagtgcc        960
aaacacagaa ctattttcag cagcagaaag ctatgccaag agtttgaaag aaagtaataa       1020
aatcaacttt tcttcattag gactc                                             1045

SEQ ID NO: 160          moltype = DNA   length = 21
FEATURE                 Location/Qualifiers
misc_feature            1..21
                        note = Synthetic Oligonucleotide
source                  1..21
                        mol_type = other DNA
                        organism = synthetic construct
SEQUENCE: 160
ctttgcaagt gttgttctcg g                                                 21

SEQ ID NO: 161          moltype = DNA   length = 37
FEATURE                 Location/Qualifiers
misc_feature            1..37
                        note = Synthetic Oligonucleotide
source                  1..37
                        mol_type = other DNA
                        organism = synthetic construct
SEQUENCE: 161
tgcctcaggc ytaggcataa tmggyatgta tcghggg                                37

SEQ ID NO: 162          moltype = DNA   length = 29
FEATURE                 Location/Qualifiers
misc_feature            1..29
                        note = Synthetic Oligonucleotide
source                  1..29
                        mol_type = other DNA
                        organism = synthetic construct
SEQUENCE: 162
tcaggcttag gcataatagg tatgtatcg                                         29

SEQ ID NO: 163          moltype = DNA   length = 33
FEATURE                 Location/Qualifiers
misc_feature            1..33
                        note = Synthetic Oligonucleotide
source                  1..33
                        mol_type = other DNA
                        organism = synthetic construct
SEQUENCE: 163
cctcaggctt aggcataata ggtatgtatc gag                                    33

SEQ ID NO: 164          moltype = DNA   length = 31
FEATURE                 Location/Qualifiers
misc_feature            1..31
                        note = Synthetic Oligonucleotide
source                  1..31
                        mol_type = other DNA
                        organism = synthetic construct
```

```
SEQUENCE: 164
cctcaggctt aggcataata ggtatgtatc g                                          31

SEQ ID NO: 165          moltype = DNA  length = 33
FEATURE                 Location/Qualifiers
misc_feature            1..33
                        note = Synthetic Oligonucleotide
source                  1..33
                        mol_type = other DNA
                        organism = synthetic construct
SEQUENCE: 165
cctcaggctt aggcataata ggtatgtatc gcg                                        33

SEQ ID NO: 166          moltype = DNA  length = 33
FEATURE                 Location/Qualifiers
misc_feature            1..33
                        note = Synthetic Oligonucleotide
source                  1..33
                        mol_type = other DNA
                        organism = synthetic construct
modified_base           32
                        mod_base = OTHER
                        note = uracil
SEQUENCE: 166
cctcaggctt aggcataata ggtatgtatc gtg                                        33

SEQ ID NO: 167          moltype = DNA  length = 37
FEATURE                 Location/Qualifiers
misc_feature            1..37
                        note = Synthetic Oligonucleotide
source                  1..37
                        mol_type = other DNA
                        organism = synthetic construct
modified_base           34
                        mod_base = OTHER
                        note = uracil
SEQUENCE: 167
tgcctcaggc ctaggcataa tcggcatgta tcgtggg                                    37

SEQ ID NO: 168          moltype = DNA  length = 37
FEATURE                 Location/Qualifiers
misc_feature            1..37
                        note = Synthetic Oligonucleotide
source                  1..37
                        mol_type = other DNA
                        organism = synthetic construct
SEQUENCE: 168
tgcctcaggc ctaggcataa tcggcatgta tcgtggg                                    37

SEQ ID NO: 169          moltype = DNA  length = 32
FEATURE                 Location/Qualifiers
misc_feature            1..32
                        note = Synthetic Oligonucleotide
source                  1..32
                        mol_type = other DNA
                        organism = synthetic construct
SEQUENCE: 169
ctcaggctta ggcataatag gtatgtatcg cg                                         32

SEQ ID NO: 170          moltype = DNA  length = 34
FEATURE                 Location/Qualifiers
misc_feature            1..34
                        note = Synthetic Oligonucleotide
source                  1..34
                        mol_type = other DNA
                        organism = synthetic construct
SEQUENCE: 170
tgcctcaggc ttaggcataa taggtatgta tcgc                                       34

SEQ ID NO: 171          moltype = DNA  length = 35
FEATURE                 Location/Qualifiers
misc_feature            1..35
                        note = Synthetic Oligonucleotide
source                  1..35
                        mol_type = other DNA
                        organism = synthetic construct
SEQUENCE: 171
tgcctcaggc ttaggcataa taggtatgta tcgcg                                      35
```

```
SEQ ID NO: 172            moltype = DNA  length = 36
FEATURE                   Location/Qualifiers
misc_feature              1..36
                          note = Synthetic Oligonucleotide
source                    1..36
                          mol_type = other DNA
                          organism = synthetic construct
SEQUENCE: 172
tgcctcaggc ttaggcataa taggtatgta tcgcgg                                    36

SEQ ID NO: 173            moltype = DNA  length = 37
FEATURE                   Location/Qualifiers
misc_feature              1..37
                          note = Synthetic Oligonucleotide
source                    1..37
                          mol_type = other DNA
                          organism = synthetic construct
modified_base             34
                          mod_base = OTHER
                          note = uracil
SEQUENCE: 173
tgcctcaggc ttaggcataa taggtatgta tcgtggg                                   37

SEQ ID NO: 174            moltype = DNA  length = 37
FEATURE                   Location/Qualifiers
misc_feature              1..37
                          note = Synthetic Oligonucleotide
source                    1..37
                          mol_type = other DNA
                          organism = synthetic construct
SEQUENCE: 174
tgcctcaggc ttaggcataa taggtatgta tcgaggg                                   37

SEQ ID NO: 175            moltype = DNA  length = 37
FEATURE                   Location/Qualifiers
misc_feature              1..37
                          note = Synthetic Oligonucleotide
source                    1..37
                          mol_type = other DNA
                          organism = synthetic construct
SEQUENCE: 175
tgcctcaggc ttaggcataa tcggtatgta tcgcggg                                   37

SEQ ID NO: 176            moltype = DNA  length = 37
FEATURE                   Location/Qualifiers
misc_feature              1..37
                          note = Synthetic Oligonucleotide
source                    1..37
                          mol_type = other DNA
                          organism = synthetic construct
SEQUENCE: 176
tgcctcaggc ttaggcataa taggtatgta tcgcggg                                   37

SEQ ID NO: 177            moltype = DNA  length = 28
FEATURE                   Location/Qualifiers
misc_feature              1..28
                          note = Synthetic Oligonucleotide
source                    1..28
                          mol_type = other DNA
                          organism = synthetic construct
SEQUENCE: 177
ctgctgcwga aaatagytct gtgtttgg                                             28

SEQ ID NO: 178            moltype = DNA  length = 24
FEATURE                   Location/Qualifiers
misc_feature              1..24
                          note = Synthetic Oligonucleotide
source                    1..24
                          mol_type = other DNA
                          organism = synthetic construct
SEQUENCE: 178
tgctgaaaat agttctgtgt ttgg                                                 24
```